(12) United States Patent
Bur et al.

(10) Patent No.: US 7,750,161 B2
(45) Date of Patent: Jul. 6, 2010

(54) PYRIDINE DERIVATIVES

(76) Inventors: Daniel Bur, Im Rosengarten 24, CH-4106 Therwil (CH); Martine Clozel, Winterhalde 3b, CH-4102 Binningen (FR); Boris Mathys, Baumgartenstrasse 3, CH-4622 Egerkingen (CH); Claus Mueller, Wittlinger-Strasse 37, D-79576 Weil am Rhein (DE); Michael Scherz, Eigenweg 11, CH-4107 Ettingen (US); Joerg Velker, 8, rue wilson, F-68330 Huningue (DE); Thomas Weller, Hoelzlistrasse 58, CH-4102 Binningen (CH)

( * ) Notice: Subject to any disclaimer, the term of this patent is extended or adjusted under 35 U.S.C. 154(b) by 972 days.

(21) Appl. No.: 10/573,516

(22) PCT Filed: Sep. 21, 2004

(86) PCT No.: PCT/EP2004/010559
§ 371 (c)(1),
(2), (4) Date: Mar. 27, 2006

(87) PCT Pub. No.: WO2005/030209
PCT Pub. Date: Apr. 7, 2005

(65) Prior Publication Data
US 2007/0043081 A1 Feb. 22, 2007

(30) Foreign Application Priority Data
Sep. 26, 2003 (WO) ...................... PCT/EP03/10746

(51) Int. Cl.
*A61K 31/445* (2006.01)
(52) U.S. Cl. ...................................... 546/194; 514/318
(58) Field of Classification Search ................. 546/194; 514/318
See application file for complete search history.

(56) References Cited

U.S. PATENT DOCUMENTS 6,331,541 B1 * 12/2001 Ko et al. ................... 514/237.2

FOREIGN PATENT DOCUMENTS

| EP | 428 434 | 5/1991 |
|----|---------|--------|
| WO | WO 99/21835 | 5/1999 |
| WO | WO 99/40192 | 8/1999 |
| WO | WO 01/09088 | 2/2001 |
| WO | WO 01/45694 | 6/2001 |
| WO | WO 01/45700 | 6/2001 |
| WO | WO 01/45711 | 6/2001 |
| WO | WO 01/66143 | 9/2001 |
| WO | WO 02/00606 | 1/2002 |
| WO | WO 02/02530 | 1/2002 |
| WO | WO 02/47456 | 6/2002 |
| WO | WO 02/47687 | 6/2002 |
| WO | WO 02/058702 | 8/2002 |
| WO | WO 02/076979 | 10/2002 |
| WO | WO 02/078641 | 10/2002 |
| WO | WO 02/078707 | 10/2002 |
| WO | WO 02/079155 | 10/2002 |
| WO | WO 02/079188 | 10/2002 |
| WO | WO 02076979 A | 10/2002 |
| WO | WO 02/089740 | 11/2002 |
| WO | WO 02/089785 | 11/2002 |
| WO | WO 02/089792 | 11/2002 |
| WO | WO 02/089793 | 11/2002 |
| WO | WO 02/090337 | 11/2002 |
| WO | WO 02/090348 | 11/2002 |
| WO | WO 02/090353 | 11/2002 |
| WO | WO 03/048154 | 6/2003 |
| WO | WO 2004/099179 A | 4/2004 |
| WO | WO 2004/043366 | 5/2004 |
| WO | WO 2004/043368 | 5/2004 |
| WO | WO 2004/043369 | 5/2004 |
| WO | WO 2004/043463 | 5/2004 |
| WO | WO 2004/043917 | 5/2004 |
| WO | WO 2004/043948 | 5/2004 |
| WO | WO 2004/073634 | 9/2004 |
| WO | WO 2004/026836 | 11/2004 |

OTHER PUBLICATIONS

F Zaragoza Dorwald Side Reactions in Organic Synthesis 2005, Wiley-VCH.pdf.*

Ames, R.S. et al., "Human urotensin-II is a potent vasoconstrictor and agonist for the orphan receptor GPR14" Nature (1999), 401, pp. 282-286.

Bern, H.A. et al., "Neurohormones from fish tails: the caudal neurosecretory system. I. Urophysiology and the caudal neurosecretory system of fishes", Recent Prog. Horm. Res., (1985), 41, pp. 533-552.

Breu, V. et al., In vitro characterization of Ro-46-2005, a novel synthetic non-peptide antagonist of $ET_A$ and $ET_B$ receptors., FEBS Lett., (1993), 334, pp. 210-214.

(Continued)

*Primary Examiner*—Rita J Desai
*Assistant Examiner*—John Mabry
(74) *Attorney, Agent, or Firm*—Hoxie & Associates LLC

(57) ABSTRACT

The invention relates to novel pyridine derivatives and related compounds and their use as active ingredients in the preparation of pharmaceutical compositions. The invention also concerns related aspects including processes for the preparation of the compounds, pharmaceutical compositions containing one or more of those compounds and especially their use as neurohormonal antagonists.

12 Claims, No Drawings

OTHER PUBLICATIONS

Cheung, B.M. et al., "Plasma concentration of urotensin II is raised in hypertension", J. Hypertens., (2004), 22, pp. 1341-1344.

Clozel, M. et al., "Pharmacology of the Urotensin-II Receptor Antagonist ACT-058362: First Demonstration of a Pathophysiological Role of the Urotensin System", J. Pharmacol. Exp. Ther., (2004), 311, pp. 204-212.

Douglas, S.A., et al., "Differential vasoconstrictor activity of human urotensin-II in vascular tissue isolated from the rat, mouse, dog, pig, marmoset and cynomolgus monkey", Br. J. Pharmacol., (2000), 131, pp. 1262-1274.

Douglas, S.A. et al., "Human urotensin-II is a potent vasoactive peptide: pharmacological characterization in the rat, mouse, dog and primate", J. Cardiovasc. Pharmacol., (2000), 36, Suppl 1:S163-S166.

Garlton, J., et al., "Central effects of urotensin-II following ICV administration in rats", Psychopharmacology (Berlin), (2001), 155, pp. 426-433.

Heller, J. et al., "Increased urotensin II plasma levels in patients with cirrhosis and portal hypertension", J. Hepatol., (2002), 37, pp. 767-772.

Liu, Q. et al., "Identification of urotensin II as the endogenous ligand for the orphan G-protein-coupled receptor GPR14", Biochem. Biophys. Res. Commun., (1999), 266, pp. 174-178.

Malinowski, M., et al., "A Convenient Preparation of 4-Pyridinamine Derivatives", J. Prakt, Chem., (1988), 330, pp. 154-158.

Mori, M. et al., "Urotensin II is the endogenous ligand of a G-protein-coupled orphan receptor, SENR (GPR14)", Biochem. Biophys. Res. Commun., (1999), 265, pp. 123-129.

"Protective Groups in Organic Synthesis", T.W. Greene, P.G.M. Wuts, Wiley-Interscience, (1999).

Russell, F.D., et al., "Cardiostimulant effects of urotensin-II in human heart in vitro", Br. J. Pharmacol., (2001), 132, pp. 5-9.

Shenouda, S. et al., "Localization of urotensin-II immunoreactivity in normal human kidneys and renal carcinoma", J. Histochem. Cytochem, (2002), 50, pp. 885-889.

Silvestre, R.A., et al., "Inhibition of insulin release by urotensin II—a study on the perfused rat pancreas", Horm Metab Res, (2001), 33, pp. 379-381.

Takahashi, K. et al., "Expression of utotensin II and urotensin II receptor mRNAs in various human tumor cell lines and secretion of urotensin II-like immunoreactivity b SW-13 adrenocortical carcinoma cells", Peptides, (2001), 22, pp. 1175-1179.

Takahashi, K. et al., "Expression of urotensin II and its receptor in adrenal tumors and stimulation of proliferation of cultured tumor cells by urotensin II", Peptides, (2003), 24, pp. 301-306.

Totsune, K. et al., "Role of urotensin II in patients on dialysis", Lancent, (2001), 358, pp. 810-811.

Totsune, K. et al., "Increased plasma urotensin II levels in patients with diabetes mellitus" Clin. Sci., (2003), 104, pp. 1-5.

Tsandis, A. et al., "Urotensin II stimulates collagen synthesis of cardiac fibroblasts and hypertrophic signaling in cardiomyocytes via G(alpha)q- and Ras-dependent pathways", J. Am. Coll. Cardiol., (2001), 37, p. 164A.

Zou, Y. et al., "Urotensin II induces hypertrophic responses in cultured cardiomyocytes from neonatal rats" FEBS Lett., (2001), 508, pp. 57-60.

* cited by examiner

PYRIDINE DERIVATIVES

FIELD OF THE INVENTION

The present invention relates to novel 4-(piperidinyl- and pyrrolidinyl-alkyl-ureido)-pyridine derivatives of the General Formula 1 and their use as active ingredients in the preparation of pharmaceutical compositions. The invention also concerns related aspects including processes for the preparation of the compounds, pharmaceutical compositions containing one or more compounds of the General Formula 1 and especially their use as neurohormonal antagonists.

BACKGROUND OF THE INVENTION

Urotensin II is a cyclic 11-amino acid peptide neurohormone considered to be the most potent vasoconstrictor known, up to 28-fold more potent than endothelin-1. The effects of urotensin II are mediated through activation of a G-protein coupled receptor, the UT receptor, also known as GPR14 or SENR (Ames R S, et al, "Human urotensin-II is a potent vasoconstrictor and agonist for the orphan receptor GPR14" Nature (1999) 401, 282-6. Mori M, Sugo T, Abe M, Shimomura Y, Kurihara M, Kitada C, Kikuchi K, Shintani Y, Kurokawa T, Onda H, Nishimura O, Fujino M. "Urotensin II is the endogenous ligand of a G-protein-coupled orphan receptor, SENR (GPR14)" Biochem. Biophys. Res. Commun. (1999) 265, 123-9. Liu Q, Pong S S, Zeng Z, et al, "Identification of urotensin II as the endogenous ligand for the orphan G-protein-coupled receptor GPR14" Biochem. Biophys. Res. Commun. (1999) 266, 174-178) Urotensin II and its receptor are conserved across evolutionarily distant species, suggesting an important physiological role for the system (Bern H A, Pearson D, Larson B A, Nishioka R S. "Neurohormones from fish tails: the caudal neurosecretory system. I. Urophysiology and the caudal neurosecretory system of fishes" Recent Prog. Horm. Res. (1985) 41, 533-552). In euryhaline fish, urotensin II has an osmoregulatory role, and in mammals urotensin II exerts potent and complex hemodynamic actions. The response to urotensin II is dependent on the anatomical source and species of the tissue being studied. (Douglas S A, Sulpizio A C, Piercy V, Sarau H M, Ames R S, Aiyar N V, Ohlstein E H, Willefte R N. "Differential vasoconstrictor activity of human urotensin-II in vascular tissue isolated from the rat, mouse, dog, pig, marmoset and cynomolgus monkey" Br. J. Pharmacol. (2000) 131, 1262-1274. Douglas, S A, Ashton D J, Sauermelch C F, Coatney R W, Ohlstein D H, Ruffolo M R, Ohlstein E H, Aiyar N V, Willette R "Human urotensin-II is a potent vasoactive peptide: pharmacological characterization in the rat, mouse, dog and primate" J. Cardiovasc. Pharmacol. (2000) 36, Suppl 1:S163-6).

Like other neurohormones, urotensin II has growth stimulating and profibrotic actions in addition to its vasoactive properties. Urotensin II increases smooth muscle cell proliferation, and stimulates collagen synthesis (Tzandis A, et al, "Urotensin II stimulates collagen synthesis by cardiac fibroblasts and hypertrophic signaling in cardiomyocytes via G(alpha)q- and Ras-dependent pathways" J. Am. Coll. Cardiol. (2001) 37, 164A. Zou Y, Nagai R, and Yamazaki T, "Urotensin II induces hypertrophic responses in cultured cardiomyocytes from neonatal rats" FEBS Lett (2001) 508, 57-60). Urotensin II regulates hormone release (Silvestre R A, et al, "Inhibition of insulin release by urotensin II-a study on the perfused rat pancreas" Horm Metab Res (2001) 33, 379-81). Urotensin II has direct actions on atrial and ventricular myocytes (Russell F D, Molenaar P, and O'Brien D M "Cardiostimulant effects of urotensin-II in human heart in vitro" Br. J. Pharmacol. (2001) 132, 5-9). Urotensin II is produced by cancer cell lines and its receptor is also expressed in these cells. (Takahashi K, et al, "Expression of urotensin II and urotensin II receptor mRNAs in various human tumor cell lines and secretion of urotensin II-like immunoreactivity by SW-13 adrenocortical carcinoma cells" Peptides (2001) 22, 1175-9; Takahashi K, et al, "Expression of urotensin II and its receptor in adrenal tumors and stimulation of proliferation of cultured tumor cells by urotensin II" Peptides (2003) 24, 301-306; Shenouda S, et al, "Localization of urotensin-II immunoreactivity in normal human kidneys and renal carcinoma" J Histochem Cytochem (2002) 50, 885-889). Urotensin II and its receptor are found in spinal cord and brain tissue, and intracerebroventricular infusion of urotensin II into mice induces behavioral changes (Gartlon J, et al, "Central effects of urotensin-II following ICV administration in rats" Psychopharmacology (Berlin) (2001) 155, 426-33).

Dysregulation of urotensin II is associated with human disease. Elevated circulating levels of urotensin II are detected in hypertensive patients, in heart failure patients, in diabetic patients, and in patients awaiting kidney transplantation (Cheung, B M, et al., "Plasma concentration of urotensin II is raised in hypertension" J. Hypertens. (2004) 22, 1341-1344; Totsune K, et al, "Role of urotensin II in patients on dialysis" Lancet (2001) 358, 810-1; Totsune K, et al, "Increased plasma urotensin II levels in patients with diabetes mellitus" Clin Sci (2003) 104, 1-5; Heller J, et al, "Increased urotensin II plasma levels in patients with cirrhosis and portal hypertension" J Hepatol (2002) 37, 767-772).

Substances with the ability to block the actions of urotensin II are expected to prove useful in the treatment of various diseases. WO-2001/45694, WO-2002/78641, WO-2002/78707, WO-2002/79155, WO-2002/79188, WO-2002/89740, WO-2002/89785, WO-2002/89792, WO-2002/89793, WO-2002/90337, WO-2002/90348, WO-2002/90353, WO-2004/043366, WO-2004/043368, WO-2004/043369, WO-2004/043463, WO-2004/043917 and WO-2004/043948 disclose certain sulfonamides as urotensin II receptor antagonists, and their use to treat diseases associated with a urotensin II imbalance. WO-2001/45700 and WO-2001/45711 disclose certain pyrrolidines or piperidines as urotensin II receptor antagonists and their use to treat diseases associated with a urotensin II imbalance. These derivatives are different from the compounds of the present invention as they do not comprise urea derivatives bearing a 4-pyridinyl-like moiety. WO-2002/047456 and WO-2002/47687 disclose certain 2-amino-quinolones as urotensin II receptor antagonists and their use to treat diseases associated with a urotensin II imbalance. WO-2002/058702 discloses certain 2-amino-quinolines as urotensin II receptor antagonists and their use to treat diseases associated with a urotensin II imbalance. WO-2001/66143 discloses certain 2,3-dihydro-1H-pyrrolo[2,3-b]quinolin-4-ylamine derivatives useful as urotensin II receptor antagonists, WO-2002/00606 discloses certain biphenyl compounds useful as urotensin II receptor antagonists, and WO-2002/02530 and WO-2004/073634 also disclose certain compounds useful as urotensin II receptor antagonists. WO-2002/076979 and WO-2003/048154 disclose certain quinoline derivatives as urotensin II receptor antagonists, and their use to treat diseases associated with a urotensin II imbalance.

EP 428434 discloses certain alkylureidopyridines as neurokinin and substance P antagonists. WO-99/21835 discloses certain ureidoquinolines as H+-ATPase and bone resorption inhibitors. WO-2001/009088 discloses certain substituted heteroarylureas as inhibitors of the CCR-3 receptor. All of these ureidopyridine derivatives differ in their composition from compounds of the present invention. The present invention comprises N-(cyclic amino alkyl)-N'-pyridin-4-yl urea derivatives which are novel compositions of matter and which are useful as urotensin II receptor antagonists.

DESCRIPTION OF THE INVENTION

The present invention relates to compounds of the General Formula 1.

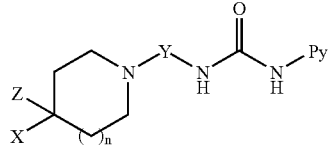

General Formula 1 wherein:

Py represents pyridin-4-yl which is disubstituted in positions 2 and 6, whereby the substituent in position 2 is $C_{1-7}$-alkyl, aryl-$C_{1-7}$-alkyl, or (E)-2-aryl-ethen-1-yl, and the substituent in position 6 is hydrogen or $C_{1-7}$-alkyl;

X represents aryl; aryl-$C_{1-7}$-alkyl-; aryl-O—; aryl-$C_{1-7}$-alkyl-O—; $R^1$—$SO_2NR^2$—; $R^1$—$CONR^2$—; aryl-$R^8$—$CONR^2$—; $R^1$—$NR^3CONR^2$—; $R^1$—$NR^2CO$—; or X and Z represent together with the carbon atom to which they are attached an exocyclic double bond which bears an aryl substituent at the thus formed methylene group;

Z represents hydrogen; in case X represents aryl or aryl-$C_{1-7}$-alkyl Z represents hydrogen, hydroxyl, carboxyl or $R^4$—$NR^5CO$—; in case X represents $R^1$—$NR^2CO$— Z represents hydrogen or $C_{1-7}$-alkyl; or in case X represents aryl or aryl-$C_{1-7}$-alkyl and n represents the number 0, Z represents hydrogen, hydroxyl, carboxyl, $R^4$—$NR^5CO$—, aryl or aryl-$C_{1-7}$-alkyl;

Y represents —$C(R^6)(R^7)(CH_2)_m$— or —$(CH_2)_mC(R^6)(R^7)$—;

m represents the numbers 1 or 2;

n represents the numbers 0 or 1;

$R^1$ represents aryl or aryl-$C_{1-7}$-alkyl;

$R^2$ represents hydrogen; $C_{1-7}$-alkyl; 2-hydroxyethyl; aryl-$C_{1-7}$-alkyl; or a saturated carbocyclic ring;

$R^3$ represents hydrogen or $C_{1-7}$-alkyl;

$R^4$ represents hydrogen; $C_{1-7}$-alkyl; aryl; aryl-$C_{1-7}$-alkyl; or forms together with $R^5$ a saturated 4-, 5- or 6-membered ring including the nitrogen atom to which $R^4$ and $R^5$ are attached as ring atom;

$R^5$ represents hydrogen; $C_{1-7}$-alkyl; 2-hydroxyethyl; or forms together with $R^4$ a saturated 4-, 5- or 6-membered ring including the nitrogen atom to which $R^4$ and $R^5$ are attached as ring atom;

$R^6$ represents hydrogen; $C_{1-7}$-alkyl; aryl; aryl-$C_{1-7}$-alkyl; or forms together with $R^7$ a saturated carbocyclic ring including the carbon atom to which $R^6$ and $R^7$ are attached as ring atom;

$R^7$ represents hydrogen; methyl; or forms together with $R^6$ a saturated carbocyclic ring including the carbon atom to which $R^6$ and $R^7$ are attached as ring atom.

$R^8$ represents a saturated carbocyclic ring.

In a preferred embodiment also the following forms are encompassed: optically pure enantiomers or diastereomers, mixtures of enantiomers or diastereomers, diastereomeric racemates, and mixtures of diastereomeric racemates; as well as their pharmaceutically acceptable salts, solvent complexes, and morphological forms.

The term 'aryl' means a substituted or unsubstituted aromatic carbocyclic or heterocyclic ring system, consisting of a five- or six-membered aromatic ring, or of a fused five-six or six-six aromatic ring system. Preferred aryl groups are for example 2-furyl; 2-thienyl; phenyl; 2-methylphenyl; 3-methylphenyl; 4-methylphenyl; 2-biphenyl; 3-biphenyl; 4-biphenyl; 2-methoxyphenyl; 3-methoxyphenyl; 4-methoxyphenyl; 3,4-dimethoxyphenyl; 2,6-dimethoxyphenyl; 2,5-dimethoxyphenyl; 2-phenoxyphenyl; 3-phenoxyphenyl; 4-phenoxyphenyl; 2-cyanophenyl; 3-cyanophenyl; 4-cyanophenyl; 2-fluorophenyl; 3-fluorophenyl; 4-fluorophenyl; 2,4-difluorophenyl; 2,5-difluorophenyl; 2,6-difluorophenyl; 3,4-difluorophenyl; 2-chlorophenyl; 3-chlorophenyl; 4-chlorophenyl; 3,4-dichlorophenyl; 2-bromophenyl; 3-bromophenyl; 4-bromophenyl; 2-trifluoromethylphenyl; 3-trifluoromethylphenyl; 4-trifluoromethylphenyl; 3,5-bis-trifluoromethylphenyl; 4-trifluoromethoxyphenyl; 4-ethylphenyl; 4-n-propylphenyl; 2-iso-propylphenyl; 4-iso-propylphenyl; 4-tert-butylphenyl; 4-n-pentylphenyl; 4-bromo-2-ethylphenyl; 2-methanesulfonylphenyl; 3-methanesulfonylphenyl; 4-methanesulfonylphenyl; 4-acetamidophenyl; 4-hydroxyphenyl; 4-iso-propyloxyphenyl; 4-n-butoxyphenyl; 2-methoxy-4-methylphenyl; 4-methoxy-2,3,6-trimethylphenyl; 5-bromo-2-methoxy-phenyl; 2-pyridyl; 3-pyridyl; 4-pyridyl; 1-naphthyl; 2-naphthyl; 4-(pyrrol-1-yl)phenyl; 4-benzoylphenyl; 5-dimethylaminonaphth-1-yl; 5-chloro-3-methylthiophen-2-yl; 5-chloro-3-methyl-benzo[b]thiophen-2-yl; 3-(phenylsulfonyl)-thiophen-2-yl; 2-chloro-thien-5-yl; 2,5-dichloro-thien-3-yl; 4,5-dichlorothien-2-yl; 2-(2,2,2-trifluoroacetyl)-1-2,3,4-tetrahydroisoquinolin-7-yl; 4-(3-chloro-2-cyanophenyloxy)phenyl; 2-(5-benzamidomethyl) thiophenyl; 5-quinolyl-; 6-quinolyl; 7-quinolyl; 8-quinolyl; (2-acetylamino-4-methyl)thiazol-5-yl; or 1-methylimidazol-4-yl. For the substituents X, $R^4$ and $R^6$ aryl means preferably phenyl or phenyl mono- or disubstituted independently with $C_{1-7}$-alkyl, $C_{1-7}$-alkyl-O—, trifluoromethyl or halogen. For the substituent x aryl means preferably phenyl or phenyl mono- or disubstituted independently with $C_{1-7}$-alkyl, $C_{1-7}$-alkyl-O—, trifluoromethyl or halogen.

The term '$C_{1-7}$-alkyl' means straight or branched chain groups with one to seven carbon atoms such as methyl, ethyl, n-propyl, 3-allyl, iso-propyl, n-butyl, iso-butyl, tert.-butyl, n-pentyl, iso-pentyl, n-hexyl and n-heptyl; preferably one to four carbon atoms. Preferred examples of $C_{1-7}$-alkyl groups are methyl, ethyl and n-propyl. Most preferred examples of $C_{1-7}$-alkyl groups are methyl and ethyl.

The term 'saturated carboxyclic ring' means a saturated cyclic alkyl group with three to six carbon atoms. Preferred examples of saturated carbocyclic rings are cyclopropyl, cyclobutyl, cyclopentyl, and cyclohexyl. For the substituent $R^8$ 'saturated carboxyclic ring' means preferably 1,1-cyclopropane-diyl.

The term 'aryl-$C_{1-7}$-alkyl' means a $C_{1-7}$-alkyl group as previously defined in which one hydrogen atom has been replaced by an aryl group as previously defined. Preferred examples of aryl-$C_{1-7}$-alkyl groups are 3-phenylpropyl, phenethyl, benzyl, and benzyl substituted in the phenyl ring with $C_{1-7}$-alkyl, $C_{1-7}$-alkyl-O—, trifluoromethyl or halogen such as 4-methylbenzyl, 3-methylbenzyl, 2-methylbenzyl, 4-methoxybenzyl, 3-methoxybenzyl, 2-methoxybenzyl, 4-trifluoromethylbenzyl, 3-trifluoromethylbenzyl, 2-trifluoromethylbenzyl, 4-chlorobenzyl, 3-chlorobenzyl, 2-chlorobenzyl, 4-fluorobenzyl, 3-fluorobenzyl, and 2-fluorobenzyl.

The term 'aryl-O—' means an aryl group as previously defined that is attached to an oxygen atom. Preferred examples of aryl-O— groups are phenoxy and phenoxy substituted in the phenyl ring with $C_{1-7}$-alkyl, $C_{1-7}$-alkyl-O—, trifluoromethyl or halogen such as 4-methylphenoxy, 4-methoxyphenoxy, 4-trifluoromethylphenoxy, 4-chlorophenoxy, 4-fluorophenoxy, 3-methylphenoxy, 3-methoxyphenoxy, 3-trifluoromethylphenoxy, 3-chlorophenoxy, 3-fluorophenoxy, 2-methylphenoxy, 2-methoxyphenoxy, 2-trifluoromethylphenoxy, 2-chlorophenoxy and 2-fluorophenoxy.

The term 'aryl-$C_{1-7}$-alkyl-O—' means a $C_{1-7}$-alkyl group as previously defined in which one hydrogen atom has been replaced by an oxygen atom and one additional hydrogen atom has been replaced by an aryl group as previously defined. Preferred examples of aryl-$C_{1-7}$-alkyl-O— groups are 3-phenylpropyloxy, 2-phenethyloxy, benzyloxy and benzyloxy substituted in the phenyl ring with $C_{1-7}$-alkyl, $C_{1-7}$-alkyl-O—, trifluoromethyl or halogen such as 4-methylbenzyloxy, 3-methylbenzyloxy, 2-methylbenzyloxy, 4-methoxybenzyloxy, 3-methoxybenzyloxy, 2-methoxybenzyloxy, 4-trifluoromethylbenzyloxy, 3-trifluoromethylbenzyloxy, 2-trifluoromethylbenzyloxy, 4-chlorobenzyloxy, 3-chlorobenzyloxy, 2-chlorobenzyloxy, 4-fluorobenzyloxy, 3-fluorobenzyloxy and 2-fluorobenzyloxy.

The term '$C_{1-7}$-alkyl-O—' means a $C_{1-7}$-alkyl group as previously defined that is attached to an oxygen atom. Preferred examples of $C_{1-7}$-alkyl-O— groups are methoxy, ethoxy, n-propyloxy and iso-propyloxy.

The term '(E)-2-aryl-ethen-1-yl' means groups such as (E)-2-phenylethen-1-yl, (E)-2-(4-fluorophenyl)ethen-1-yl and (E)-3-phenylpropen-1-yl. Preferred examples are (E)-2-phenylethen-1-yl and (E)-2-(4-fluorophenyl)ethen-1-yl.

Preferred examples of groups wherein 'X and Z represent together with the carbon atom to which they are attached an exocyclic double bond which bears an aryl substituent at the thus formed methylene group' are benzylidene and benzylidene substituted in the phenyl ring with $C_{1-7}$-alkyl, $C_{1-7}$-alkyl-O— or halogen such as 4-methylbenzylidene, 3-methylbenzylidene, 2-methylbenzylidene, 4-methoxybenzylidene, 3-methoxybenzylidene, 2-methoxybenzylidene, 4-chlorobenzylidene, 3-chlorobenzylidene, 2-chlorobenzylidene, 4-fluorobenzylidene, 3-fluorobenzylidene, 2-fluorobenzylidene.

Preferred examples of $R^4$ and $R^5$ representing a 'saturated 4-, 5- or 6-membered ring including the nitrogen atom to which $R^4$ and $R^5$ are attached as ring atom' are azetidine, pyrrolidine, piperidine and morpholine.

Preferred examples of $R^6$ and $R^7$ representing 'a saturated carbocyclic ring including the carbon atom to which $R^6$ and $R^7$ are attached as ring atom' are 1,1-cyclopropane-diyl, 1,1-cyclobutane-diyl, 1,1-cyclopentane-diyl and 1,1-cyclohexane-diyl.

The present invention encompasses pharmaceutically acceptable salts of compounds of the General Formula 1. This encompasses either salts with inorganic acids or organic acids like hydrohalogenic acids, e.g. hydrochloric or hydrobromic acid, sulfuric acid, phosphoric acid, nitric acid, citric acid, formic acid, acetic acid, maleic acid, tartaric acid, malic acid, methylsulfonic acid, p-tolylsulfonic acid and the like or in case the compound of formula 1 is acidic in nature with an inorganic base like an alkali or earth alkali base, e.g. sodium, potassium, or calcium salts, etc. The compounds of General Formula 1 can also be present in form of zwitterions.

The present invention encompasses different salvation complexes of compounds of General Formula 1. The solvation can be effected in the course of the manufacturing process or can take place separately, e.g. as a consequence of hygroscopic properties of an initially anhydrous compound of General Formula 1.

The present invention further encompasses different morphological forms, e.g. crystalline forms, of compounds of General Formula 1 and their salts and solvation complexes. Particular heteromorphs may exhibit different dissolution properties, stability profiles, and the like, and are all included in the scope of the present invention.

The compounds of the General Formula 1 might have one or more asymmetric carbon atoms and may be prepared in form of configurational isomers, optically pure enantiomers or diastereomers, mixtures of enantiomers or diastereomers, diastereomeric racemates, and mixtures of diastereomeric racemates. The present invention encompasses all these forms. They are prepared by stereoselective synthesis, or by separation of mixtures in a manner known per se, i.e. by column chromatography, thin layer chromatography, HPLC, crystallization, etc.

Preferred compounds of the invention are compounds of General Formula 2.

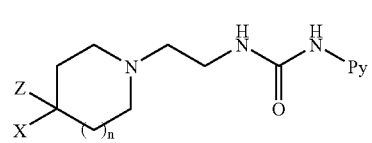

General Formula 2 wherein:

Py represents pyridin-4-yl which is disubstituted in positions 2 and 6, whereby the substituent in position 2 is $C_{1-7}$-alkyl or aryl-$C_{1-7}$-alkyl and the substituent in position 6 is methyl or ethyl;

X represents aryl; aryl-$C_{1-7}$-alkyl-; aryl-O—; aryl-$C_{1-7}$-alkyl-O—; $R^1$—$SO_2NR^2$—; $R^1$—$CONR^2$—; aryl-$R^8$—$CONR^2$—; $R^1$—$NR^3CONR^2$—; or $R^1$—$NR^2CO$—;

Z represents hydrogen; in case X represents aryl or aryl-$C_{1-7}$-alkyl and n represents the number 1 Z represents hydrogen, hydroxyl or $R^4$—$NR^5CO$—;

n represents the numbers 0 or 1;

$R^1$ represents aryl or aryl-$C_{1-7}$-alkyl;

$R^2$ represents hydrogen; $C_{1-7}$-alkyl; 2-hydroxyethyl; aryl-$C_{1-7}$-alkyl; or a saturated carbocyclic ring;

$R^3$ represents hydrogen or $C_{1-7}$-alkyl;

$R^4$ represents hydrogen; $C_{1-7}$-alkyl; aryl; aryl-$C_{1-7}$-alkyl; or forms together with $R^5$ a saturated 4-, 5- or 6-membered ring including the nitrogen atom to which $R^4$ and $R^5$ are attached as ring atom;

$R^5$ represents hydrogen; $C_{1-7}$-alkyl; 2-hydroxyethyl; or forms together with $R^4$ a saturated 4-, 5- or 6-membered ring including the nitrogen atom to which $R^4$ and $R^5$ are attached as ring atom.

$R^8$ represents a saturated carbocyclic ring.

In a preferred embodiment also the following forms are encompassed: optically pure enantiomers or diastereomers, mixtures of enantiomers or diastereomers, diastereomeric racemates, and mixtures of diastereomeric racemates; as well as their pharmaceutically acceptable salts, solvent complexes, and morphological forms.

Preferred compounds of General Formula 1 are the compounds of General Formula 3:

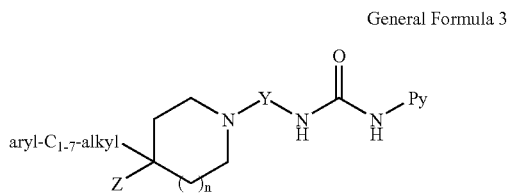

General Formula 3 wherein n, Y, Z and Py have the meaning given in General Formula 1.

Preferred compounds of General Formula 1 are the compounds of General Formula 4:

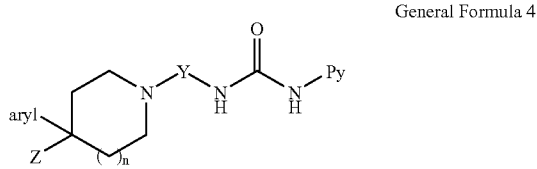

General Formula 4 wherein n, Y, Z and Py have the meaning given in General Formula 1.

Preferred compounds of General Formula 1 are the compounds of General Formula 5:

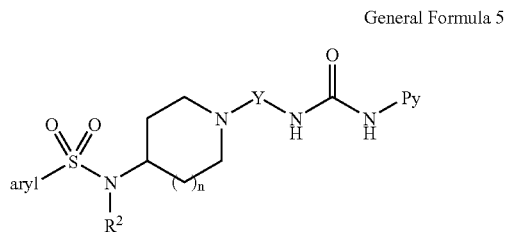

General Formula 5 wherein $R^2$, Y, n and Py have the meaning given in General Formula 1.

Preferred compounds of General Formula 1 are the compounds of General Formula 6:

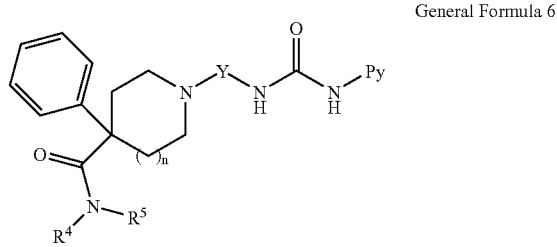

General Formula 6 wherein $R^4$, $R^5$, Y, n and Py have the meaning given in General Formula 1.

Preferred compounds of General Formula 1 are the compounds of General Formula 7:

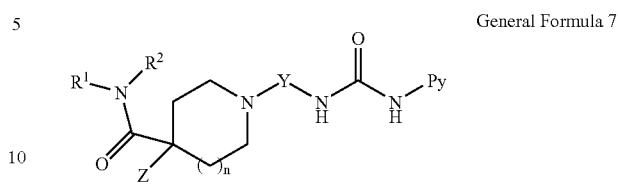

General Formula 7 wherein $R^1$, $R^2$, Z, Y, n and Z have the meaning given in General Formula 1.

Preferred compounds of General Formula 1 are the compounds of General Formula 8:

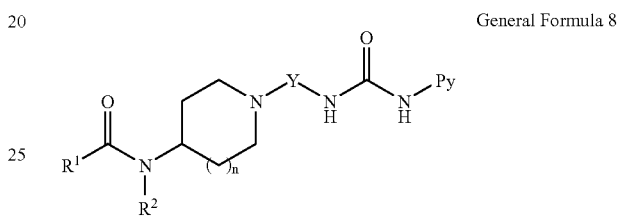

General Formula 8 wherein $R^1$, $R^2$, n, Y and Py have the meaning given in General Formula 1.

Preferred compounds of General Formula 1 are the compounds of General Formula 9:

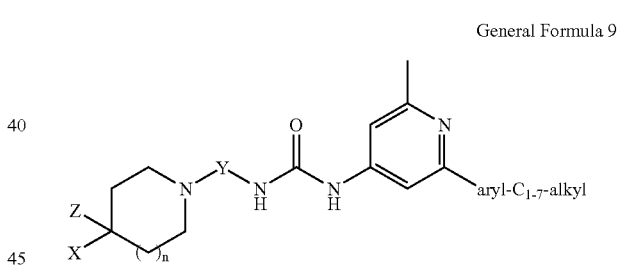

General Formula 9 wherein X, Y, Z, n and Py have the meaning given in General Formula 1.

Preferred compounds of General Formula 1 are the compounds of General Formula 10:

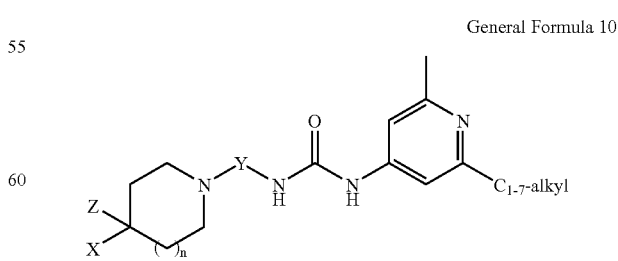

General Formula 10 wherein X, Y, Z, n and Py have the meaning given in General Formula 1.

Preferred compounds of General Formula 1 are the compounds of General Formula 11:

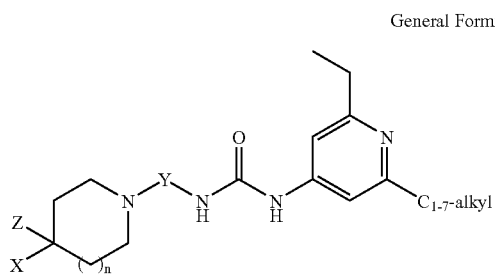

General Formula 11 wherein X, Y, Z, n and Py have the meaning given in General Formula 1.

Preferred compounds of General Formula 2 are the compounds of General Formula 12:

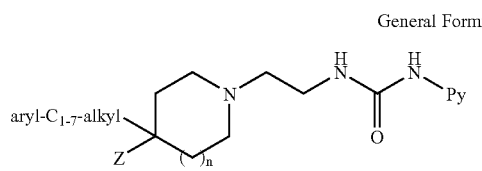

General Formula 12 wherein n, Z and Py have the meaning given in General Formula 2.

Preferred compounds of General Formula 2 are the compounds of General Formula 13:

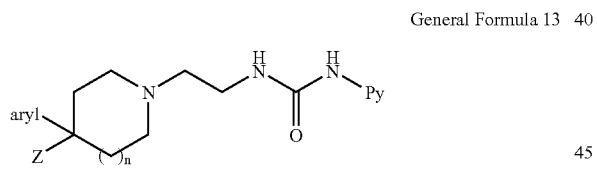

General Formula 13 wherein n, Z and Py have the meaning given in General Formula 2.

Preferred compounds of General Formula 2 are the compounds of General Formula 14:

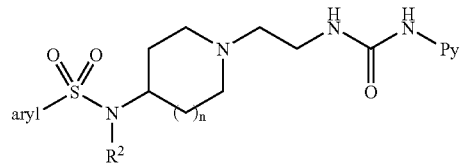

General Formula 14 wherein $R^2$, n and Py have the meaning given in General Formula 2.

Preferred compounds of General Formula 2 are the compounds of General Formula 15:

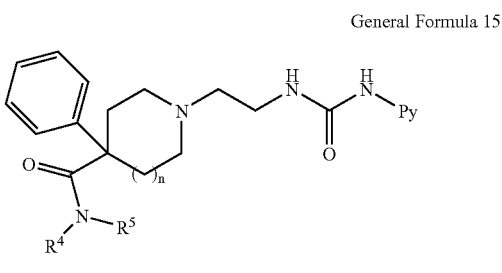

General Formula 15 wherein $R^4$, $R^5$, n and Py have the meaning given in General Formula 2.

Preferred compounds of General Formula 2 are the compounds of General Formula 16:

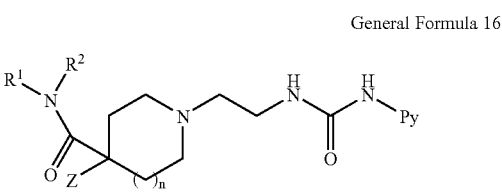

General Formula 16 wherein $R^1$, $R^2$, Z, n and Z have the meaning given in General Formula 2.

Preferred compounds of General Formula 2 are the compounds of General Formula 17:

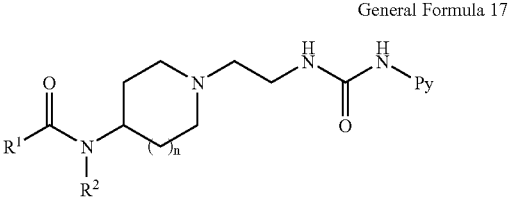

General Formula 17 wherein $R^1$, $R^2$, n and Py have the meaning given in General Formula 2.

Preferred compounds of General Formula 2 are the compounds of General Formula 18:

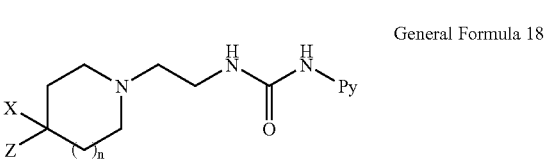

General Formula 18 wherein X, Z and Py have the meaning given in General Formula 2.

Preferred compounds of General Formula 2 are the compounds of General Formula 19:

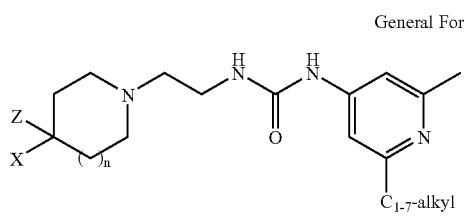

General Formula 19 wherein X, Z and n have the meaning given in General Formula 2.

Preferred compounds of General Formula 2 are the compounds of General Formula 20:

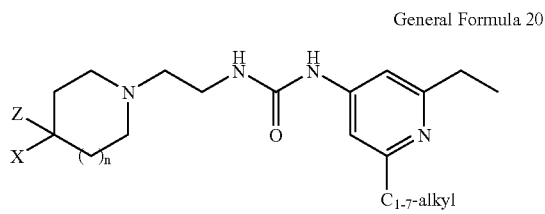

General Formula 20 wherein X, Z and n have the meaning given in General Formula 2.

Preferred compounds of General Formula 2 are the compounds of General Formula 21:

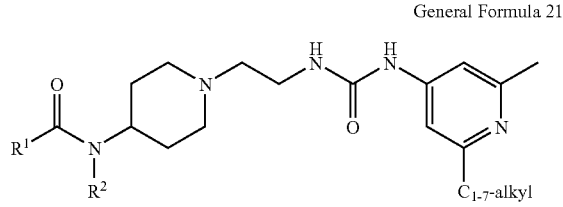

General Formula 21 wherein $R^1$ and $R^2$ have the meaning given in General Formula 2.

Preferred compounds of General Formula 2 are the compounds of General Formula 22:

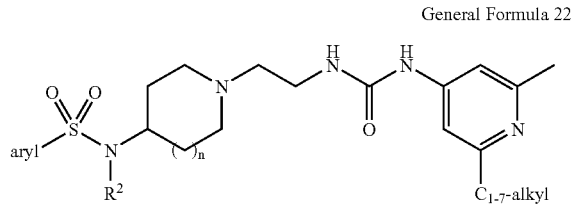

General Formula 22 wherein $R^2$ and n have the meaning given in General Formula 2.

Preferred compounds of General Formula 2 are the compounds of General Formula 23:

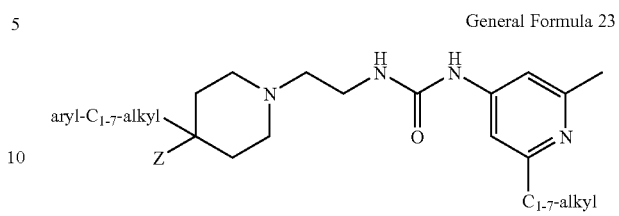

General Formula 23 wherein Z has the meaning given in General Formula 2.

Preferred compounds of General Formula 2 are the compounds of General Formula 24:

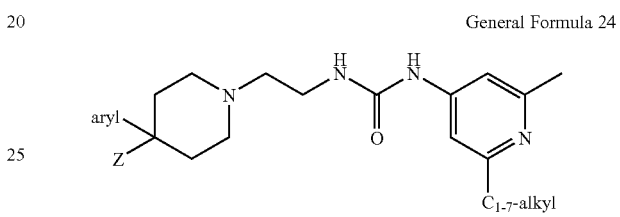

General Formula 24 wherein Z has the meaning given in General Formula 2.

The present invention also relates to compounds of the General Formula 25:

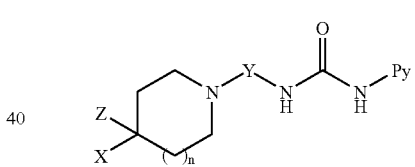

General Formula 25 wherein:

Py represents pyridin-4-yl which is disubstituted in positions 2 and 6, whereby the substituent in position 2 is $C_{1-7}$-alkyl, aryl-$C_{1-7}$-alkyl, or (E)-2-aryl-ethen-1-yl, and the substituent in position 6 is hydrogen or $C_{1-7}$-alkyl;

X represents aryl; aryl-O—; aryl-$C_{1-7}$-alkyl-; $R^1$—$SO_2NR^2$—; $R^1$—$CONR^2$—; $R^1$—$NR^3CONR^2$—; $R^1$—$NR^2CO$—; or X and Z represent together with the carbon atom to which they are attached an exocyclic double bond which bears an aryl substituent at the thus formed methylene group;

Y represents —$C(R^4)(R^5)(CH_2)_m$— or —$(CH_2)_mC(R^4)(R^5)$—;

Z represents hydrogen; in case X represents aryl or aryl-$C_{1-7}$-alkyl Z represents hydrogen, hydroxyl, carboxyl, $R^1$—$NR^2CO$—; or in case X represents aryl or aryl-$C_{1-7}$-alkyl and n represents the number 0, Z represents hydrogen, hydroxyl, carboxyl, $R^1$—$NR^2CO$—, aryl, aryl-$C_{1-7}$-alkyl;

n represents the numbers 0 or 1;

m represents the numbers 1 or 2;

$R^1$ represents aryl; $C_{1-7}$-alkyl; aryl-$C_{1-7}$-alkyl; or a saturated carbocyclic ring;

$R^2$ and $R^3$ represent independently hydrogen; $C_{1-7}$-alkyl; aryl-$C_{1-7}$-alkyl; or a saturated carbocyclic ring;

$R^4$ represents hydrogen; $C_{1-7}$-alkyl; aryl; aryl-$C_{1-7}$-alkyl; or forms together with $R^5$ a saturated carbocyclic ring including the carbon atom to which $R^4$ and $R^5$ are attached as ring atom;

$R^5$ represents hydrogen; methyl; or forms together with $R^4$ a saturated carbocyclic ring including the carbon atom to which $R^4$ and $R^5$ are attached as ring atom;

and optically pure enantiomers or diastereomers, mixtures of enantiomers or diastereomers, diastereomeric racemates, and mixtures of diastereomeric racemates; as well as their pharmaceutically acceptable salts, solvent complexes, and morphological forms.

In the definitions of the General Formula 25 the expression 'aryl' means a substituted or unsubstituted aromatic carbocyclic or heterocyclic ring system, consisting of a five- or six-membered aromatic ring, or of a fused five-six or six-six aromatic ring system. Preferred aryl groups are for example 2-furyl; 2-thienyl; phenyl; 2-methylphenyl; 2-biphenyl; 2-methoxyphenyl; 2-phenoxyphenyl; 2-chlorophenyl; 2-bromophenyl; 2-i-propylphenyl; 2-fluorophenyl; 2-methylsulfonylphenyl; 2-cyanophenyl; 2-trifluoromethylphenyl; 3-methylphenyl; 3-biphenyl; 3-phenoxyphenyl; 3-methoxyphenyl; 3-chlorophenyl; 3-bromophenyl; 3-fluorophenyl; 3-cyanophenyl; 3-trifluoromethylphenyl; 3-carboxyphenyl; 4-methylphenyl; 4-ethylphenyl; 4-i-propylphenyl; 4-phenyloxyphenyl; 4-trifluoromethylphenyl; 4-trifluoromethoxyphenyl; 4-phenoxyphenyl; 4-cyanophenyl; 4-hydroxyphenyl; 4-acetylaminophenyl; 4-methanesulfonylphenyl; 4-n-propylphenyl; 4-iso-propylphenyl; 4-tert-butylphenyl; 4-n-pentylphenyl; 4-biphenyl; 4-chlorophenyl; 4-bromophenyl; 4-bromo-2-ethylphenyl; 4-fluorophenyl; 2,4-difluorophenyl; 4-n-butoxyphenyl; 2,6-dimethoxyphenyl; 3,5-bis-trifluoromethylphenyl; 2-pyridyl; 3-pyridyl; 4-pyridyl; 1-naphthyl; 2-naphthyl; 4-(pyrrol-1-yl)phenyl; 4-benzoylphenyl; 5-dimethylaminonaphth-1-yl; 5-chloro-3-methylthiophen-2-yl; 5-chloro-3-methyl-benzo[b]thiophen-2-yl; 3-(phenylsulfonyl)-thiophen-2-yl; 2-(2,2,2-trifluoroacetyl)-1-2,3,4-tetrahydroisoquinolin-7-yl; 4-(3-chloro-2-cyanophenyloxy)phenyl; 2-(5-benzamidomethyl)thiophenyl; 4,5-dichlorothien-2-yl; 5-quinolyl-; 6-quinolyl; 7-quinolyl; 8-quinolyl; (2-acetylamino-4-methyl)thiazol-5-yl; or 1-methylimidazol-4-yl.

In the definitions of the General Formula 25 the expression '$C_{1-7}$-alkyl' means straight or branched chain groups with one to seven carbon atoms, preferably one to four carbon atoms. Preferred examples of $C_{1-7}$-alkyl groups are methyl, ethyl, n-propyl, isopropyl, n-butyl, iso-butyl, sec-butyl, tert-butyl, n-pentyl, n-hexyl, and n-heptyl.

In the definitions of the General Formula 25 the expression 'saturated carboxylic ring' means a saturated cyclic alkyl group with three to six carbon atoms. Preferred examples of saturated carbocyclic rings are cyclopropyl, cyclobutyl, cyclopentyl, and cyclohexyl.

In the definitions of the General Formula 25 the expression 'aryl-$C_{1-7}$-alkyl' means a $C_{1-7}$-alkyl group as previously defined in which one hydrogen atom has been replaced by an aryl group as previously defined. Preferred examples of aryl-$C_{1-7}$-alkyl groups are 3-phenylpropyl, phenethyl, benzyl and benzyl substituted in the phenyl ring with hydroxy, $C_{1-7}$-alkyl, $C_{1-7}$-alkyloxy, or halogen.

Examples of particularly preferred compounds of General Formula 1 are selected from the group consisting of:

| Example number | |
|---|---|
| 1 | 1-[2-(4-Benzyl-piperidin-1-yl)-ethyl]-3-(2,6-dimethyl-pyridin-4-yl)-urea |
| 2 | 1-{2-[3-(2,6-Dimethyl-pyridin-4-yl)-ureido]-ethyl}-4-phenyl-piperidine-4-carboxylic acid benzyl-methyl-amide |
| 3 | N-(1-{2-[3-(2,6-Dimethyl-pyridin-4-yl)-ureido]-ethyl}-piperidin-4-yl)-4-methoxy-N-propyl-benzenesulfonamide |
| 4 | N-(1-{2-[3-(2,6-Dimethyl-pyridin-4-yl)-ureido]-ethyl}-piperidin-4-yl)-4-fluoro-N-propyl-benzenesulfonamide |
| 5 | 1-(2,6-Dimethyl-pyridin-4-yl)-3-[2-(3,3-diphenyl-pyrrolidin-1-yl)-ethyl]-urea |
| 6 | 1-[2-(4-Benzyl-4-hydroxy-piperidin-1-yl)-ethyl]-3-(2,6-dimethyl-pyridin-4-yl)-urea |
| 15 | N-(1-{2-[3-(2,6-Dimethyl-pyridin-4-yl)-ureido]-ethyl}-piperidin-4-yl)-N-ethyl-4-methoxy-benzenesulfonamide |
| 16 | N-(1-{2-[3-(2,6-Dimethyl-pyridin-4-yl)-ureido]-ethyl}-piperidin-4-yl)-N-ethyl-4-fluoro-benzenesulfonamide |
| 17 | 1-(2-{3-[2-Methyl-6-((E)-styryl)-pyridin-4-yl]-ureido}-ethyl)-4-phenyl-piperidine-4-carboxylic acid benzyl-methyl-amide |
| 22 | N-Ethyl-4-methoxy-N-(1-{2-[3-(2-methyl-6-phenethyl-pyridin-4-yl)-ureido]-ethyl}-piperidin-4-yl)-benzenesulfonamide |
| 23 | 1-{2-[3-(2-Methyl-6-propyl-pyridin-4-yl)-ureido]-ethyl}-4-phenyl-piperidine-4-carboxylic acid benzyl-methyl-amide |
| 24 | 1-[2-(4-Benzyl-piperidin-1-yl)-ethyl]-3-(2-methyl-6-propyl-pyridin-4-yl)-urea |
| 25 | N-Ethyl-4-methoxy-N-(1-{2-[3-(2-methyl-6-propyl-pyridin-4-yl)-ureido]-ethyl}-piperidin-4-yl)-benzenesulfonamide |
| 26 | 1-[2-(4-Benzyl-piperidin-1-yl)-ethyl]-3-(2-ethyl-6-methyl-pyridin-4-yl)-urea |
| 27 | N-Ethyl-N-(1-{2-[3-(2-ethyl-6-methyl-pyridin-4-yl)-ureido]-ethyl}-piperidin-4-yl)-4-methoxy-benzenesulfonamide |
| 28 | 1-{2-[3-(2-Ethyl-6-methyl-pyridin-4-yl)-ureido]-ethyl}-4-phenyl-piperidine-4-carboxylic acid benzyl-methyl-amide |
| 35 | 1-[2-(4-Benzyl-4-hydroxy-piperidin-1-yl)-ethyl]-3-(2-phenethyl-pyridin-4-yl)-urea |
| 36 | 1-[2-(4-Benzyl-4-hydroxy-piperidin-1-yl)-ethyl]-3-{2-[2-(4-fluoro-phenyl)-ethyl]-pyridin-4-yl}-urea |

-continued

Examples of particularly preferred compounds of General Formula 1 are selected from the group consisting of:

| Example number | |
|---|---|
| 37 | 1-{2-[3-(2-Methyl-6-phenethyl-pyridin-4-yl)-ureido]-ethyl}4-phenyl piperidine-4-carboxylic acid benzyl-methyl-amide |
| 7 | 2-(4-Chloro-phenyl)-N-(1-{2-[3-(2,6-dimethyl-pyridin-4-yl)-ureido]-ethyl}-piperidin-4-yl)-N-ethyl-acetamide |
| 8 | N-Cyclopropyl-N-(1-{2-[3-(2,6-dimethyl-pyridin-4-yl)-ureido]-ethyl}-piperidin-4-yl)-4-fluoro-benzenesulfonamide |
| 11 | 1-{2-[3-(2,6-Dimethyl-pyridin-4-yl)-ureido]-ethyl}-4-phenyl-piperidine-4-carboxylic acid benzyl-(2-hydroxy-ethyl)-amide |
| 12 | 1-{2-[3-(2-Ethyl-6-methyl-pyridin-4-yl)-ureido]-ethyl}-4-phenyl-piperidine-4-carboxylic acid benzyl-(2-hydroxy-ethyl)-amide |
| 30 | N-Ethyl-N-(1-{2-[3-(2-ethyl-6-methyl-pyridin-4-yl)-ureido]-ethyl}-piperidin-4-yl)-4-fluoro-benzenesulfonamide |
| 31 | 1-[2-(4-Benzyl-piperidin-1-yl)-ethyl]-3-(2,6-diethyl-pyridin-4-yl)-urea |
| 33 | N-(1-{2-[3-(2,6-Diethyl-pyridin-4-yl)-ureido]-ethyl}-piperidin-4-yl)-N-ethyl-4-methoxy-benzenesulfonamide |
| 34 | N-(1-{2-[3-(2,6-Diethyl-pyridin-4-yl)-ureido]-ethyl}-piperidin-4-yl)-N-ethyl-4-fluoro-benzenesulfonamide |
| 41 | N-(1-{2-[3-(2-Ethyl-6-methyl-pyridin-4-yl)-ureido]-ethyl}-piperidin-4-yl)-4-fluoro-N-propyl-benzenesulfonamide |
| 42 | 4-Bromo-N-ethyl-N-(1-{2-[3-(2-ethyl-6-methyl-pyridin-4-yl)-ureido]-ethyl}-piperidin-4-yl)-benzenesulfonamide |
| 43 | N-(1-{2-[3-(2-Ethyl-6-methyl-pyridin-4-yl)-ureido]-ethyl}-piperidin-4-yl)-4-methoxy-N-propyl-benzenesulfonamide |
| 49 | N-(1-{2-[3-(2,6-Dimethyl-pyridin-4-yl)-ureido]-ethyl}-piperidin-4-yl)-4-methoxy-N-methyl-benzenesulfonamide |
| 60 | N-(1-{2-[3-(2,6-Dimethyl-pyridin-4-yl)-ureido]-ethyl}-piperidin-4-yl)-4-ethyl-N-methyl-benzenesulfonamide |
| 61 | N-{4-[(1-{2-[3-(2,6-Dimethyl-pyridin-4-yl)-ureido]-ethyl}-piperidin-4-yl)-methyl-sulfamoyl]-phenyl}-acetamide |
| 62 | N-(1-{2-[3-(2,6-Dimethyl-pyridin-4-yl)-ureido]-ethyl}-piperidin-4-yl)-4-isopropoxy-N-methyl-benzenesulfonamide |
| 63 | N-(1-{2-[3-(2,6-Dimethyl-pyridin-4-yl)-ureido]-ethyl}-piperidin-4-yl)-4,N-dimethyl-benzenesulfonamide |
| 67 | 4-Chloro-N-(1-{2-[3-(2,6-dimethyl-pyridin-4-yl)-ureido]-ethyl}-piperidin-4-yl)-N-methyl-benzenesulfonamide |
| 70 | 3,4-Dichloro-N-(1-{2-[3-(2,6-dimethyl-pyridin-4-yl)-ureido]-ethyl}-piperidin-4-yl)-N-methyl-benzenesulfonamide |
| 71 | N-(1-{2-[3-(2,6-Dimethyl-pyridin-4-yl)-ureido]-ethyl}-piperidin-4-yl)-N-methyl-4-trifluoromethyl-benzenesulfonamide |
| 74 | 5-Chloro-thiophene-2-sulfonic acid (1-{2-[3-(2,6-dimethyl-pyridin-4-yl)-ureido]-ethyl}-piperidin-4-yl)-methyl-amide |
| 75 | 2,5-Dichloro-thiophene-3-sulfonic acid (1-{2-[3-(2,6-dimethyl-pyridin-4-yl)-ureido]-ethyl}-piperidin-4-yl)-methyl-amide |
| 76 | N-(1-{2-[3-(2,6-Dimethyl-pyridin-4-yl)-ureido]-ethyl}-piperidin-4-yl)-N-ethyl-benzenesulfonamide |
| 77 | N-(1-{2-[3-(2,6-Dimethyl-pyridin-4-yl)-ureido]-ethyl}-piperidin-4-yl)-N-ethyl-3-fluoro-benzenesulfonamide |
| 78 | N-(1-{2-[3-(2,6-Dimethyl-pyridin-4-yl)-ureido]-ethyl}-piperidin-4-yl)-N-ethyl-2-fluoro-benzenesulfonamide |
| 79 | N-(1-{2-[3-(2,6-Dimethyl-pyridin-4-yl)-ureido]-ethyl}-piperidin-4-yl)-N-ethyl-2,4-difluoro-benzenesulfonamide |
| 80 | N-(1-{2-[3-(2,6-Dimethyl-pyridin-4-yl)-ureido]-ethyl}-piperidin-4-yl)-N-ethyl-3,4-difluoro-benzenesulfonamide |
| 81 | N-(1-{2-[3-(2,6-Dimethyl-pyridin-4-yl)-ureido]-ethyl}-piperidin-4-yl)-N-ethyl-2,6-difluoro-benzenesulfonamide |
| 82 | N-(1-{2-[3-(2,6-Dimethyl-pyridin-4-yl)-ureido]-ethyl}-piperidin-4-yl)-4,N-diethyl-benzenesulfonamide |
| 83 | N-(1-{2-[3-(2,6-Dimethyl-pyridin-4-yl)-ureido]-ethyl}-piperidin-4-yl)-N-ethyl-4-isopropoxy-benzenesulfonamide |
| 84 | N-(1-{2-[3-(2,6-Dimethyl-pyridin-4-yl)-ureido]-ethyl}-piperidin-4-yl)-N-ethyl-4-methyl-benzenesulfonamide |
| 85 | N-(1-{2-[3-(2,6-Dimethyl-pyridin-4-yl)-ureido]-ethyl}-piperidin-4-yl)-N-ethyl-3-methyl-benzenesulfonamide |
| 86 | N-(1-{2-[3-(2,6-Dimethyl-pyridin-4-yl)-ureido]-ethyl}-piperidin-4-yl)-N-ethyl-2-methyl-benzenesulfonamide |
| 87 | N-(1-{2-[3-(2,6-Dimethyl-pyridin-4-yl)-ureido]-ethyl}-piperidin-4-yl)-N-ethyl-4-methoxy-2,3,6-trimethyl-benzenesulfonamide |
| 88 | 4-Chloro-N-(1-{2-[3-(2,6-dimethyl-pyridin-4-yl)-ureido]-ethyl}-piperidin-4-yl)-N-ethyl-benzenesulfonamide |
| 89 | 3-Chloro-N-(1-{2-[3-(2,6-dimethyl-pyridin-4-yl)-ureido]-ethyl}-piperidin-4-yl)-N-ethyl-benzenesulfonamide |
| 90 | 2-Chloro-N-(1-{2-[3-(2,6-dimethyl-pyridin-4-yl)-ureido]-ethyl}-piperidin-4-yl)-N-ethyl-benzenesulfonamide |

-continued

Examples of particularly preferred compounds of General Formula 1 are selected from the group consisting of:

| Example number | |
|---|---|
| 91 | 3,4-Dichloro-N-(1-{2-[3-(2,6-dimethyl-pyridin-4-yl)-ureido]-ethyl}-piperidin-4-yl)-N-ethyl-benzenesulfonamide |
| 92 | N-(1-{2-[3-(2,6-Dimethyl-pyridin-4-yl)-ureido]-ethyl}-piperidin-4-yl)-N-ethyl-4-trifluoromethyl-benzenesulfonamide |
| 93 | N-(1-{2-[3-(2,6-Dimethyl-pyridin-4-yl)-ureido]-ethyl}-piperidin-4-yl)-N-ethyl-3-trifluoromethyl-benzenesulfonamide |
| 94 | N-(1-{2-[3-(2,6-Dimethyl-pyridin-4-yl)-ureido]-ethyl}-piperidin-4-yl)-N-ethyl-2-trifluoromethyl-benzenesulfonamide |
| 95 | Thiophene-2-sulfonic acid (1-{2-[3-(2,6-dimethyl-pyridin-4-yl)-ureido]-ethyl}-piperidin-4-yl)-ethyl-amide |
| 96 | 5-Chloro-thiophene-2-sulfonic acid (1-{2-[3-(2,6-dimethyl-pyridin-4-yl)-ureido]-ethyl}-piperidin-4-yl)-ethyl-amide |
| 97 | 2,5-Dichloro-thiophene-3-sulfonic acid (1-{2-[3-(2,6-dimethyl-pyridin-4-yl)-ureido]-ethyl}-piperidin-4-yl)-ethyl-amide |
| 98 | N-(1-{2-[3-(2,6-Dimethyl-pyridin-4-yl)-ureido]-ethyl}-piperidin-4-yl)-N-ethyl-2,5-dimethoxy-benzenesulfonamide |
| 99 | 5-Bromo-N-(1-{2-[3-(2,6-dimethyl-pyridin-4-yl)-ureido]-ethyl}-piperidin-4-yl)-N-ethyl-2-methoxy-benzenesulfonamide |
| 100 | N-(1-{2-[3-(2,6-Dimethyl-pyridin-4-yl)-ureido]-ethyl}-piperidin-4-yl)-N-ethyl-2-methoxy-4-methyl-benzenesulfonamide |
| 101 | N-(1-{2-[3-(2,6-Dimethyl-pyridin-4-yl)-ureido]-ethyl}-piperidin-4-yl)-N-ethyl-3,4-dimethoxy-benzenesulfonamide |
| 102 | N-(1-{2-[3-(2,6-Dimethyl-pyridin-4-yl)-ureido]-ethyl}-piperidin-4-yl)-N-ethyl-3-methoxy-benzenesulfonamide |
| 103 | N-Cyclopropyl-N-(1-{2-[3-(2,6-dimethyl-pyridin-4-yl)-ureido]-ethyl}-piperidin-4-yl)-benzenesulfonamide |
| 104 | N-Cyclopropyl-N-(1-{2-[3-(2,6-dimethyl-pyridin-4-yl)-ureido]-ethyl}-piperidin-4-yl)-3-fluoro-benzenesulfonamide |
| 106 | N-Cyclopropyl-N-(1-{2-[3-(2,6-dimethyl-pyridin-4-yl)-ureido]-ethyl}-piperidin-4-yl)-2,4-difluoro-benzenesulfonamide |
| 108 | N-Cyclopropyl-N-(1-{2-[3-(2,6-dimethyl-pyridin-4-yl)-ureido]-ethyl}-piperidin-4-yl)-2,6-difluoro-benzenesulfonamide |
| 109 | N-Cyclopropyl-N-(1-{2-[3-(2,6-dimethyl-pyridin-4-yl)-ureido]-ethyl}-piperidin-4-yl)-4-ethyl-benzenesulfonamide |
| 111 | N-Cyclopropyl-N-(1-{2-[3-(2,6-dimethyl-pyridin-4-yl)-ureido]-ethyl}-piperidin-4-yl)-4-isopropoxy-benzenesulfonamide |
| 112 | N-Cyclopropyl-N-(1-{2-[3-(2,6-dimethyl-pyridin-4-yl)-ureido]-ethyl}-piperidin-4-yl)-4-methyl-benzenesulfonamide |
| 113 | N-Cyclopropyl-N-(1-{2-[3-(2,6-dimethyl-pyridin-4-yl)-ureido]-ethyl}-piperidin-4-yl)-3-methyl-benzenesulfonamide |
| 115 | 4-Chloro-N-cyclopropyl-N-(1-{2-[3-(2,6-dimethyl-pyridin-4-yl)-ureido]-ethyl}-piperidin-4-yl)-benzenesulfonamide |
| 116 | 3-Chloro-N-cyclopropyl-N-(1-{2-[3-(2,6-dimethyl-pyridin-4-yl)-ureido]-ethyl}-piperidin-4-yl)-benzenesulfonamide |
| 117 | 2-Chloro-N-cyclopropyl-N-(1-{2-[3-(2,6-dimethyl-pyridin-4-yl)-ureido]-ethyl}-piperidin-4-yl)-benzenesulfonamide |
| 118 | 3,4-Dichloro-N-cyclopropyl-N-(1-{2-[3-(2,6-dimethyl-pyridin-4-yl)-ureido]-ethyl}-piperidin-4-yl)-benzenesulfonamide |
| 119 | N-Cyclopropyl-N-(1-{2-[3-(2,6-dimethyl-pyridin-4-yl)-ureido]-ethyl}-piperidin-4-yl)-4-trifluoromethyl-benzenesulfonamide |
| 120 | N-Cyclopropyl-N-(1-{2-[3-(2,6-dimethyl-pyridin-4-yl)-ureido]-ethyl}-piperidin-4-yl)-3-trifluoromethyl-benzenesulfonamide |
| 123 | 5-Chloro-thiophene-2-sulfonic acid cyclopropyl-(1-{2-[3-(2,6-dimethyl-pyridin-4-yl)-ureido]-ethyl}-piperidin-4-yl)-amide |
| 124 | 2,5-Dichloro-thiophene-3-sulfonic acid cyclopropyl-(1-{2-[3-(2,6-dimethyl-pyridin-4-yl)-ureido]-ethyl}-piperidin-4-yl)-amide |
| 125 | N-Cyclopropyl-N-(1-{2-[3-(2,6-dimethyl-pyridin-4-yl)-ureido]-ethyl}-piperidin-4-yl)-4-methoxy-benzenesulfonamide |
| 126 | N-Cyclopropyl-N-(1-{2-[3-(2,6-dimethyl-pyridin-4-yl)-ureido]-ethyl}-piperidin-4-yl)-3-methoxy-benzenesulfonamide |
| 127 | N-Cyclopropyl-N-(1-{2-[3-(2,6-dimethyl-pyridin-4-yl)-ureido]-ethyl}-piperidin-4-yl)-2,5-dimethoxy-benzenesulfonamide |
| 128 | N-Cyclopropyl-N-(1-{2-[3-(2,6-dimethyl-pyridin-4-yl)-ureido]-ethyl}-piperidin-4-yl)-2-methoxy-4-methyl-benzenesulfonamide |
| 129 | N-Ethyl-N-(1-{2-[3-(2-ethyl-6-methyl-pyridin-4-yl)-ureido]-ethyl}-piperidin-4-yl)-2-methoxy-4-methyl-benzenesulfonamide |
| 130 | N-Ethyl-N-(1-{2-[3-(2-ethyl-6-methyl-pyridin-4-yl)-ureido]-ethyl}-piperidin-4-yl)-3,4-dimethoxy-benzenesulfonamide |
| 131 | N-Ethyl-N-(1-{2-[3-(2-ethyl-6-methyl-pyridin-4-yl)-ureido]-ethyl}-piperidin-4-yl)-3-methoxy-benzenesulfonamide |
| 135 | 1-(4-Chloro-phenyl)-cyclopropanecarboxylic acid (1-{2-[3-(2,6-dimethyl-pyridin-4-yl)-ureido]-ethyl}-piperidin-4-yl)-methyl-amide |

-continued

Examples of particularly preferred compounds of General Formula 1 are selected from the group consisting of:

| Example number | |
|---|---|
| 144 | 2-(4-Chloro-phenyl)-N-ethyl-N-(1-{2-[3-(2-ethyl-6-methyl-pyridin-4-yl)-ureido]-ethyl}-piperidin-4-yl)-isobutyramide |
| 146 | 2-(3,4-Dichloro-phenyl)-N-(1-{2-[3-(2,6-dimethyl-pyridin-4-yl)-ureido]-ethyl}-piperidin-4-yl)-N-ethyl-acetamide |
| 148 | 2-(4-Chloro-phenyl)-N-(1-{2-[3-(2,6-dimethyl-pyridin-4-yl)-ureido]-ethyl}-piperidin-4-yl)-N-ethyl-isobutyramide |
| 150 | 1-(4-Chloro-phenyl)-cyclopropanecarboxylic acid (1-{2-[3-(2,6-dimethyl-pyridin-4-yl)-ureido]-ethyl}-piperidin-4-yl)-ethyl-amide |
| 163 | 1-Phenyl-cyclopropanecarboxylic acid ethyl-(1-{2-[3-(2-ethyl-6-methyl-pyridin-4-yl)-ureido]-ethyl}-piperidin-4-yl)-amide |
| 164 | 1-(4-Chloro-phenyl)-cyclopropanecarboxylic acid ethyl-(1-{2-[3-(2-ethyl-6-methyl-pyridin-4-yl)-ureido]-ethyl}-piperidin-4-yl)-amide |
| 167 | 2-(4-Chloro-phenyl)-N-ethyl-N-(1-{2-[3-(2-ethyl-6-methyl-pyridin-4-yl)-ureido]-ethyl}-piperidin-4-yl)-acetamide |
| 168 | 2-(4-Chloro-phenyl)-N-cyclopropyl-N-(1-{2-[3-(2,6-dimethyl-pyridin-4-yl)-ureido]-ethyl}-piperidin-4-yl)-isobutyramide |
| 170 | 2-(4-Chloro-phenyl)-N-cyclopropyl-N-(1-{2-[3-(2,6-dimethyl-pyridin-4-yl)-ureido]-ethyl}-piperidin-4-yl)-acetamide |
| 171 | 1-(4-Chloro-phenyl)-cyclopropanecarboxylic acid cyclopropyl-(1-{2-[3-(2,6-dimethyl-pyridin-4-yl)-ureido]-ethyl}-piperidin-4-yl)-amide |
| 172 | 1-Phenyl-cyclopropanecarboxylic acid cyclopropyl-(1-{2-[3-(2,6-dimethyl-pyridin-4-yl)-ureido]-ethyl}-piperidin-4-yl)-amide |
| 173 | N-(1-{2-[3-(2,6-Dimethyl-pyridin-4-yl)-ureido]-ethyl}-piperidin-4-yl)-N-ethyl-2-methoxy-benzenesulfonamide |
| 9 | N-Cyclopropyl-N-(1-{2-[3-(2,6-dimethyl-pyridin-4-yl)-ureido]-ethyl}-piperidin-4-yl)-2-(4-methoxy-phenyl)-acetamide |
| 13 | 4-Ethyl-1-{2-[3-(2-ethyl-6-methyl-pyridin-4-yl)-ureido]-ethyl}-piperidine-4-carboxylic acid benzyl-(2-hydroxy-ethyl)-amide |
| 29 | 1-[2-(4-Benzyl-4-hydroxy-piperidin-1-yl)-ethyl]-3-(2-ethyl-6-methyl-pyridin-4-yl)-urea |
| 32 | 1-[2-(4-Benzyl-4-hydroxy-piperidin-1-yl)-ethyl]-3-(2,6-diethyl-pyridin-4-yl)-urea |
| 48 | N-(1-{2-[3-(2,6-Dimethyl-pyridin-4-yl)-ureido]-ethyl}-piperidin-4-yl)-N-methyl-benzenesulfonamide |
| 50 | N-(1-{2-[3-(2,6-Dimethyl-pyridin-4-yl)-ureido]-ethyl}-piperidin-4-yl)-3-methoxy-N-methyl-benzenesulfonamide |
| 52 | N-(1-{2-[3-(2,6-Dimethyl-pyridin-4-yl)-ureido]-ethyl}-piperidin-4-yl)-3,4-dimethoxy-N-methyl-benzenesulfonamide |
| 53 | N-(1-{2-[3-(2,6-Dimethyl-pyridin-4-yl)-ureido]-ethyl}-piperidin-4-yl)-2-methoxy-4,N-dimethyl-benzenesulfonamide |
| 54 | N-(1-{2-[3-(2,6-Dimethyl-pyridin-4-yl)-ureido]-ethyl}-piperidin-4-yl)-4-fluoro-N-methyl-benzenesulfonamide |
| 55 | N-(1-{2-[3-(2,6-Dimethyl-pyridin-4-yl)-ureido]-ethyl}-piperidin-4-yl)-3-fluoro-N-methyl-benzenesulfonamide |
| 56 | N-(1-{2-[3-(2,6-Dimethyl-pyridin-4-yl)-ureido]-ethyl}-piperidin-4-yl)-2-fluoro-N-methyl-benzenesulfonamide |
| 57 | N-(1-{2-[3-(2,6-Dimethyl-pyridin-4-yl)-ureido]-ethyl}-piperidin-4-yl)-2,4-difluoro-N-methyl-benzenesulfonamide |
| 58 | N-(1-{2-[3-(2,6-Dimethyl-pyridin-4-yl)-ureido]-ethyl}-piperidin-4-yl)-3,4-difluoro-N-methyl-benzenesulfonamide |
| 59 | N-(1-{2-[3-(2,6-Dimethyl-pyridin-4-yl)-ureido]-ethyl}-piperidin-4-yl)-2,6-difluoro-N-methyl-benzenesulfonamide |
| 64 | N-(1-{2-[3-(2,6-Dimethyl-pyridin-4-yl)-ureido]-ethyl}-piperidin-4-yl)-3,N-dimethyl-benzenesulfonamide |
| 65 | N-(1-{2-[3-(2,6-Dimethyl-pyridin-4-yl)-ureido]-ethyl}-piperidin-4-yl)-2,N-dimethyl-benzenesulfonamide |
| 66 | N-(1-{2-[3-(2,6-Dimethyl-pyridin-4-yl)-ureido]-ethyl}-piperidin-4-yl)-4-methoxy-2,3,6,N-tetramethyl-benzenesulfonamide |
| 68 | 3-Chloro-N-(1-{2-[3-(2,6-dimethyl-pyridin-4-yl)-ureido]-ethyl}-piperidin-4-yl)-N-methyl-benzenesulfonamide |
| 69 | 2-Chloro-N-(1-{2-[3-(2,6-dimethyl-pyridin-4-yl)-ureido]-ethyl}-piperidin-4-yl)-N-methyl-benzenesulfonamide |
| 72 | N-(1-{2-[3-(2,6-Dimethyl-pyridin-4-yl)-ureido]-ethyl}-piperidin-4-yl)-N-methyl-3-trifluoromethyl-benzenesulfonamide |
| 73 | Thiophene-2-sulfonic acid (1-{2-[3-(2,6-dimethyl-pyridin-4-yl)-ureido]-ethyl}-piperidin-4-yl)-methyl-amide |
| 105 | N-Cyclopropyl-N-(1-{2-[3-(2,6-dimethyl-pyridin-4-yl)-ureido]-ethyl}-piperidin-4-yl)-2-fluoro-benzenesulfonamide |
| 107 | N-Cyclopropyl-N-(1-{2-[3-(2,6-dimethyl-pyridin-4-yl)-ureido]-ethyl}-piperidin-4-yl)-3,4-difluoro-benzenesulfonamide |
| 114 | N-Cyclopropyl-N-(1-{2-[3-(2,6-dimethyl-pyridin-4-yl)-ureido]-ethyl}-piperidin-4-yl)-2-methyl-benzenesulfonamide |

-continued

Examples of particularly preferred compounds of General Formula 1 are selected from the group consisting of:

| Example number | |
|---|---|
| 121 | N-Cyclopropyl-N-(1-{2-[3-(2,6-dimethyl-pyridin-4-yl)-ureido]-ethyl}-piperidin-4-yl)-2-trifluoromethyl-benzenesulfonamide |
| 122 | Thiophene-2-sulfonic acid cyclopropyl-(1-{2-[3-(2,6-dimethyl-pyridin-4-yl)-ureido]-ethyl}-piperidin-4-yl)-amide |
| 132 | 2-(3,4-Dichloro-phenyl)-N-(1-{2-[3-(2,6-dimethyl-pyridin-4-yl)-ureido]-ethyl}-piperidin-4-yl)-N-methyl-acetamide |
| 134 | 1-Phenyl-cyclopropanecarboxylic acid (1-{2-[3-(2,6-dimethyl-pyridin-4-yl)-ureido]-ethyl}-piperidin-4-yl)-methyl-amide |
| 136 | 1-(4-Methoxy-phenyl)-cyclopropanecarboxylic acid (1-{2-[3-(2,6-dimethyl-pyridin-4-yl)-ureido]-ethyl}-piperidin-4-yl)-methyl-amide |
| 138 | 2-(4-Chloro-phenyl)-N-(1-{2-[3-(2,6-dimethyl-pyridin-4-yl)-ureido]-ethyl}-piperidin-4-yl)-N-methyl-acetamide |
| 139 | N-(1-{2-[3-(2,6-Dimethyl-pyridin-4-yl)-ureido]-ethyl}-piperidin-4-yl)-2-(4-fluoro-phenyl)-N-methyl-acetamide |
| 140 | N-(1-{2-[3-(2,6-Dimethyl-pyridin-4-yl)-ureido]-ethyl}-piperidin-4-yl)-N-methyl-2-phenyl-acetamide |
| 142 | 2-(3-Chloro-phenyl)-N-(1-{2-[3-(2,6-dimethyl-pyridin-4-yl)-ureido]-ethyl}-piperidin-4-yl)-N-methyl-acetamide |
| 145 | 2-(2-Chloro-phenyl)-N-(1-{2-[3-(2,6-dimethyl-pyridin-4-yl)-ureido]-ethyl}-piperidin-4-yl)-N-ethyl-acetamide |
| 147 | N-(1-{2-[3-(2,6-Dimethyl-pyridin-4-yl)-ureido]-ethyl}-piperidin-4-yl)-N-ethyl-2-(2-methoxy-phenyl)-acetamide |
| 149 | 1-Phenyl-cyclopropanecarboxylic acid (1-{2-[3-(2,6-dimethyl-pyridin-4-yl)-ureido]-ethyl}-piperidin-4-yl)-ethyl-amide |
| 151 | 1-(4-Methoxy-phenyl)-cyclopropanecarboxylic acid (1-{2-[3-(2,6-dimethyl-pyridin-4-yl)-ureido]ethyl}-piperidin-4-yl)-ethyl-amide |
| 152 | N-(1-{2-[3-(2,6-Dimethyl-pyridin-4-yl)-ureido]-ethyl}-piperidin-4-yl)-N-ethyl-2-phenyl-acetamide |
| 153 | N-(1-{2-[3-(2,6-Dimethyl-pyridin-4-yl)-ureido]-ethyl}-piperidin-4-yl)-N-ethyl-2-(4-methoxy-phenyl)-acetamide |
| 154 | N-(1-{2-[3-(2,6-Dimethyl-pyridin-4-yl)-ureido]-ethyl}-piperidin-4-yl)-N-ethyl-4-methoxy-benzamide |
| 155 | N-(1-{2-[3-(2,6-Dimethyl-pyridin-4-yl)-ureido]-ethyl}-piperidin-4-yl)-N-ethyl-3,4-dimethoxy-benzamide |
| 156 | N-(1-{2-[3-(2,6-Dimethyl-pyridin-4-yl)-ureido]-ethyl}-piperidin-4-yl)-N-ethyl-4-fluoro-benzamide |
| 157 | N-(1-{2-[3-(2,6-Dimethyl-pyridin-4-yl)-ureido]-ethyl}-piperidin-4-yl)-N-ethyl-2-(3-methoxy-phenyl)-acetamide |
| 158 | 2-(3,4-Dimethoxy-phenyl)-N-(1-{2-[3-(2,6-dimethyl-pyridin-4-yl)-ureido]-ethyl}-piperidin-4-yl)-N-ethyl-acetamide |
| 160 | N-(1-{2-[3-(2,6-Dimethyl-pyridin-4-yl)-ureido]-ethyl}-piperidin-4-yl)-N-ethyl-2-thiophen-2-yl-acetamide |
| 161 | N-(1-{2-[3-(2,6-Dimethyl-pyridin-4-yl)-ureido]-ethyl}-piperidin-4-yl)-N-ethyl-2-(4-fluoro-phenyl)-acetamide |
| 162 | N-(1-{2-[3-(2,6-Dimethyl-pyridin-4-yl)-ureido]-ethyl}-piperidin-4-yl)-N-ethyl-benzamide |
| 165 | 1-(4-Methoxy-phenyl)-cyclopropanecarboxylic acid ethyl-(1-{2-[3-(2-ethyl-6-methyl-pyridin-4-yl)-ureido]-ethyl}-piperidin-4-yl)-amide |
| 166 | N-Ethyl-N-(1-{2-[3-(2-ethyl-6-methyl-pyridin-4-yl)-ureido]-ethyl}-piperidin-4-yl)-2-phenyl-acetamide |
| 169 | 1-(4-Methoxy-phenyl)-cyclopropanecarboxylic acid cyclopropyl-(1-{2-[3-(2,6-dimethyl-pyridin-4-yl)-ureido]-ethyl}-piperidin-4-yl)-amide |

Because of their ability to inhibit the actions of urotensin II, the described compounds can be used for treatment of diseases which are associated with an increase in vasoconstriction, proliferation or other disease states associated with the actions of urotensin II. Examples of such diseases are hypertension, atherosclerosis, angina or myocardial ischemia, congestive heart failure, cardiac insufficiency, cardiac arrhythmias, renal ischemia, chronic kidney disease, renal failure, stroke, cerebral vasospasm, cerebral ischemia, dementia, migraine, subarachnoidal hemorrhage, diabetes, diabetic arteriopathy, diabetic nephropathy, connective tissue diseases, cirrhosis, chronic obstructive pulmonary disease, high-altitude pulmonary edema, Raynaud's syndrome, portal hypertension, thyroid dysfunction, pulmonary edema, pulmonary hypertension, or pulmonary fibrosis. They can also be used for prevention of restenosis after balloon or stent angioplasty, for the treatment of cancer, prostatic hypertrophy, erectile dysfunction, hearing loss, amaurosis, chronic bronchitis, asthma, gram negative septicemia, shock, sickle cell anemia, sickle cell acute chest syndrome, glomerulonephritis, renal colic, glaucoma, therapy and prophylaxis of diabetic complications, complications of vascular or cardiac surgery or after organ transplantation, complications of cyclosporin treatment, pain, addiction, schizophrenia, Alzheimer's disease, anxiety, obsessive-compulsive behavior, epileptic seizures, stress, depression, dementias, neuromuscular disorders, neurodegenerative diseases, as well as other diseases related to a dysregulation of urotensin II or urotensin II receptors.

These compositions may be administered in enteral or oral form e.g. as tablets, dragees, gelatine capsules, emulsions, solutions or suspensions, in nasal form like sprays and aerosols, or rectally in form of suppositories. These compounds may also be administered in intramuscular, parenteral or intravenous form, e.g. in form of injectable solutions.

These pharmaceutical compositions may contain the compounds of formula 1 as well as their pharmaceutically acceptable salts in combination with inorganic and/or organic excipients, which are usual in the pharmaceutical industry, like lactose, maize or derivatives thereof, talcum, stearic acid or salts of these materials.

For gelatine capsules vegetable oils, waxes, fats, liquid or half-liquid polyols etc. may be used. For the preparation of solutions and syrups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, anti-oxidants etc.

The compounds of General Formula 1 may also be used in combination with one or more other therapeutically useful substances e.g. α- and β-blockers like phentolamine, phenoxybenzamine, atenolol, propranolol, timolol, metoprolol, carteolol, carvedilol, etc.; with vasodilators like hydralazine, minoxidil, diazoxide, flosequinan, etc.; with calcium-antagonists like diltiazem, nicardipine, nimodipine, verapamil, nifedipine, etc.; with angiotensin converting enzyme-inhibitors like cilazapril, captopril, enalapril, lisinopril etc.; with potassium channel activators like pinacidil, chromakalim, etc.; with angiotensin receptor antagonists like losartan, valsartan, candesartan, irbesartan, eprosartan, telmisartan, and tasosartan, etc.; with diuretics like hydrochlorothiazide, chlorothiazide, acetolamide, bumetanide, furosemide, metolazone, chlortalidone, etc.; with sympatholytics like methyldopa, clonidine, guanabenz, reserpine, etc.; with endothelin receptor antagonists like bosentan, tezosentan, darusentan, atrasentan, enrasentan, or sitaxsentan, etc.; with anti-hyperlipidemic agents like lovastatin, pravistatin, fluvastatin, atorvastatin, cerivastatin, simvastatin, etc.; and other therapeutics which serve to treat high blood pressure, vascular disease or other disorders listed above.

The dosage may vary within wide limits but should be adapted to the specific situation. In general the dosage given daily in oral form should be between about 3 mg and about 3 g, preferably between about 5 mg and about 1 g, especially preferred between 10 mg and 300 mg, per adult with a body weight of about 70 kg. The dosage should be administered preferably in 1 to 3 doses of equal weight per day. As usual children should receive lower doses which are adapted to body weight and age.

GENERAL PREPARATION OF COMPOUNDS OF THE INVENTION

Compounds of the General Formula 1 can be prepared using methods generally known in the art, according to the general sequence of reactions outlined below. For simplicity and clarity reasons sometimes only a few of the possible synthetic routes that lead to compounds of General Formula 1 are described.

For the synthesis of compounds of General Formula 1 general synthetic routes illustrated in schemes A through G can be employed. The generic groups Py, $R^1$, $R^2$, $R^3$, $R^4$, $R^5$, $R^6$, $R^7$, $R^8$, X, Y, Z, n, and m employed in schemes A through G have the definitions given in General Formula 1 above. Other abbreviations used are defined in the experimental section. Some instances of the generic groups X and Z might be incompatible with the assembly illustrated in schemes A through G and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as are necessary are in place.

Preparation of compounds of General Formula 1. These compounds are prepared according to scheme A.

Achiral, racemic or enantiomerically pure amines of general structure I in scheme A are reacted with isocyanates of general structure II to provide compounds of General Formula 1. Alternatively, amines of general structure I are reacted with ureas of general structure III to provide compounds of General Formula 1. Alternatively, amines of general structure I are reacted with pentafluorophenyl-carbamates of general structure IV to provide compounds of General Formula 1. The preparation of isocyanates of general structure II, of ureas of general structure III and of pentafluorophenyl-carbamates of general structure IV is described in scheme E below. The preparation of amines of general structure I is described in scheme G below.

Scheme A

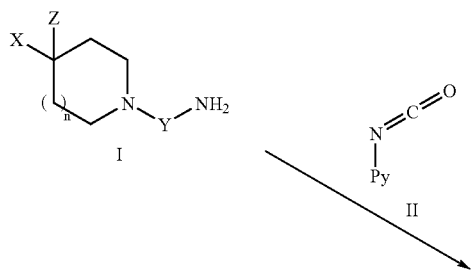

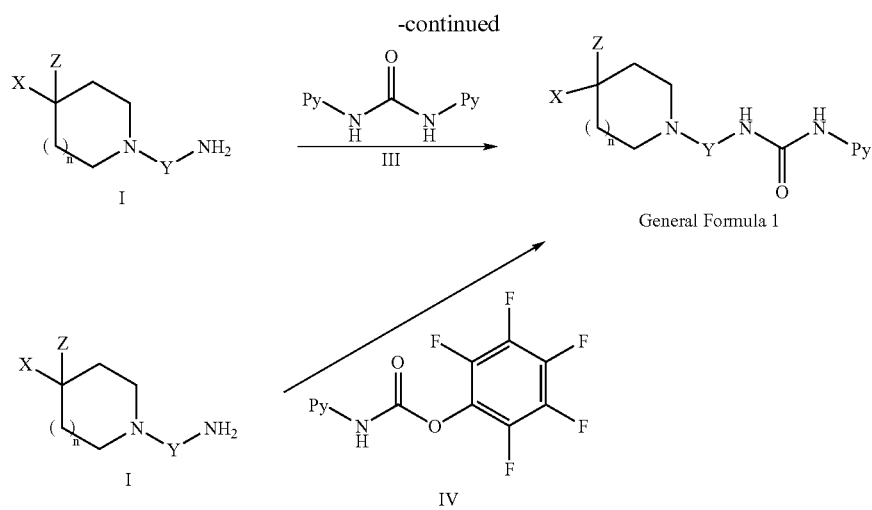

Preparation of compounds of General Formula 1 wherein Y is —$(CH_2)_m C(R^6)(R^7)$—. Compounds of General Formula 1 wherein Y is —$(CH_2)_m C(R^6)(R^7)$— are prepared according to scheme B.

Achiral, racemic or optically active 4-substituted-piperidines and 3-substituted-pyrrolidines of general structure V in scheme B are either commercially available or prepared by methods well known in the art. Ureido acetic- and propionic acid derivatives of general structure VI in scheme B are prepared according to scheme F below. N-Acylation of piperidines and pyrrolidines of general structure V with ureido acetic- and propionic acid derivatives of general structure VI is accomplished in a polar solvent such as DMF in the presence of a small stoichiometric excess of a coupling reagent such as a EDC to provide amides of general structure VII. Selective reduction of the amide carbonyl group with a reagent such as $LiAlH_4$ in a aprotic solvent such as THF provides the target compounds of General Formula 1 wherein Y is —$(CH_2)_m C(R^6)(R^7)$—.

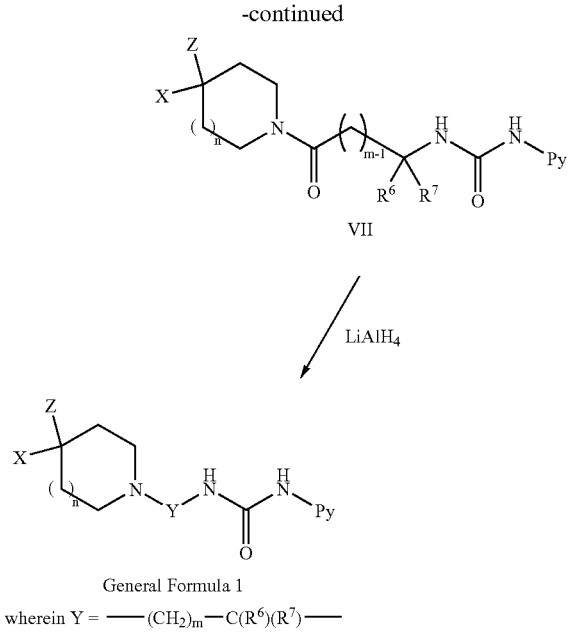

Compounds of General Formula 1 wherein $R^6$ and $R^7$ are H. These compounds are alternatively prepared according to the method illustrated in scheme C.

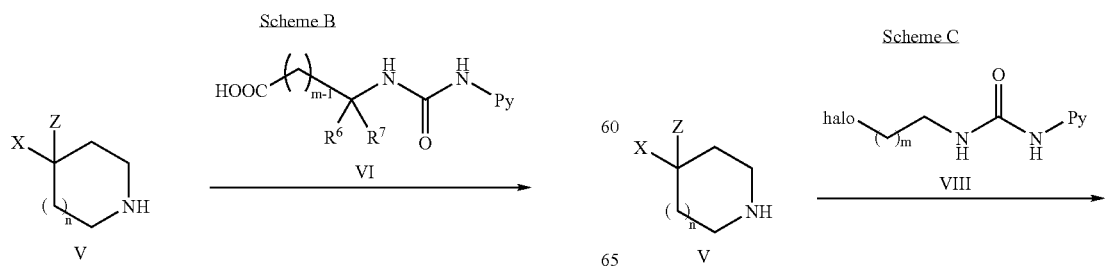

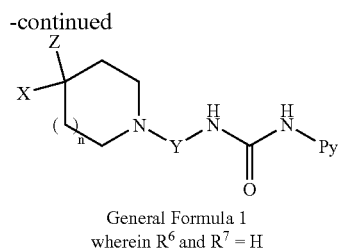

General Formula 1
wherein R⁶ and R⁷ = H

Achiral, racemic or optically active 4-substituted-piperidines and 3-substituted-pyrrolidines of general structure V in scheme C are either commercially available or prepared by methods well known in the art. Haloalkyl ureas of general structure VIII in scheme C are prepared according to scheme E below. N-Alkylation of piperidines and pyrrolidines of general structure V with haloalkyl ureas of general structure VIII is accomplished in a polar solvent such as tetrahydrofuran in the presence of a sub-stoichiometric amount of an iodide salt such as NaI and a small stoichiometric excess of acid scavenger such as NaHCO₃ to provide the target compounds of General Formula 1.

Compounds of General Formula 1 wherein X represents R¹—SO₂NR²—, R¹—CONR²—, aryl-R⁸—CONR²— or R¹—NR²CONR³— and Z, R⁶ and R⁷ represent H. These compounds are alternatively prepared according to the method illustrated in scheme D.

Achiral, racemic or optically active carbamates of general structure IX in scheme D are either commercially available or readily prepared by methods well known in the art. Haloalkyl ureas of general structure VIII are prepared according to Scheme E below. Carbamates of general structure IX are reacted with haloalkyl ureas of general structure VIII in a polar solvent such as tetrahydrofuran in the presence of a substoichiometric amount of an iodide salt such as NaI and a small stoichiometric excess of an acid scavenger such as NaHCO₃, followed by removal of the carbamate group under acidic conditions, such as reaction with HCl in dioxane or TFA in CH₂Cl₂.

The resulting compounds of general structure X in scheme D are converted to compounds of General Formula 1 wherein X represents R¹—SO₂NR²—, R¹—CONR²—, aryl-R⁸—CONR²— or R¹—NR²CONR³— and Z, R⁶ and R⁷ represent H, by reaction with commercially available or well known sulfonylchlorides, isocyanates, or acid chlorides. Compounds of General Formula 1 wherein X represents R¹—NR³CONR²—, R³ represents C₁₋₇-alkyl or aryl-C₁₋₇-alkyl, and Z, R⁶ and R⁷ represent H, are prepared by reaction of compounds of general structure X with secondary amines that are commercially available or prepared by methods well known in the art in the presence of a stoichiometric amount of a coupling reagent such as carbonyldiimidazole (CDI).

Scheme D

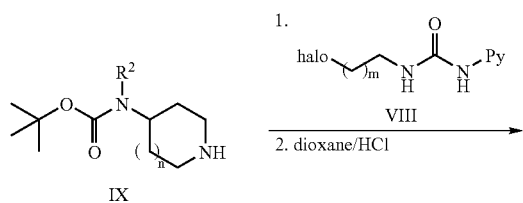

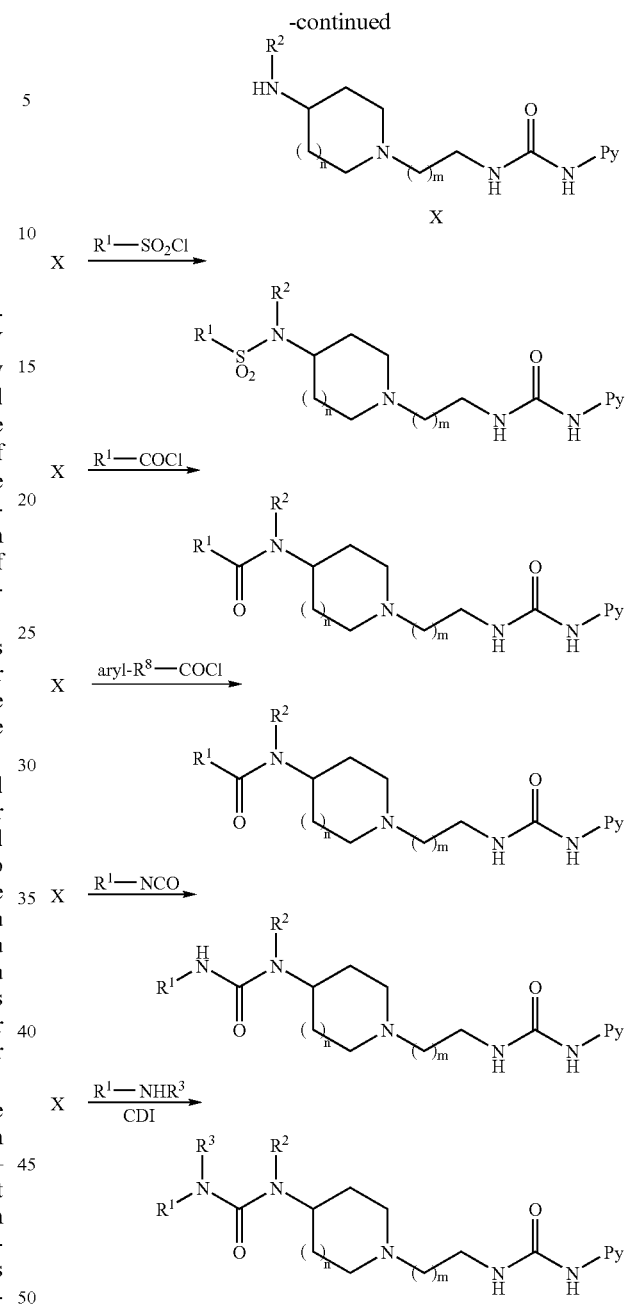

Synthetic intermediates used in Schemes A, B, C, and D. Synthetic intermediates containing the group Py, as defined in the General Formula 1 above, are obtained by the methods illustrated in Schemes E and F.

Carboxylic acids of general structure XI in scheme E are commercially available or are prepared by well known methods. Reaction with diphenylphosphorylazide provides the acyl azide, which undergoes Curtius rearrangement to provide the isocyanates of general structure II, which are used in situ. 4-Aminopyridines of general structure XII are commercially available or prepared by methods well known in the art (see for example "A Convenient Preparation of 4-Pyridinamine Derivatives, M. Malinowski, L. Kaczmarek, J. Prakt. Chem. (1988) 330, 154-158). Reaction of 4-aminopyridines of general structure XII with isocyanates of general structure II provides ureas of general structure II. Alternatively, ureas of general structure III are prepared by reaction of 4-aminopyridines of general structure XII and a coupling reagent such as CDI in a aprotic solvent such as THF at reflux. Alternatively, pentafluorophenyl-carbamates of general structure IV are prepared by reaction of 4-aminopyridines of general structure XII and di(pentafluorophenyl)carbonate in a aprotic solvent such as THF at room temperature. Isocyanates of general structure II, reacted with halopropylamine hydrochloride or haloethylamine hydrochloride in the presence of an acid scavenger such as DIPEA, provide ureas of general structure VIII. Alternatively, reaction of 4-aminopyridines of general structure XII with chloroethylisocyanate or chloropropylisocyanate in a polar aprotic solvent such as tetrahydrofuran provides the ureas of general structure VIII.

Scheme E

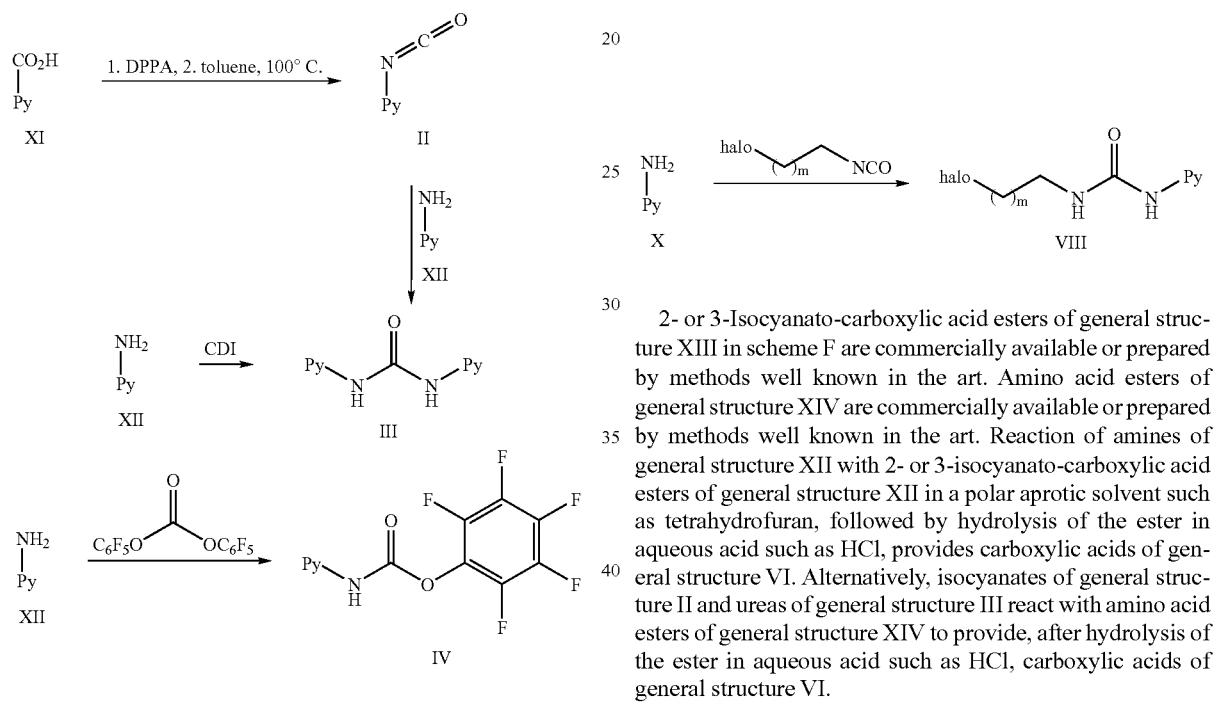

2- or 3-Isocyanato-carboxylic acid esters of general structure XIII in scheme F are commercially available or prepared by methods well known in the art. Amino acid esters of general structure XIV are commercially available or prepared by methods well known in the art. Reaction of amines of general structure XII with 2- or 3-isocyanato-carboxylic acid esters of general structure XII in a polar aprotic solvent such as tetrahydrofuran, followed by hydrolysis of the ester in aqueous acid such as HCl, provides carboxylic acids of general structure VI. Alternatively, isocyanates of general structure II and ureas of general structure III react with amino acid esters of general structure XIV to provide, after hydrolysis of the ester in aqueous acid such as HCl, carboxylic acids of general structure VI.

Scheme F

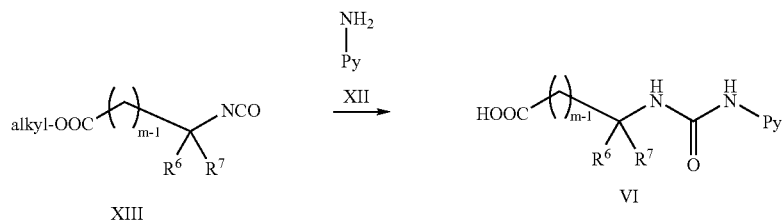

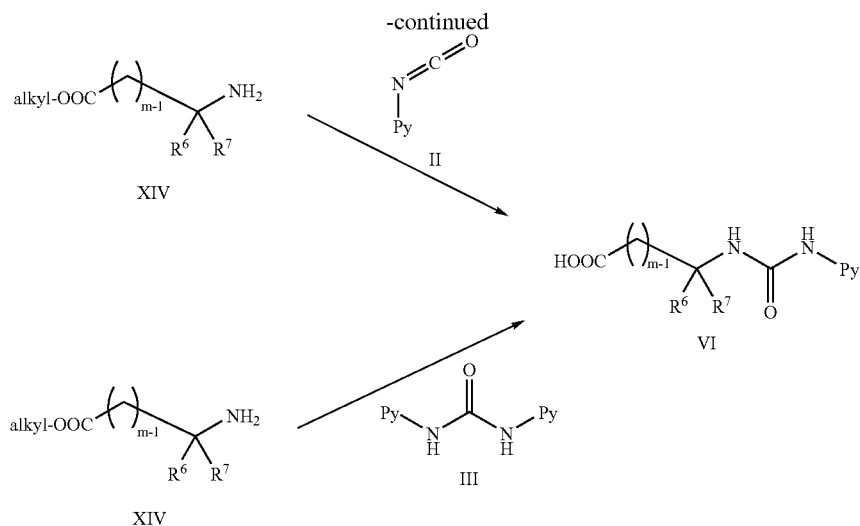

Synthetic intermediates of general structure I are obtained by the methods illustrated in Scheme G.

Achiral, racemic or optically active 4-substituted-piperidines and 3-substituted-pyrrolidines of general structure V in scheme G are either commercially available or prepared by methods well known in the art. Ketones and aldehydes of general structure XVI are commercially available or are prepared by methods well-known in the art. Reaction of ketones and aldehydes of general structure XVI with 4-substituted-piperidines and 3-substituted-pyrrolidines of general structure V in presence of a cyanide ion donor such as acetone cyanohydrine provides piperidine and pyrrolidine derivatives of general structure XVII.

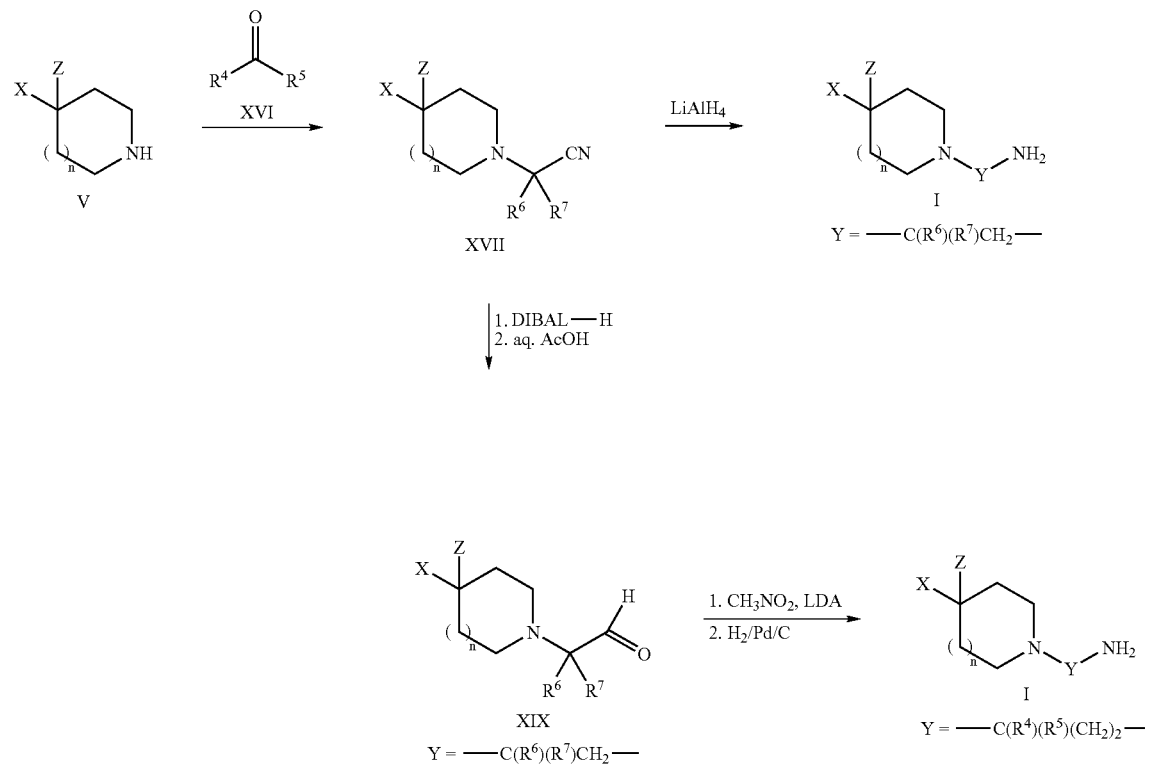

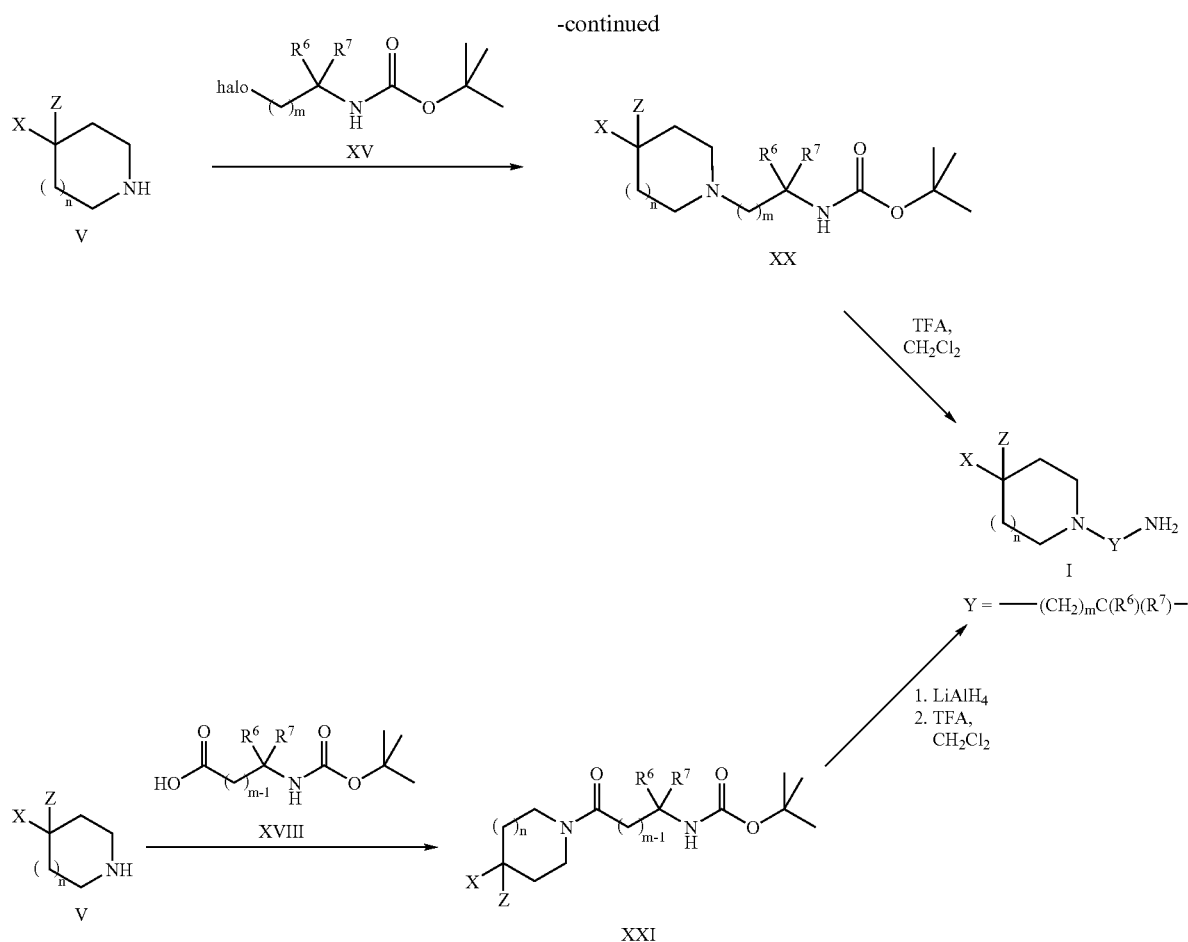

Alternatively, in case $R^6$ and $R^7$ represent H, compounds of general structure XVII are obtained by alkylation of compounds of general structure V with commercially available haloacetonitrile or 3-halopropionitrile in presence of a small stoichiometric excess of acid scavenger such as DIPEA. Complete reduction of the cyano group with a reducing reagent such as $LiAlH_4$ in a polar aprotic solvent such as THF provides the intermediate primary amines of general structure 1, wherein Y is —$C(R^6)(R^7)$—$CH_2$—. Partial reduction of the cyano group of compounds of general structure XVII with a reducing reagent such as DIBAL-H, followed by aqueous hydrolysis provides aldehydes of general structure XIX. Condensation with the nitromethane anion and subsequent reduction, for example by catalytic hydrogenation, provides the intermediate primary amines of general structure 1, wherein Y is —$C(R^6)(R^7)(CH_2)_2$—. Haloalkyl carbamates of general structure XV in Scheme G are commercially available or are prepared by methods well-known in the art. N-Alkylation of piperidines and pyrrolidines of general structure V with haloalkyl carbamates of general structure XV is accomplished in a polar solvent such as THF in the presence of a small stoichiometric excess of acid scavenger such as DIPEA to provide compounds of general structure XX. Cleavage of the resulting carbamate with methods well known in the art, for example with TFA in a solvent such as $CH_2Cl_2$, provides the intermediate primary amine derivatives of general structure I wherein Y is —$(CH_2)_mC(R^6)(R^7)$—. Protected amino acids of general structure XVIII are commercially available or are prepared by methods well-known in the art. N-Acylation of piperidines and pyrrolidines of general structure V with compounds of general structure XVIII is accomplished under well-known conditions, for example in a polar solvent such as DMF in the presence of a small stoichiometric excess of a coupling agent such as a carbodiimide, to provide compounds of general structure XXI. Reduction with a reagent such as $LiAlH_4$ and deprotection provides intermediate primary amines of general structure I wherein Y is —$(CH_2)_mC(R^6)(R^7)$—.

The foregoing general description of the invention will now be further illustrated with a number of non-limiting examples.

EXAMPLES OF THE INVENTION

List of Abbreviations

AcOH acetic acid
aq. aqueous
9-BBN 9-borabicyclo[3.3.1]nonane
BSA bovine serum albumin
cat. catalytic
CDI carbonyldiimidazole
DIBAL-H diisobutylaluminiumhydride
DIPEA diisopropylethylamine
DMAP 4-dimethylaminopyridine
DMF dimethylformamide DMSO dimethylsulfoxide
DPPA diphenylphosphorylazide
EDC N-(3-dimethylaminopropyl)-N'-ethyl-carbodiimide
EDTA ethylenediamine tetra-acetic acid
EtOAc ethyl acetate
Et$_2$O diethyl ether
FC flash chromatography
Fe(acac)$_3$ iron(III)-acetylacetonate
Hex hexane
HOBt 1-hydroxybenzotriazole
HPLC high performance liquid chromatography
h-UII human Urotensin II
HV high vacuum conditions
LC-MS liquid chromatography-mass spectroscopy
LiAlH$_4$ lithium aluminum hydride
MeOH methanol
min minutes
MHz megahertz
MPLC medium pressure liquid chromatography
NaBHAc$_3$ sodium triacetoxyborohydride
NMP N-methylpyrrolidone
NMR nuclear magnetic resonance
ppm part per million
PBS phosphate-buffered saline
Pd(dppf)Cl$_2$ 1,1'-bis(diphenylphosphino)ferrocene-palladium(II)dichloride dichloromethane complex
PG protecting group
r.t. room temperature
sat. saturated
SiO$_2$ silica gel
TEA triethylamine
TFA trifluoroacetic acid
THF tetrahydrofuran
TLC thin layer chromatography
t$_R$ retention time Reactions are routinely performed under an inert atmosphere such as N$_2$ gas in air dried glassware. Solvents are used as received from the vendor. Evaporations are performed in a rotary evaporator at reduced pressure and a water bath temperature of 50° C. LC-MS characterizations are performed on a Finnigan HP1100 platform using ESI ionization mode, and positive ion detection with a Navigator AQA detector. Analytical liquid chromatographic separations are performed on a C18 column of 4.6×30 mm dimensions and a mobile phase consisting of a 6 minute gradient of 2-95% CH$_3$CN in water containing 0.5% formic acid at a flow rate of 0.45 mL/min. Retention time (t$_R$) is given in min. TLC is performed on pre-coated silica gel 60 F$_{254}$ glass-backed plates (Merck). MPLC is performed on a Labomatic platform using either normal phase SiO$_2$-columns and a mobile phase consisting of heptane-EtOAc, or reversed phase C18 columns and a mobile phase consisting of water-MeOH. Preparative HPLC is performed on a Varian/Gilson platform using a C18 column of 21×60 mm dimensions and a mobile phase consisting of a gradient of 2-95% CH$_3$CN in water containing 0.5% formic acid.

Example A

Preparation of Intermediates

The following materials are commercially available.

| Example No | Example |
|---|---|
| A1. | 4-Benzylpiperidine |
| A2. | 4-Benzyl-piperidin-4-ol |
| A3. | 4-Benzyloxy-piperidine |

A4. N-Ethyl-4-methoxy-N-piperidin-4-yl-benzenesulfonamide

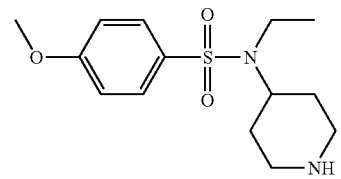

A4.1. 4-[Ethyl-(4-methoxy-benzenesulfonyl)-amino]-piperidine-1-carboxylic acid tert-butyl ester A mixture of commercially available 4-oxo-piperidine-1-carboxylic acid tert-butyl ester (5.58 g, 28 mmol) and ethylamine (2 M in THF, 50 mL, 100 mmol) in THF (100 mL) is stirred at r.t. for 2 h. NaBHAc$_3$ (8.9 g, 42 mmol) is added and the mixture is stirred for 15 h. The mixture is quenched with 1 M aq. NaOH (100 mL) and stirred at r.t. for 6 h. The mixture is extracted with CH$_2$Cl$_2$ (150 mL, then 4×50 mL) and the combined organic extracts are washed with 1 M aq. NaOH (30 mL). The organic phase is dried (Na$_2$SO$_4$), filtered and evaporated. The residue is dissolved in CH$_2$Cl$_2$ (100 mL) and TEA (3 g, 30 mmol) and, subsequently, a solution of 4-methoxy-benzenesulfonylchloride (6.38 g, 30.9 mmol) in CH$_2$Cl$_2$ (10 mL) are added at 0° C. The mixture is warmed to r.t. during 15 h and quenched with 1 M aq. NaOH (30 mL). The phases are separated and the organic phase is washed with 1 M aq. NaOH (30 mL), 1 M aq. KHSO$_4$ (2×30 mL) and sat. aq. NaCl (30 mL). The organic phase is dried (Na$_2$SO$_4$), filtered and evaporated. The residue is purified by FC (SiO$_2$, EtOAc-heptane) to provide the title compound.

A4.2. N-Ethyl-4-methoxy-N-piperidin-4-yl-benzenesulfonamide

A solution of 4-[ethyl-(4-methoxy-benzenesulfonyl)-amino]-piperidine-1-carboxylic acid tert-butyl ester (11.1 g, 28 mmol) in CH$_2$Cl$_2$ (50 mL) is cooled at 0° C. and TFA (40 mL) is added. The mixture is stirred at 0° C. for 0.5 h and then evaporated. The residue is dissolved in CH$_2$Cl$_2$ (50 mL) and 1 M aq. NaOH (50 mL) is added. The mixture is stirred for 15 h at r.t., then the phases are separated and the aq. phase is extracted with CH$_2$Cl$_2$ (4×30 mL). The combined org. phases are washed with 1 M aq. NaOH (2×30 mL), dried (Na$_2$SO$_4$), filtered and evaporated to provide the title compound.

The following intermediates are prepared from 4-oxo-piperidine-1-carboxylic acid tert-butyl ester, ethylamine, cyclopropylamine or n-propylamine, and commercially available arylsulfonylchlorides or arylacetyl chlorides using the method described in Example A4.

| Example No | Example |
|---|---|
| A4. | N-Ethyl-4-methoxy-N-piperidin-4-yl-benzenesulfonamide |
| A5. | N-Ethyl-4-fluoro-N-piperidin-4-yl-benzenesulfonamide |
| A6. | 4-Bromo-N-ethyl-N-piperidin-4-yl-benzenesulfonamide |
| A7. | 4-Methoxy-N-piperidin-4-yl-N-propyl-benzenesulfonamide |
| A8. | 4-Fluoro-N-piperidin-4-yl-N-propyl-benzenesulfonamide |
| A9. | N-Cyclopropyl-4-fluoro-N-piperidin-4-yl-benzenesulfonamide |
| A10. | 2-(4-Chloro-phenyl)-N-ethyl-N-piperidin-4-yl-acetamide |
| A11. | N-Cyclopropyl-2-(4-methoxy-phenyl)-N-piperidin-4-yl-acetamide |

A12. 4-Phenyl-piperidine-4-carboxylic acid benzyl-methyl-amide

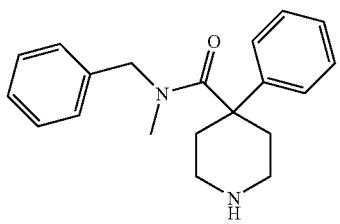

A12.1. 4-Phenyl-piperidine-1,4-dicarboxylic acid monobenzyl ester

A suspension of commercially available 4-phenyl-4-carboxypiperidine toluenesulfonate (7.55 g, 20 mmol), N-(benzyloxycarbonyloxy)succinimide (5.0 g, 20 mmol) and TEA (5 mL, 36 mmol) in CHCl$_3$ (100 mL) is stirred at r.t. for 48 h. The mixture is diluted with CH$_2$Cl$_2$ (100 mL) and extracted with 1 M aq. NaOH (3×50 mL). The aq. phase is extracted with Et$_2$O (2×50 mL), acidified (pH 2) with 6N aq. HCl and extracted with CH$_2$Cl$_2$ (4×50 mL). The combined CH$_2$Cl$_2$ extracts are dried (Na$_2$SO$_4$), filtered and evaporated to provide the title compound.

A12.2. 4-(Benzyl-methyl-carbamoyl)-4-phenyl-piperidine-1-carboxylic acid benzyl ester A mixture of 4-phenyl-piperidine-1,4-dicarboxylic acid monobenzyl ester (3.39 g, 10 mmol) and SOCl$_2$ (7 mL, 100 mmol) in CHCl$_3$ (150 mL) is heated at reflux for 3 h. The solvent and excess SOCl$_2$ are evaporated into a cold trap and the residue is redissolved in CHCl$_3$ (50 mL). The solution is added to a solution of methylbenzylamine (1.45 g, 12 mmol) and DIPEA (2 mL, 12 mmol) in cold (0° C.) CHCl$_3$ (100 mL). The mixture is stirred for 15 h at r.t. and then quenched with sat. aq. Na$_2$CO$_3$ (50 mL). The phases are separated and the aq. phase is extracted with CH$_2$Cl$_2$ (2×50 mL). The combined organic extracts are washed with 1N aq. HCl (50 mL) and sat. aq. NaCl (50 mL), dried (Na$_2$SO$_4$), filtered and evaporated. The residue is purified by FC (SiO$_2$, heptane-EtOAc) to provide the title compound.

A12.3. 4-Phenyl-piperidine-4-carboxylic acid benzyl-methyl-amide

A mixture of 4-(benzyl-methyl-carbamoyl)-4-phenyl-piperidine-1-carboxylic acid benzyl ester (4.4 g, 10 mmol) and Pd—C (10%, 400 mg) in MeOH (200 mL) is hydrogenated at r.t. and atmospheric pressure for 3 h. The mixture is filtered and evaporated. The residue is purified by reversed phase MPLC to provide the title compound.

The following intermediates are prepared from 4-phenyl-piperidine-1,4-dicarboxylic acid monobenzyl ester (Example A12.1) and commercially available amines using the method described in Example A12.

| Example No | Example |
|---|---|
| A12. | 4-Phenyl-piperidine-4-carboxylic acid benzyl-methyl-amide |
| A13. | 4-Phenyl-piperidine-4-carboxylic acid benzyl-(2-hydroxy-ethyl)-amide |

A14. 4-Methyl-piperidine-4-carboxylic acid benzyl-methyl-amide

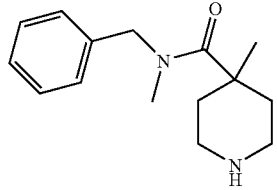

A14.1. 4-Methyl-piperidine-1,4-dicarboxylic acid 1-tert-butyl ester 4-ethyl ester A solution of NaHMDS (2M in THF, 148 mmol, 74 mL, diluted to 100 mL) is cooled at −78° C. and a solution of piperidine-1,4-dicarboxylic acid 1-tert-butyl ester 4-ethyl ester (25.74 g, 100 mmol) in THF (50 mL of solution) is added slowly. The mixture is stirred for 2 h at −78° C. Methyliodide (7.5 mL, 120 mmol) is dissolved in THF (60 mL) and the cold solution of enolate is added. The mixture is stirred at r.t. for 1 h and quenched with HCl (1M, 75 mL) and ether (200 mL). the phases are separated and the organic phase washed with HCl (1M, 2×50 mL) and NaOH (1M, 2×50 mL). The organic phase is dried (Na$_2$SO$_4$), filtered and evaporated to provide the crude title compound.

A14.2. 4-Methyl-piperidine-1,4-dicarboxylic acid monobenzyl ester

4-Methyl-piperidine-1,4-dicarboxylic acid 1-tert-butyl ester 4-ethyl ester (2.71 g, 10 mmol) is heated with 6M aq. HCl (20 mL) at 95° C. for 2 days. The mixture is cooled, basified with 33% aq. NaOH (ice bath cooling) and extracted with ether (2×50 mL). A spatula of NaH2PO4 is added, then the pH adjusted to 7 with conc. aq. HCl, CH$_2$Cl$_2$ (50 Vol %) is added and the mixture cooled at 0° C. Carbonic acid benzyl ester 2,5-dioxo-pyrrolidin-1-yl ester (1.508 g, 5 mmol) is added to the strongly stirred biphasic system and the mixture is stirred for 2 h. The pH is adjusted to 14 with aq. NaOH (1M) and the phases are separated. The aq. phase is extracted with CH$_2$Cl$_2$ (2×50 mL), the organic extracts are discarded. The pH is adjusted to 2 and the mixture is extracted with CHCl$_3$ (4×50 mL). The organic extracts are dried (Na$_2$SO$_4$), filtered and evaporated to provide the title compound.

A14.3. 4-Methyl-piperidine-4-carboxylic acid benzyl-methyl-amide

The compound is prepared from 4-methyl-piperidine-1,4-dicarboxylic acid monobenzyl ester and benzylmethylamine using the method described in Example A12.

The following intermediates are prepared from piperidine-1,4-dicarboxylic acid 1-tert-butyl ester 4-ethyl ester, commercially available alkyliodides and commercially available amines using the method described in Example A14.

| Example No | Example |
| --- | --- |
| A14. | 4-Methyl-piperidine-4-carboxylic acid benzyl-methyl-amide |
| A15. | 4-Methyl-piperidine-4-carboxylic acid (4-methoxy-benzyl)-methyl-amide |
| A16. | 4-Ethyl-piperidine-4-carboxylic acid benzyl-(2-hydroxy-ethyl)-amide |
| A17. | 4-Ethyl-piperidine-4-carboxylic acid benzyl-methyl-amide |

A18. 3,3-Diphenyl-pyrrolidine

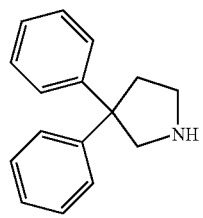

A suspension of LiAlH$_4$ (560 mg, 14.75 mmol) in THF (50 mL) is cooled at 0° C. and a solution of 4-bromo-2,2-diphenylbutyronitrile (1.50 g, 5 mmol) in THF (20 mL) is slowly added. The mixture is stirred at r.t. for 15 h, carefully quenched with MeOH and NaHCO$_3$ and filtered. The filtrate is evaporated, the residue taken up in CH$_2$Cl$_2$ (100 mL) and washed with sat. aq. Na$_2$CO$_3$. (50 mL). The aq. phase is re-extracted with CH$_2$Cl$_2$ (2×50 mL) and the combined organic extracts are dried (Na$_2$SO$_4$), filtered and evaporated. The residue is purified by reversed phase MPLC to provide the title compound.

Example B

Preparation of Intermediates

B1. 2-(4-Benzylpiperidino)-1-ethanamine

The material is commercially available.

B2. N-[1-(2-Amino-ethyl)-piperidin-4-yl]-N-ethyl-4-methoxy-benzenesulfonamide

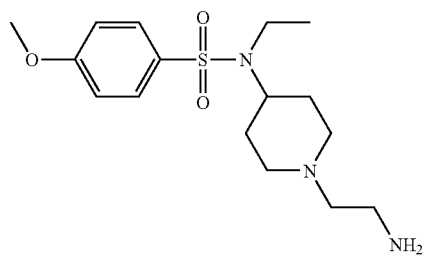

B2.1. (2-Bromo-ethyl)-carbamic acid tert-butyl ester

To 1 N aq. NaOH (200 mL) is added MeOH (400 mL) and the resulting solution is cooled at 20° C. 2-Bromoethylamine hydrobromide (25.0 g, 122 mmol) is added in a single portion, followed by di-tert-butyl dicarbonate (26.6 g, 122 mmol). The reaction mixture is stirred for 2.5 h. The MeOH is removed on a rotary evaporator, and the aq. suspension is extracted with CH$_2$Cl$_2$ (2×175 mL). The combined organic extracts are extracted with 5% aq. citric acid (300 mL), dried (MgSO$_4$), filtered, and evaporated to provide the title compound.

B2.2. (2-{4-[Ethyl-(4-methoxy-benzenesulfonyl)-amino]-piperidin-1-yl}-ethyl)-carbamic acid tert-butyl ester A mixture of N-ethyl-4-methoxy-N-piperidin-4-yl-benzenesulfonamide (Example A4., 1.19 g, 4 mmol), (2-bromo-ethyl)-carbamic acid tert-butyl ester (1.12 g, 5.0 mmol) and DIPEA (650 mg, 5 mmol) in THF (30 mL) is heated at reflux for 15 h. The solution is poured into Et$_2$O (150 mL) and extracted with sat. aq. Na$_2$CO$_3$ (2×50 mL) and sat. aq. NaCl (30 mL), dried (Na$_2$SO$_4$), filtered and evaporated. The residue is purified by reversed phase MPLC to provide the title compound.

B2.3. N-[1-(2-Amino-ethyl)-piperidin-4-yl]-N-ethyl-4-methoxy-benzenesulfonamide The title compound is prepared from (2-{4-[ethyl-(4-methoxy-benzenesulfonyl)-amino]-piperidin-1-yl}-ethyl)-carbamic acid tert-butyl ester using the method described in Example A4.2.

The following intermediates are prepared from Examples A2. to A12. and (2-bromo-ethyl)-carbamic acid tert-butyl ester (Example B2.1.) using the method described in Example B2.

| Example No | Example |
|---|---|
| B2. | N-[1-(2-Amino-ethyl)-piperidin-4-yl]-N-ethyl-4-methoxy-benzenesulfonamide |
| B3 | N-[1-(2-Amino-ethyl)-piperidin-4-yl]-N-ethyl-4-fluoro-benzenesulfonamide |
| B4. | N-[1-(2-Amino-ethyl)-piperidin-4-yl]-4-bromo-N-ethyl-benzenesulfonamide |
| B5. | N-[1-(2-Amino-ethyl)-piperidin-4-yl]-4-methoxy-N-propyl-benzenesulfonamide |
| B6. | N-[1-(2-Amino-ethyl)-piperidin-4-yl]-4-fluoro-N-propyl-benzenesulfonamide |
| B7. | 1-(2-Amino-ethyl)-4-benzyl-piperidin-4-ol |
| B8. | 1-(2-Amino-ethyl)-4-phenyl-piperidine-4-carboxylic acid benzyl-methyl-amide |
| B9. | 2-(3,3-Diphenyl-pyrrolidin-1-yl)-ethylamine |
| B10. | 1-(2-Amino-ethyl)-4-methyl-piperidine-4-carboxylic acid (4-methoxy-benzyl)-methyl-amide |
| B11. | 1-(2-Amino-ethyl)-4-methyl-piperidine-4-carboxylic acid benzyl-methyl-amide |

B9. 2-(3,3-Diphenyl-pyrrolidin-1-yl)-ethylamine

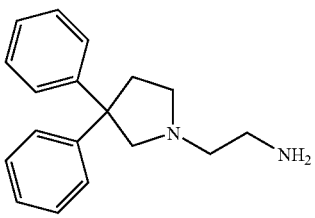

B9.1. (2-Bromo-ethyl)-carbamic acid benzyl ester

2-Bromoethylamine hydrobromide (15 g, 73 mmol) and N-(benzyloxycarbonyloxy)-succinimide (15.5 g, 62 mmol) are suspended in CH$_2$Cl$_2$ (150 mL) at 0° C. TEA (9 mL, 65 mmol) is added slowly keeping the temperature at 0° C. After 1 h the mixture is washed with 0.5M aq. KHSO$_4$ (50 mL) and sat. aq. NaCl (50 mL), the organic phase is dried (Na$_2$SO$_4$), filtered and evaporated to provide the title compound.

B9.2. [2-(3,3-Diphenyl-pyrrolidin-1-yl)-ethyl]-carbamic acid benzyl ester (2-Bromo-ethyl)-carbamic acid benzyl ester (1.10 g, 4.26 mmol), 3,3-diphenyl-pyrrolidine (Example A18, 836 mg, 3.75 mmol) and DIPEA (1.0 mL 5.7 mmol) are dissolved in THF (20 mL) and stirred for 15 h at reflux. The mixture is quenched with Na$_2$CO$_3$ (50 mL) and extracted with CH$_2$Cl$_2$ (3×50 mL). The organic extracts are washed with sat. aq. Na$_2$CO$_3$ (30 mL), dried (Na$_2$SO$_4$), filtered and evaporated. The residue is purified by FC (SiO$_2$, EtOAc-heptane) to provide the title compound.

B9.3. 2-(3,3-Diphenyl-pyrrolidin-1-yl)-ethylamine

[2-(3,3-Diphenyl-pyrrolidin-1-yl)-ethyl]-carbamic acid benzyl ester (1.44 g, 3.6 mmol) is dissolved in MeOH (50 mL) and Pd—C (10%, 150 mg) is added. The mixture is stirred under hydrogen atmosphere for 15 h. The mixture is filtered and the filtrate evaporated to provide the title compound.

The following intermediates are prepared from Examples A14. to A18 and (2-bromo-ethyl)-carbamic acid benzyl ester (Example B9.1.) using the method described in Example B9.

Example C

Preparation of Intermediates

C1. 1,3-Bis-(2,6-dimethyl-pyridin-4-yl)-urea

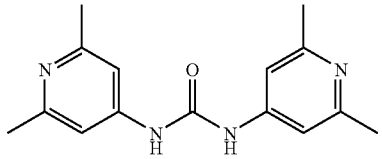

C1.1. 2,6-Dimethyl-4-nitro-pyridine 1-oxide

Lutidine-N-oxide (19 g, 155 mmol) is cooled at 0° C. and a mixture of fuming HNO$_3$ (100%, 37.5 mL) and conc. H$_2$SO$_4$ (95-97%, 52.5 mL), prepared by addition of H$_2$SO$_4$ to HNO$_3$ at 0° C., is added slowly. The mixture is heated at 80° C. for 3 h. The cooled mixture is carefully poured into ice-water (500 mL). A white precipitate forms that is filtered. The precipitate is dissolved in CH$_2$Cl$_2$ (100 mL) and the filtrate is extracted with CH$_2$Cl$_2$ (4×75 mL). The organic extracts are combined with the dissolved precipitate and washed with sat. aq. NaCl (2×75 mL), dried (Na$_2$SO$_4$), filtered and evaporated to provide the title compound.

C1.2. 2,6-Dimethyl-pyridin-4-ylamine 2,6-Dimethyl-4-nitro-pyridine 1-oxide (9.62 g, 57 mmol) is dissolved in AcOH (300 mL) and Fe (powder, 29 g) is added. The mixture is stirred for 1 h at 100° C. The mixture is cooled to r.t. and filtered. The filtercake is thoroughly washed with AcOH and then discarded. The filtrate is evaporated, diluted with water (100 mL), basified with NaOH (1 M, 100 mL), filtered from the formed precipitate and the filtrate is extracted with CHCl$_3$ (10×50 mL). The combined organic extracts are dried (Na$_2$SO$_4$), filtered and evaporated. The residue is crystallized from heptane-CHCl$_3$ to provide the title compound.

C1.3. 1,3-Bis-(2,6-dimethyl-pyridin-4-yl)-urea 2,6-Dimethyl-pyridin-4-ylamine (1.22 g, 10 mmol) is dissolved in dry dioxane (30 mL) and CDI (891 mg, 5.5 mmol) is added. The mixture is heated at 80° C. for 1 h. Further CDI (160 mg) is added and stirring is continued for 15 h. The mixture is evaporated and purified by FC (SiO$_2$, EtOAc-MeOH) to provide the title compound.

C2. 4-Isocyanato-2-methyl-6-(E)-styryl-pyridine

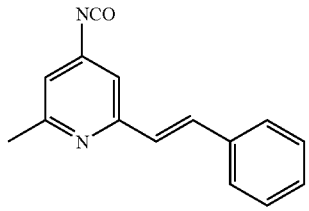

C2.1. 2-Methyl-6-(E)-styryl-isonicotinic acid

A suspension of 2-chloro-6-methyl-isonicotinic acid (171.6 mg, 1 mmol), (E)-2-phenyl-etheneboronic acid (180.0 mg, 1.2 mmol), K$_2$CO$_3$ (414 mg), Pd(dppf)Cl$_2$-CH$_2$Cl$_2$ (27 mg) in CH$_3$CN—H$_2$O (3:1, 10 mL) is stirred under argon at 90° C. for 15 h. The solution is cooled to r.t. and aq. hydrochloric acid (2 M, 1.5 mL) is added to adjust the pH at 3. The mixture is evaporated to dryness and purified by reversed phase MPLC to provide the title compound.

C2.2. 2-Methyl-6-(E)-styryl-isonicotinoyl azide

To a solution of 2-methyl-6-(E)-styryl-isonicotinic acid (214 mg, 0.89 mmol) in DMF (5 mL) is added at 0° C. TEA (0.21 mL, 1.5 mmol) and slowly (30 min) DPPA (366 mg, 1.33 mmol). The reaction mixture is stirred for 0.5 h at 0° C. and 0.5 h at r.t. The reaction is quenched with ice (20 g) and extracted with Et$_2$O (6×30 mL). The combined organic extracts are washed successively with saturated NaHCO$_3$ (2×15 mL) and water (2×10 mL), and are evaporated in vacuo without heating. The residue is purified by FC (SiO$_2$, EtOAc-heptane) to provide the title compound.

C2.3. 4-Isocyanato-2-methyl-6-(E)-styryl-pyridine

2-Methyl-6-(E)-styryl-isonicotinoyl azide (79.9 mg, 0.3 mmol) is dissolved in dry toluene (4 mL) and heated at reflux for 2 h. The resulting solution of the title compound is carried forward without further isolation.

The following intermediates are prepared from 2-chloro-6-methyl-isonicotinic acid or 2-chloro-isonicotinic acid and commercially available boronic acids using the method described in Example C2.

| Example No | Example |
|---|---|
| C2. | 4-Isocyanato-2-methyl-6-(E)-styryl-pyridine |
| C3. | 2-[(E)-2-(4-Fluoro-phenyl)-vinyl]-4-isocyanato-6-methyl-pyridine |
| C4. | 4-Isocyanato-2-(E)-styryl-pyridine |
| C5. | 2-[(E)-2-(4-Fluoro-phenyl)-vinyl]-4-isocyanato-pyridine |
| C6. | 2-[(E)-2-(4-Chloro-phenyl)-vinyl]-4-isocyanato-pyridine |

C7. 2-Ethyl-4-isocyanato-6-methyl-pyridine

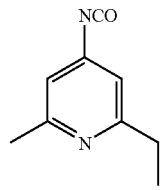

C7.1. 2-Chloro-6-methyl-isonicotinic acid tert-butyl ester

N,N-dimethylformamide-di-tert.-butyl-acetal (19 mL, 80 mmol) is added during 40 min to a hot (65° C., flask temperature) suspension of 2-chloro-6-methyl-isonicotinic acid (3.40 g, 19.8 mmol) in dry toluene (100 mL). The clear orange solution is stirred at 80° C. for 48 h, cooled to r.t. and diluted with toluene (100 mL). The solution is washed with water (2×40 mL), sat. aq. NaHCO$_3$ (3×30 mL) and sat. aq. NaCl (25 mL), dried (Na$_2$SO$_4$), filtered and evaporated. The residue is purified by FC (SiO$_2$, CH$_2$Cl$_2$-MeOH) to provide the title compound.

C7.2. 2-Ethyl-6-methyl-isonicotinic acid

A solution of ethylmagnesiumbromide (freshly prepared from ethylbromide (392 mg, 3.6 mmol) and magnesium (83 mg, 3.4 mmol)) in Et$_2$O (10 mL) is added to a cooled (−40° C.) and mechanically stirred solution of 2-chloro-6-methyl-isonicotinic acid tert-butyl ester (0.76 g, 3.34 mmol), Fe(acac)$_3$ (21.2 mg, 0.06 mmol) and NMP (0.6 mL) in THF (60 mL). The mixture is warmed to r.t. during 0.5 h, diluted with Et$_2$O (150 mL) and quenched with aq. KHSO$_4$ (1 M, 40 mL). The phases are separated and the aq. phase is extracted with Et$_2$O (2×50 mL). The combined organic extracts are dried (MgSO$_4$), filtered and evaporated. The residue is purified by reversed phase MPLC. The obtained 2-ethyl-6-methyl-isonicotinic acid tert-butyl ester is dissolved in CH$_2$Cl$_2$ (10 mL). TFA (10 mL) is added and the mixture stirred at r.t. for 0.5 h. The mixture is evaporated and the residue dried in HV to provide the title compound.

C7.3. 2-Ethyl-6-methyl-isonicotinoyl azide

The title compound is prepared from 2-ethyl-6-methyl-isonicotinic acid using the method described in Example C2.2.

C7.4. 2-Ethyl-4-isocyanato-6-methyl-pyridine

The title compound is prepared from 2-ethyl-6-methyl-isonicotinoyl azide using the method described in Example C2.3.

The following intermediates are prepared from 2-chloro-6-methyl-isonicotinic acid and commercially available alkylbromides using the method described in Example C7.

| Example No | Example |
|---|---|
| C7. | 2-Ethyl-4-isocyanato-6-methyl-pyridine |
| C8. | 4-Isocyanato-2-methyl-6-phenethyl-pyridine |
| C9. | 4-Isocyanato-2-methyl-6-propyl-pyridine |

C10. 4-Isocyanato-2,6-diethyl-pyridine

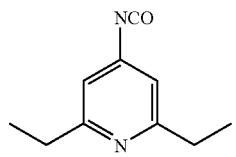

The title compound is prepared from 2,6-dichloro-isonicotinic acid tert-butyl ester (prepared from 2,6-dichloro-isonicotinic acid according to the method of Example C7.1) and 2.2 equivalents of ethylbromide using the methods described in Example C7.

C11. 2-Chloro-4-isocyanatopyridine

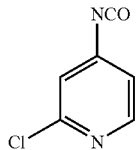

The title compound is prepared from commercially available 2-chloro-isonicotinic acid using the method described in Example C2.2. and C2.3.

C12. (2,6-Dimethyl-pyridin-4-yl)-carbamic acid pentafluorophenyl ester

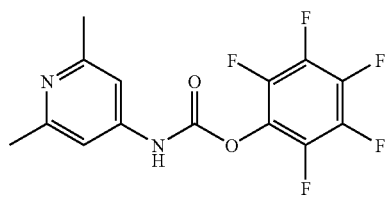

A solution of 2,6-dimethyl-pyridin-4-ylamine (Example C1.2., 1.23 g, 10 mmol) in THF (30 mL) is slowly added to a cooled (−10° C.) solution of bis(pentafluorophenyl)carbonate (3.94 g, 10 mmol) in THF (10 mL). The mixture is stirred at r.t. for 48 h and the solution of title compound is used as stock solution for subsequent coupling reactions.

C13. (2-Ethyl-6-methyl-pyridin-4-yl)-carbamic acid pentafluorophenyl ester

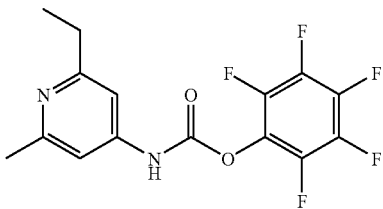

C13.1. 2-Ethyl-6-methyl-4-nitro-pyridine 1-oxide

2-Ethyl-6-methylpyridine (22.2 g, 183 mmol) is dissolved in $CHCl_3$ (250 mL) and 3-chloroperbenzoic acid (49.7 g, 201.6 mmol) is added portionwise. The mixture is stirred for 15 h, filtered and evaporated. The residue is dissolved in ether (250 mL) and washed with aq. NaOH (1M, 6×100 mL). The organic phase is dried (MgSO4), filtered and evaporated to provide the crude N-oxide.

The N-oxide is slowly added to a cooled (0° C.) mixture of fuming $HNO_3$ (100%, 40.6 mL) and conc. $H_2SO_4$ (95-97%, 55.4 mL), prepared by addition of $H_2SO_4$ to $HNO_3$ at 0° C. The mixture is heated at 80° C. for 1 h. The cooled mixture is carefully poured into ice-water (400 mL). The mixture is diluted with $CH_2Cl_2$ (100 mL), the phases separated and the aq. phase is extracted with $CH_2Cl_2$ (4×75 mL). The organic extracts are washed with sat. aq. NaCl (2×75 mL), dried ($Mg_2SO_4$), filtered and evaporated to provide the title compound.

C13.2. 2-Ethyl-6-methyl-pyridin-4-ylamine

2-Ethyl-6-methyl-4-nitro-pyridine 1-oxide (27.65 g, 151.8 mmol) is dissolved in AcOH (330 mL) and Fe (powder, 33.9 g) is added. The mixture is stirred for 1 h at 100° C. The mixture is cooled to r.t. and filtered. The filtercake is thoroughly washed with AcOH and then discarded. The filtrate is evaporated, diluted with water (100 mL), basified (pH>10) with NaOH (1 M, 100 mL), filtered from the formed precipitate and the filtrate is extracted with $CH_2Cl_2$ (10×75 mL). The combined organic extracts are dried ($MgSO_4$), filtered and evaporated to provide the title compound.

C13.3. (2-Ethyl-6-methyl-pyridin-4-yl)-carbamic acid pentafluorophenyl ester A solution of 2-ethyl-6-methyl-pyridin-4-ylamine (1.33 g, 9.8 mmol) in THF (25 mL) is slowly added to a solution of bis(pentafluorophenyl)carbonate (3.99 g, 10.1 mmol) in THF (10 mL). The mixture is stirred at r.t. for 48 h and the solution of title compound is used as stock solution for subsequent coupling reactions.

Example D

Preparation of Intermediates

D1. 1-(2-Chloro-ethyl)-3-(2,6-dimethyl-pyridin-4-yl)-urea

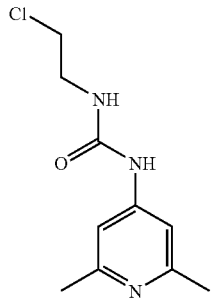

2,6-Dimethyl-pyridin-4-ylamine (Example C1.2., 1.22 g, 10 mmol) is dissolved in dry THF (30 mL) and 1-chloro-2-isocyanato-ethane (1.06 g, 10 mmol) is added. The mixture is stirred at r.t. for 15 h. The mixture is evaporated and the residue purified by MPLC to provide the title compound.

The following intermediates are prepared from 2,6-dimethyl-pyridin-4-ylamine or 2-ethyl-6-methyl-pyridin-4-ylamine (Example C13.2.) and 1-chloro-2-isocyanato-ethane using the method described in Example D1.

| Example No | Example |
|---|---|
| D1. | 1-(2-Chloro-ethyl)-3-(2,6-dimethyl-pyridin-4-yl)-urea |
| D2. | 1-(2-Chloro-ethyl)-3-(2-ethyl-6-methyl-pyridin-4-yl)-urea |

D3. [3-(2-Methyl-pyridin-4-yl)-ureido]-acetic acid

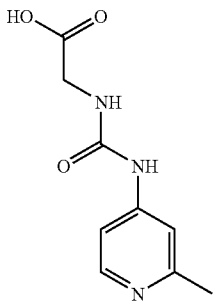

D3.1. 2-Methyl-pyridin-4-ylamine

The material is prepared from commercially available 2-methyl-4-nitro-pyridine 1-oxide using the method described for Example C1.2.

D3.2. [3-(2-Methyl-pyridin-4-yl)-ureido]-acetic acid

2-Methyl-pyridin-4-ylamine (1.08 g, 10 mmol) is dissolved in dry THF (30 mL) and isocyanatoacetic acid ethyl ester (1.29 g, 10 mmol) is added. The mixture is stirred at r.t. for 15 h. The mixture is evaporated and 6N aq. HCl (20 mL) is added. The mixture is stirred at 50° C. for 6 h, evaporated and the residue purified by reversed phase MPLC to provide the title compound.

Example E

Preparation of Intermediates

E1. 1-(2,6-Dimethyl-pyridin-4-yl)-3-[2-(4-methylamino-piperidin-1-yl)-ethyl]-urea

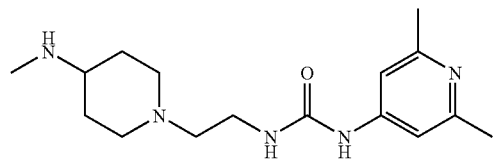

Example E1.1

4-(tert-Butoxycarbonyl-methyl-amino)-piperidine-1-carboxylic acid benzyl ester

A mixture of commercially available 4-oxo-piperidine-1-carboxylic acid benzyl ester (4.67 g, 20 mmol) and methylamine (8 M in EtOH, 12.5 mL, 100 mmol) in dioxane (total volume of 100 mL) is stirred at r.t. for 15 min. NaBHAc$_3$ (6.4 g, 30 mmol) is added and the mixture is stirred for 15 h. The mixture is quenched with 1 M aq. NaOH (30 mL) and stirred at r.t. for 30 min. The mixture is diluted with water (50 mL) and extracted with CH$_2$Cl$_2$ (3×75 mL). The organic extracts are dried (Na$_2$SO$_4$), filtered and evaporated. The residue is dissolved in ether (200 mL) and TEA (1.4 mL, 10 mmol) and, subsequently, a solution of di-tert.butyl-dicarbonat (3.82 g, 17.5 mmol) in ether (10 mL) are added. The mixture is stirred at r.t. for 15 h and quenched with 1 M aq. NaOH (30 mL). The phases are separated and the organic phase is washed with 1 M aq. NaOH (30 mL), 1 M aq. KHSO$_4$ (2×30 mL) and sat. aq. NaCl (30 mL). The organic phase is dried (Na$_2$SO$_4$), filtered and evaporated to provide the title compound.

Example E1.2

Methyl-piperidin-4-yl-carbamic acid tert-butyl ester

A mixture of 4-(tert-butoxycarbonyl-methyl-amino)-piperidine-1-carboxylic acid benzyl ester (17.5 mmol) and Pd—C (10%, 500 mg) in MeOH (150 mL) hydrogenated at atm. pressure and r.t. for 15 h. The mixture is filtered and evaporated. The residue is dissolved in CH$_2$Cl$_2$ (100 mL) and 1 M aq. NaOH (50 mL) is added. The mixture is stirred for 6 h at r.t., then the phases are separated and the aq. phase is extracted with CH$_2$Cl$_2$ (3×50 mL). The combined organic extracts are dried (Na$_2$SO$_4$), filtered and evaporated to provide the title compound.

Example E1.3

(1-{2-[3-(2,6-Dimethyl-pyridin-4-yl)-ureido]-ethyl}-piperidin-4-yl)-methyl-carbamic acid tert-butyl ester A suspension of methyl-piperidin-4-yl-carbamic acid tert-butyl ester (3.57 g, 16.7 mmol), NaHCO₃ (6.7 g, 79 mmol), NaI (1.5 g, 10 mmol) and 1-(2-chloro-ethyl)-3-(2,6-dimethyl-pyridin-4-yl)-urea (Example D1, 2.14 g 9.4 mmol) in THF (30 mL) is stirred at 50° C. for 14 days. The mixture is quenched with Na₂CO₃ (50 mL) and extracted with CH₂Cl₂ (5×50 mL). The organic extracts are washed with sat. aq. Na₂CO₃ (30 mL), dried (Na₂SO₄), filtered and evaporated. The residue is purified by FC to provide the title compound.

Example E1.4

1-(2,6-Dimethyl-pyridin-4-yl)-3-[2-(4-methylamino-piperidin-1-yl)-ethyl]-urea

The title compound is prepared from (1-{2-[3-(2,6-dimethyl-pyridin-4-yl)-ureido]-ethyl}-piperidin-4-yl)-methyl-carbamic acid tert-butyl ester using the method described in Example A4.2.

The following intermediates are prepared using the method described in Example E1. Piperidines are obtained according to the method of Example E1.1 by reductive amination of 4-oxo-piperidine-1-carboxylic acid benzyl ester with ethylamine (2M in THF) or cyclopropylamine. Coupling of the protected piperidine, prepared by the method of Example E1.2., with 1-(2-chloro-ethyl)-3-(2,6-dimethyl-pyridin-4-yl)-urea (Example D1) or 1-(2-chloro-ethyl)-3-(2-ethyl-6-methyl-pyridin-4-yl)-urea (Example D2) is achieved according to the method of Example E1.3. Deprotection according to the method of Example E1.4 provides the title compounds.

| Example No | Example |
|---|---|
| E1. | 1-(2,6-Dimethyl-pyridin-4-yl)-3-[2-(4-methylamino-piperidin-1-yl)-ethyl]-urea |
| E2. | 1-(2,6-Dimethyl-pyridin-4-yl)-3-[2-(4-ethylamino-piperidin-1-yl)-ethyl]-urea |
| E3. | 1-[2-(4-Cyclopropylamino-piperidin-1-yl)-ethyl]-3-(2,6-dimethyl-pyridin-4-yl)-urea |
| E4. | 1-[2-(4-Ethylamino-piperidin-1-yl)-ethyl]-3-(2-ethyl-6-methyl-pyridin-4-yl)-urea |

Preparation of Final Products

Example 1

1-[2-(4-Benzyl-piperidin-1-yl)-ethyl]-3-(2,6-dimethyl-pyridin-4-yl)-urea

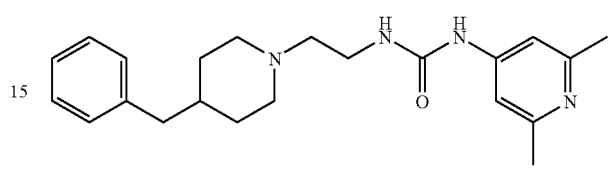

A suspension of 2-(4-benzylpiperidino)-1-ethanamine (Example B1, 54.6 mg, 0.25 mmol), TEA (35 μL, 0.25 mmol) and 1,3-bis-(2,6-dimethyl-pyridin-4-yl)-urea (Example B1, 67.6 mg 0.25 mmol) in dioxane (2 mL) is heated at reflux for 24 h. The solvent is evaporated and the residue purified by HPLC to provide the title compound.

The following examples are prepared from intermediates Example B1.-B9. and Example C1. using the method described for Example 1.

| Example No | Example | $t_R$ | $[M + H]^+$ |
|---|---|---|---|
| 1 | 1-[2-(4-Benzyl-piperidin-1-yl)-ethyl]-3-(2,6-dimethyl-pyridin-4-yl)-urea | 0.63 | 367.42 |
| 2 | 1-{2-[3-(2,6-Dimethyl-pyridin-4-yl)-ureido]-ethyl}-4-phenyl-piperidine-4-carboxylic acid benzyl-methyl-amide | 0.70 | 500.47 |
| 3 | N-(1-{2-[3-(2,6-Dimethyl-pyridin-4-yl)-ureido]-ethyl}-piperidin-4-yl)-4-methoxy-N-propyl-benzenesulfonamide | 0.68 | 504.27 |
| 4 | N-(1-{2-[3-(2,6-Dimethyl-pyridin-4-yl)-ureido]-ethyl}-piperidin-4-yl)-4-fluoro-N-propyl-benzenesulfonamide | 0.68 | 492.23 |
| 5 | 1-(2,6-Dimethyl-pyridin-4-yl)-3-[2-(3,3-diphenyl-pyrrolidin-1-yl)-ethyl]-urea | 0.68 | 415.20 |

Example 6

1-[2-(4-Benzyl-4-hydroxy-piperidin-1-yl)-ethyl]-3-(2,6-dimethyl-pyridin-4-yl)-urea

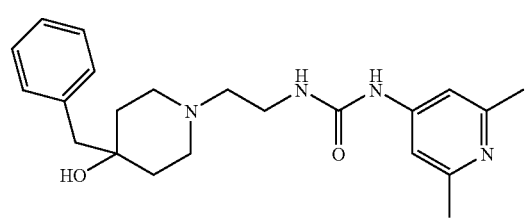

A suspension of commercially available 4-benzyl-piperidin-4-ol (383 mg, 2.0 mmol). NaHCO₃ (672 mg, 8.0 mmol) and 1-(2-chloro-ethyl)-3-(2,6-dimethyl-pyridin-4-yl)-urea (Example D1., 227.7 mg 1.0 mmol) in THF (4 mL) is stirred at 50° C. for 4 days. The mixture is quenched with Na$_2$CO$_3$ (10 mL) and extracted with CH$_2$Cl$_2$ (3×10 mL). The organic extracts are washed with sat. aq. Na$_2$CO$_3$ (10 mL), dried (Na$_2$SO$_4$), filtered and evaporated. The residue is purified by HPLC to provide the title compound.

washed with sat. aq. Na$_2$CO$_3$ (70 mL), dried (Na$_2$SO$_4$), filtered and evaporated. The residue is purified by MPLC to provide the title compound.

The following examples are prepared from intermediates Example A3.-A17. and intermediates Example D1. or D2. using the method described for Example 7.

| Example No | Example | $t_R$ | [M + H]$^+$ |
|---|---|---|---|
| 7 | 2-(4-Chloro-phenyl)-N-(1-{2-[3-(2,6-dimethyl-pyridin-4-yl)-ureido]-ethyl}-piperidin-4-yl)-N-ethyl-acetamide | 0.67 | 472.41 |
| 8 | N-Cyclopropyl-N-(1-{2-[3-(2,6-dimethyl-pyridin-4-yl)-ureido]-ethyl}-piperidin-4-yl)-4-fluoro-benzenesulfonamide | 0.67 | 490.27 |
| 9 | N-Cyclopropyl-N-(1-{2-[3-(2,6-dimethyl-pyridin-4-yl)-ureido]-ethyl}-piperidin-4-yl)-2-(4-methoxy-phenyl)-acetamide | 0.66 | 480.5 |
| 10 | 1-[2-(4-Benzyloxy-piperidin-1-yl)-ethyl]-3-(2,6-dimethyl-pyridin-4-yl)-urea | 0.63 | 383.28 |
| 11 | 1-{2-[3-(2,6-Dimethyl-pyridin-4-yl)-ureido]-ethyl}-4-phenyl-piperidine-4-carboxylic acid benzyl-(2-hydroxy-ethyl)-amide | 0.67 | 530.38 |
| 12 | 1-{2-[3-(2-Ethyl-6-methyl-pyridin-4-yl)-ureido]-ethyl}-4-phenyl-piperidine-4-carboxylic acid benzyl-(2-hydroxy-ethyl)-amide | 0.69 | 544.3 |
| 13 | 4-Ethyl-1-{2-[3-(2-ethyl-6-methyl-pyridin-4-yl)-ureido]-ethyl}-piperidine-4-carboxylic acid benzyl-(2-hydroxy-ethyl)-amide | 0.63 | 496.42 |
| 14 | 4-Ethyl-1-{2-[3-(2-ethyl-6-methyl-pyridin-4-yl)-ureido]-ethyl}-piperidine-4-carboxylic acid benzyl-methyl-amide | 0.67 | 466.36 |

| Example No | Example | $t_R$ | [M + H]$^+$ |
|---|---|---|---|
| 6 | 1-[2-(4-Benzyl-4-hydroxy-piperidin-1-yl)-ethyl]-3-(2,6-dimethyl-pyridin-4-yl)-urea | 0.55 | 383.37 |

Example 7

2-(4-Chloro-phenyl)-N-(1-{2-[3-(2,6-dimethyl-pyridin-4-yl)-ureido]-ethyl}-piperidin-4-yl)-N-ethyl-acetamide

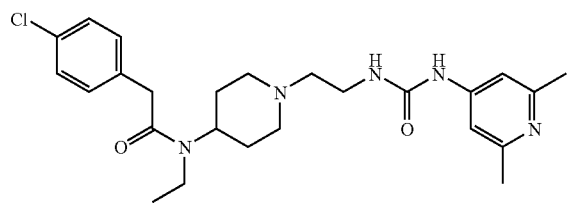

A suspension of 2-(4-chloro-phenyl)-N-ethyl-N-piperidin-4-yl-acetamide (Example A10., 3.37 g, 12.0 mmol), NaHCO$_3$ (5.4 g, 64 mmol), NaI (1.2 g, 8 mmol) and 1-(2-chloro-ethyl)-3-(2,6-dimethyl-pyridin-4-yl)-urea (Example D1, 1.82 g 8 mmol) in THF (40 mL) is stirred at 50° C. for 27 days. The mixture is quenched with Na$_2$CO$_3$ (150 mL) and extracted with CH$_2$Cl$_2$ (3×100 mL). The organic extracts are Example 15

N-(1-{2-[3-(2,6-Dimethyl-pyridin-4-yl)-ureido]-ethyl}-piperidin-4-yl)-N-ethyl-4-methoxy-benzenesulfonamide

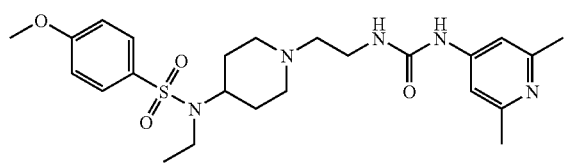

A suspension of N-ethyl-4-methoxy-N-piperidin-4-yl-benzenesulfonamide (Example A4., 2.09 g, 7.0 mmol), NaHCO$_3$ (3.4 g, 40 mmol), NaI (0.75 g, 5 mmol) and 1-(2-chloro-ethyl)-3-(2,6-dimethyl-pyridin-4-yl)-urea (Example D1, 1.14 g 5 mmol) in THF (30 mL) is stirred at 50° C. for 27 days. The mixture is quenched with Na$_2$CO$_3$ (150 mL) and extracted with CH$_2$Cl$_2$ (3×100 mL). The organic extracts are washed with sat. aq. Na$_2$CO$_3$ (70 mL), dried (Na$_2$SO$_4$), filtered and evaporated. The residue is purified by MPLC to provide the title compound.

| Example No | Example | $t_R$ | [M + H]$^+$ |
|---|---|---|---|
| 15 | N-(1-{2-[3-(2,6-Dimethyl-pyridin-4-yl)-ureido]-ethyl}-piperidin-4-yl)-N-ethyl-4-methoxy-benzenesulfonamide | 0.66 | 490.32 |

Example 16

N-(1-{2-[3-(2,6-Dimethyl-pyridin-4-yl)-ureido]-ethyl}-piperidin-4-yl)-N-ethyl-4-fluoro-benzenesulfonamide)

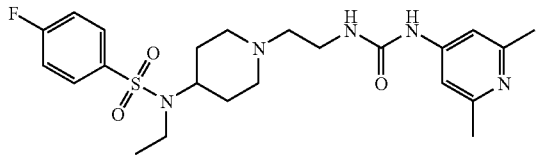

A suspension of N-ethyl-4-fluoro-N-piperidin-4-yl-benzenesulfonamide (Example A5., 3.09 g, 10.8 mmol), NaHCO$_3$ (5.4 g, 64 mmol), NaI (1.2 g, 8 mmol) and 1-(2-chloro-ethyl)-3-(2,6-dimethyl-pyridin-4-yl)-urea (Example D1, 1.82 g 8 mmol) in THF (40 mL) is stirred at 50° C. for 27 days. The mixture is quenched with Na$_2$CO$_3$ (150 mL) and extracted with CH$_2$Cl$_2$ (3×100 mL). The organic extracts are washed with sat. aq. Na$_2$CO$_3$ (70 mL), dried (Na$_2$SO$_4$), filtered and evaporated. The residue is purified by MPLC to provide the title compound.

| Example No | Example | $t_R$ | [M + H]$^+$ |
|---|---|---|---|
| 16 | N-(1-{2-[3-(2,6-Dimethyl-pyridin-4-yl)-ureido]-ethyl}-piperidin-4-yl)-N-ethyl-4-fluoro-benzenesulfonamide | 0.66 | 478.40 |

Example 17

1-(2-{3-[2-Methyl-6-((E)-styryl)-pyridin-4-yl]-ureido}-ethyl)-4-phenyl-piperidine-4-carboxylic acid benzyl-methyl-amide To a solution of 1-(2-amino-ethyl)-4-phenyl-piperidine-4-carboxylic acid benzyl-methyl-amide (Example B8., 0.25 mmol) in CH$_2$Cl$_2$ is added a freshly prepared solution of 4-isocyanato-2-methyl-6-(E)-styryl-pyridine (Example C2., 0.3 mmol) in toluene (2 mL). The mixture is stirred for 15 h at 20° C. Evaporation of the solvent and purification by HPLC provides the title compound.

The following examples are prepared from Examples B1.-B8. and Examples C2.-C10. using the method described for Example 17.

| Example No | Example | $t_R$ | [M + H]$^+$ |
|---|---|---|---|
| 17 | 1-(2-{3-[2-Methyl-6-((E)-styryl)-pyridin-4-yl]-ureido}-ethyl)-4-phenyl-piperidine-4-carboxylic acid benzyl-methyl-amide | 0.79 | 588.46 |
| 18 | 1-[2-(4-Benzyl-piperidin-1-yl)-ethyl]-3-{2-[(E)-2-(4-fluoro-phenyl)-vinyl]-6-methyl-pyridin-4-yl}-urea | 0.76 | 473.42 |
| 19 | 1-[2-(4-Benzyl-4-hydroxy-piperidin-1-yl)-ethyl]-3-[2-((E)-styryl)-pyridin-4-yl]-urea | 0.67 | 457.40 |
| 20 | 1-[2-(4-Benzyl-4-hydroxy-piperidin-1-yl)-ethyl]-3-{2-[(E)-2-(4-fluoro-phenyl)-vinyl]-pyridin-4-yl}-urea | 0.69 | 475.40 |
| 21 | 1-[2-(4-Benzyl-4-hydroxy-piperidin-1-yl)-ethyl]-3-{2-[(E)-2-(4-chloro-phenyl)-vinyl]-pyridin-4-yl}-urea | 0.71 | 491.38 |
| 22 | N-Ethyl-4-methoxy-N-(1-{2-[3-(2-methyl-6-phenethyl-pyridin-4-yl)-ureido]-ethyl}-piperidin-4-yl)-benzenesulfonamide | 0.74 | 580.45 |
| 23 | 1-{2-[3-(2-Methyl-6-propyl-pyridin-4-yl)-ureido]-ethyl}-4-phenyl-piperidine-4-carboxylic acid benzyl-methyl-amide | 0.74 | 528.5 |
| 24 | 1-[2-(4-Benzyl-piperidin-1-yl)-ethyl]-3-(2-methyl-6-propyl-pyridin-4-yl)-urea | 0.70 | 395.55 |
| 25 | N-Ethyl-4-methoxy-N-(1-{2-[3-(2-methyl-6-propyl-pyridin-4-yl)-ureido]-ethyl}-piperidin-4-yl)-benzenesulfonamide | 0.69 | 518.29 |
| 26 | 1-[2-(4-Benzyl-piperidin-1-yl)-ethyl]-3-(2-ethyl-6-methyl-pyridin-4-yl)-urea | 0.66 | 381.27 |
| 27 | N-Ethyl-N-(1-{2-[3-(2-ethyl-6-methyl-pyridin-4-yl)-ureido]-ethyl}-piperidin-4-yl)-4-methoxy-benzenesulfonamide | 0.67 | 504.25 |
| 28 | 1-{2-[3-(2-Ethyl-6-methyl-pyridin-4-yl)-ureido]-ethyl}-4-phenyl-piperidine-4-carboxylic acid benzyl-methyl-amide | 0.72 | 514.34 |
| 29 | 1-[2-(4-Benzyl-4-hydroxy-piperidin-1-yl)-ethyl]-3-(2-ethyl-6-methyl-pyridin-4-yl)-urea | 0.58 | 397.21 |
| 30 | N-Ethyl-N-(1-{2-[3-(2-ethyl-6-methyl-pyridin-4-yl)-ureido]-ethyl}-piperidin-4-yl)-4-fluoro-benzenesulfonamide | 0.66 | 492.20 |
| 31 | 1-[2-(4-Benzyl-piperidin-1-yl)-ethyl]-3-(2,6-diethyl-pyridin-4-yl)-urea | 0.66 | 395.24 |
| 32 | 1-[2-(4-Benzyl-4-hydroxy-piperidin-1-yl)-ethyl]-3-(2,6-diethyl-pyridin-4-yl)-urea | 0.60 | 411.21 |

-continued

| Example No | Example | $t_R$ | $[M + H]^+$ |
|---|---|---|---|
| 33 | N-(1-{2-[3-(2,6-Diethyl-pyridin-4-yl)-ureido]-ethyl}-piperidin-4-yl)-N-ethyl-4-methoxy-benzenesulfonamide | 0.67 | 518.26 |
| 34 | N-(1-{2-[3-(2,6-Diethyl-pyridin-4-yl)-ureido]-ethyl}-piperidin-4-yl)-N-ethyl-4-fluoro-benzenesulfonamide | 0.67 | 506.24 |

Example 35

1-[2-(4-Benzyl-4-hydroxy-piperidin-1-yl)-ethyl]-3-(2-phenethyl-pyridin-4-yl)-urea

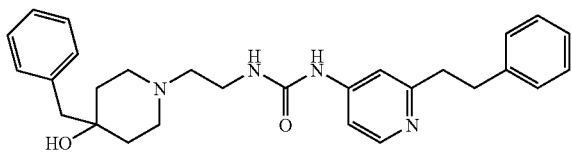

A suspension of 1-[2-(4-benzyl-4-hydroxy-piperidin-1-yl)-ethyl]-3-[2-((E)-styryl)-pyridin-4-yl]-urea (Example 19., 47.0 mg, 0.1 mmol) and Pd—C (10%, 10 mg) in MeOH (10 mL) is stirred under hydrogen atmosphere for 15 h. The catalyst is filtered off and the reaction mixture evaporated to provide the title compound.

The following compounds are prepared from Examples 17.-20. using the method described for Example 35.

Example 39.1

1-[2-(4-Benzyl-piperidin-1-yl)-2-oxo-ethyl]-3-(2-methyl-pyridin-4-yl)-urea

To a cooled (0° C.) mixture of [3-(2-methyl-pyridin-4-yl)-ureido]-acetic acid (Example D3., 105 mg, 0.5 mmol), 4-benzylpiperidine (Example A1., 105 mg, 0.6 mmol), HOBt (81 mg, 0.6 mmol), TEA (0.14 mL, 1 mmol) and a cat. amount of DMAP in $CH_2Cl_2$ (20 mL) are added, followed by EDC (115 mg, 0.6 mmol). The mixture is stirred at r.t. for 15 h. The mixture is quenched with sat. aq. $Na_2CO_3$ (25 mL), the phases are separated, and the aq. phase is extracted with $CH_2Cl_2$ (3×30 mL). The combined organic extracts are dried ($Na_2SO_4$), filtered and evaporated to provide the crude title compound.

| Example No | Example | $t_R$ | $[M + H]^+$ |
|---|---|---|---|
| 35 | 1-[2-(4-Benzyl-4-hydroxy-piperidin-1-yl)-ethyl]-3-(2-phenethyl-pyridin-4-yl)-urea | 0.67 | 459.41 |
| 36 | 1-[2-(4-Benzyl-4-hydroxy-piperidin-1-yl)-ethyl]-3-{2-[2-(4-fluoro-phenyl)-ethyl]-pyridin-4-yl}-urea | 0.68 | 477.44 |
| 37 | 1-{2-[3-(2-Methyl-6-phenethyl-pyridin-4-yl)-ureido]-ethyl}-4-phenyl-piperidine-4-carboxylic acid benzyl-methyl-amide | 0.79 | 590.53 |
| 38 | 1-[2-(4-Benzyl-piperidin-1-yl)-ethyl]-3-{2-[2-(4-fluoro-phenyl)-ethyl]-6-methyl-pyridin-4-yl}-urea | 0.75 | 475.49 |

Example 39

1-[2-(4-Benzyl-piperidin-1-yl)-ethyl]-3-(2-methyl-pyridin-4-yl)-urea

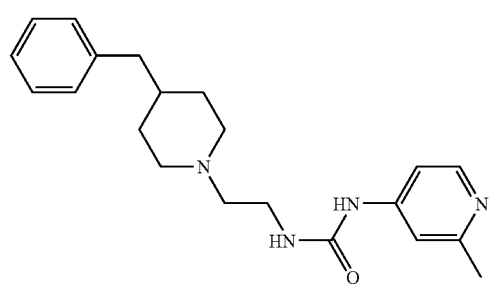

Example 39.2

1-[2-(4-Benzyl-piperidin-1-yl)-ethyl]-3-(2-methyl-pyridin-4-yl)-urea

The crude 1-[2-(4-benzyl-piperidin-1-yl)-2-oxo-ethyl]-3-(2-methyl-pyridin-4-yl)-urea (Example 39.1., 0.5 mmol) is dissolved in THF (5 mL) and added to a cooled (0° C.) suspension of $LiAlH_4$ (100 mg, 2.5 mmol) in THF (20 mL). The mixture is warmed during 15 h to r.t. The reaction mixture is carefully added to EtOAc (100 mL) and MeOH (5 mL), and, subsequently, sat. aq. $NaHCO_3$ (2 mL) are added. The mixture is filtered, the filtercake washed with MeOH (2×50 mL), and the filtrate is evaporated. The residue is taken up in a minimal amount of MeOH, diluted with $CH_2Cl_2$, dried ($Na_2SO_4$), filtered and evaporated. The residue is purified by HPLC to provide the title compound.

| Example No | Example | $t_R$ | [M + H]$^+$ |
|---|---|---|---|
| 39 | 1-[2-(4-Benzyl-piperidin-1-yl)-ethyl]-3-(2-methyl-pyridin-4-yl)-urea | 0.62 | 353.12 |

Example 40

1-[2-(4-Benzyl-4-hydroxy-piperidin-1-yl)-ethyl]-3-(2-benzyl-pyridin-4-yl)-urea

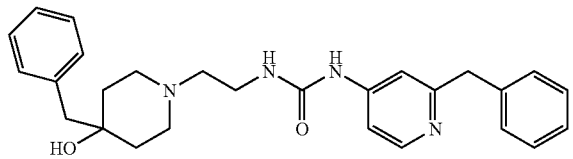

Example 40.1

1-[2-(4-Benzyl-4-hydroxy-piperidin-1-yl)-ethyl]-3-(2-chloro-pyridin-4-yl)-urea

The title compound is prepared from 2-(4-benzylpiperidino)-1-ethanamine (Example B1.) and 2-chloro-4-isocyanatopyridine (Example C11.) using the method described in Example 17.

Example 40.2

1-[2-(4-Benzyl-4-hydroxy-piperidin-1-yl)-ethyl]-3-(2-benzyl-pyridin-4-yl)-urea

A mixture of 1-[2-(4-benzyl-4-hydroxy-piperidin-1-yl)-ethyl]-3-(2-chloro-pyridin-4-yl)-urea (98 mg, 0.3 mmol), B-benzyl-9-BBN (0.5 M in THF, 4 mL, 2 mmol), triphenylphosphine (29 mg, 0.11 mmol), tetrakis(triphenylphosphine)palladium(0) (11 mg, 0.01 mmol), 2 M aq. $K_2CO_3$ (0.5 mL) and dimethoxyethane (1 mL) is degassed and heated under argon at 90° C. for 7 days. The mixture is evaporated and the residue purified by preparative HPLC to provide the title compound.

| Example No | Example | $t_R$ | [M + H]$^+$ |
|---|---|---|---|
| 40 | 1-[2-(4-Benzyl-4-hydroxy-piperidin-1-yl)-ethyl]-3-(2-benzyl-pyridin-4-yl)-urea | 0.65 | 445.4 |

Example 41

N-(1-{2-[3-(2-Ethyl-6-methyl-pyridin-4-yl)-ureido]-ethyl}-piperidin-4-yl)-4-fluoro-N-propyl-benzenesulfonamide

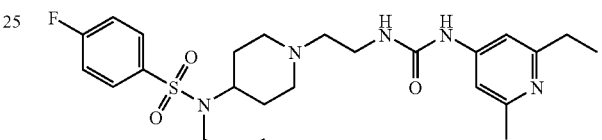

To a solution of (2-ethyl-6-methyl-pyridin-4-yl)-carbamic acid pentafluorophenyl ester (Example C13., 0.2M, 3 mL, 0.6 mmol) is added a solution of N-[1-(2-amino-ethyl)-piperidin-4-yl]-4-fluoro-N-propyl-benzenesulfonamide (Example B6., 182 mg, 0.53 mmol). The mixture is stirred at r.t. for 15 h. The mixture is evaporated and the residue purified by HPLC to provide the title compound.

The following compounds are prepared from Examples B4.-B6. or B10.-B11. and Examples C13. or C14. using the method described for Example 41.

| Example No | Example | $t_R$ | [M + H]$^+$ |
|---|---|---|---|
| 41 | N-(1-{2-[3-(2-Ethyl-6-methyl-pyridin-4-yl)-ureido]-ethyl}-piperidin-4-yl)-4-fluoro-N-propyl-benzenesulfonamide | 0.69 | 506.27 |
| 42 | 4-Bromo-N-ethyl-N-(1-{2-[3-(2-ethyl-6-methyl-pyridin-4-yl)-ureido]-ethyl}-piperidin-4-yl)-benzenesulfonamide | 0.7 | 554.2 |
| 43 | N-(1-{2-[3-(2-Ethyl-6-methyl-pyridin-4-yl)-ureido]-ethyl}-piperidin-4-yl)-4-methoxy-N-propyl-benzenesulfonamide | 0.69 | 518.23 |
| 44 | 1-{2-[3-(2-Ethyl-6-methyl-pyridin-4-yl)-ureido]-ethyl}-4-methyl-piperidine-4-carboxylic acid benzyl-methyl-amide | 0.65 | 452.35 |
| 45 | 1-{2-[3-(2-Ethyl-6-methyl-pyridin-4-yl)-ureido]-ethyl}-4-methyl-piperidine-4-carboxylic acid (4-methoxy-benzyl)-methyl-amide | 0.65 | 482.32 |
| 46 | 1-{2-[3-(2,6-Dimethyl-pyridin-4-yl)-ureido]-ethyl}-4-methyl-piperidine-4-carboxylic acid benzyl-methyl-amide | 0.63 | 438.22 |
| 47 | 1-{2-[3-(2,6-Dimethyl-pyridin-4-yl)-ureido]-ethyl}-4-methyl-piperidine-4-carboxylic acid (4-methoxy-benzyl)-methyl-amide | 0.64 | 468.27 |

Example 48

N-(1-{2-[3-(2,6-Dimethyl-pyridin-4-yl)-ureido]-ethyl}-piperidin-4-yl)-N-methyl-benzenesulfonamide

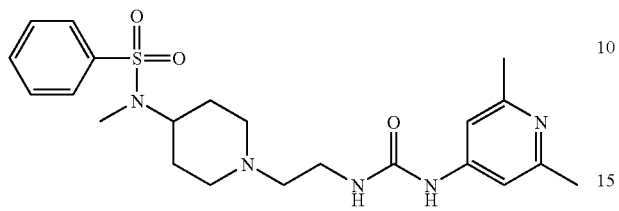

To a cooled (0° C.) mixture of 1-(2,6-dimethyl-pyridin-4-yl)-3-[2-(4-methylamino-piperidin-1-yl)-ethyl]-urea (Example E1., 0.3 mmol) and TEA (0.5 mL, 0.35 mmol) in CH$_2$Cl$_2$ (2 mL) is added a solution of benzenesulfonyl chloride (53.0 mg, 0.3 mmol) in CH$_2$Cl$_2$ (1 mL). The mixture is stirred at r.t. for 15 h and evaporated. the residue is purified by HPLC to provide the title compound.

The following compounds are prepared from Examples E1.-E4. using the method described for Example 48.

| Example No | Example | $t_R$ | [M + H]$^+$ |
|---|---|---|---|
| 48 | N-(1-{2-[3-(2,6-Dimethyl-pyridin-4-yl)-ureido]-ethyl}-piperidin-4-yl)-N-methyl-benzenesulfonamide | 0.61 | 446.11 |
| 49 | N-(1-{2-[3-(2,6-Dimethyl-pyridin-4-yl)-ureido]-ethyl}-piperidin-4-yl)-4-methoxy-N-methyl-benzenesulfonamide | 0.63 | 476.12 |
| 50 | N-(1-{2-[3-(2,6-Dimethyl-pyridin-4-yl)-ureido]-ethyl}-piperidin-4-yl)-3-methoxy-N-methyl-benzenesulfonamide | 0.64 | 476.13 |
| 51 | N-(1-{2-[3-(2,6-Dimethyl-pyridin-4-yl)-ureido]-ethyl}-piperidin-4-yl)-2,5-dimethoxy-N-methyl-benzenesulfonamide | 0.64 | 506.15 |
| 52 | N-(1-{2-[3-(2,6-Dimethyl-pyridin-4-yl)-ureido]-ethyl}-piperidin-4-yl)-3,4-dimethoxy-N-methyl-benzenesulfonamide | 0.62 | 506.13 |
| 53 | N-(1-{2-[3-(2,6-Dimethyl-pyridin-4-yl)-ureido]-ethyl}-piperidin-4-yl)-2-methoxy-4,N-dimethyl-benzenesulfonamide | 0.64 | 490.12 |
| 54 | N-(1-{2-[3-(2,6-Dimethyl-pyridin-4-yl)-ureido]-ethyl}-piperidin-4-yl)-4-fluoro-N-methyl-benzenesulfonamide | 0.63 | 464.09 |
| 55 | N-(1-{2-[3-(2,6-Dimethyl-pyridin-4-yl)-ureido]-ethyl}-piperidin-4-yl)-3-fluoro-N-methyl-benzenesulfonamide | 0.63 | 464.08 |
| 56 | N-(1-{2-[3-(2,6-Dimethyl-pyridin-4-yl)-ureido]-ethyl}-piperidin-4-yl)-2-fluoro-N-methyl-benzenesulfonamide | 0.62 | 464.08 |
| 57 | N-(1-{2-[3-(2,6-Dimethyl-pyridin-4-yl)-ureido]-ethyl}-piperidin-4-yl)-2,4-difluoro-N-methyl-benzenesulfonamide | 0.64 | 482.08 |
| 58 | N-(1-{2-[3-(2,6-Dimethyl-pyridin-4-yl)-ureido]-ethyl}-piperidin-4-yl)-3,4-difluoro-N-methyl-benzenesulfonamide | 0.66 | 482.07 |
| 59 | N-(1-{2-[3-(2,6-Dimethyl-pyridin-4-yl)-ureido]-ethyl}-piperidin-4-yl)-2,6-difluoro-N-methyl-benzenesulfonamide | 0.63 | 482.07 |
| 60 | N-(1-{2-[3-(2,6-Dimethyl-pyridin-4-yl)-ureido]-ethyl}-piperidin-4-yl)-4-ethyl-N-methyl-benzenesulfonamide | 0.68 | 474.13 |
| 61 | N-{4-[(1-{2-[3-(2,6-Dimethyl-pyridin-4-yl)-ureido]-ethyl}-piperidin-4-yl)-methyl-sulfamoyl]-phenyl}-acetamide | 0.6 | 503.13 |
| 62 | N-(1-{2-[3-(2,6-Dimethyl-pyridin-4-yl)-ureido]-ethyl}-piperidin-4-yl)-4-isopropoxy-N-methyl-benzenesulfonamide | 0.69 | 504.16 |
| 63 | N-(1-{2-[3-(2,6-Dimethyl-pyridin-4-yl)-ureido]-ethyl}-piperidin-4-yl)-4,N-dimethyl-benzenesulfonamide | 0.64 | 460.1 |
| 64 | N-(1-{2-[3-(2,6-Dimethyl-pyridin-4-yl)-ureido]-ethyl}-piperidin-4-yl)-3,N-dimethyl-benzenesulfonamide | 0.65 | 460.11 |
| 65 | N-(1-{2-[3-(2,6-Dimethyl-pyridin-4-yl)-ureido]-ethyl}-piperidin-4-yl)-2,N-dimethyl-benzenesulfonamide | 0.64 | 460.11 |
| 66 | N-(1-{2-[3-(2,6-Dimethyl-pyridin-4-yl)-ureido]-ethyl}-piperidin-4-yl)-4-methoxy-2,3,6,N-tetramethyl-benzenesulfonamide | 0.71 | 518.16 |

-continued

| Example No | Example | $t_R$ | $[M + H]^+$ |
|---|---|---|---|
| 67 | 4-Chloro-N-(1-{2-[3-(2,6-dimethyl-pyridin-4-yl)-ureido]-ethyl}-piperidin-4-yl)-N-methyl-benzenesulfonamide | 0.66 | 480.06 |
| 68 | 3-Chloro-N-(1-{2-[3-(2,6-dimethyl-pyridin-4-yl)-ureido]-ethyl}-piperidin-4-yl)-N-methyl-benzenesulfonamide | 0.66 | 480.05 |
| 69 | 2-Chloro-N-(1-{2-[3-(2,6-dimethyl-pyridin-4-yl)-ureido]-ethyl}-piperidin-4-yl)-N-methyl-benzenesulfonamide | 0.64 | 480.05 |
| 70 | 3,4-Dichloro-N-(1-{2-[3-(2,6-dimethyl-pyridin-4-yl)-ureido]-ethyl}-piperidin-4-yl)-N-methyl-benzenesulfonamide | 0.70 | 514.03 |
| 71 | N-(1-{2-[3-(2,6-Dimethyl-pyridin-4-yl)-ureido]-ethyl}-piperidin-4-yl)-N-methyl-4-trifluoromethyl-benzenesulfonamide | 0.70 | 514.11 |
| 72 | N-(1-{2-[3-(2,6-Dimethyl-pyridin-4-yl)-ureido]-ethyl}-piperidin-4-yl)-N-methyl-3-trifluoromethyl-benzenesulfonamide | 0.70 | 514.1 |
| 73 | Thiophene-2-sulfonic acid (1-{2-[3-(2,6-dimethyl-pyridin-4-yl)-ureido]-ethyl}-piperidin-4-yl)-methyl-amide | 0.61 | 452.05 |
| 74 | 5-Chloro-thiophene-2-sulfonic acid (1-{2-[3-(2,6-dimethyl-pyridin-4-yl)-ureido]-ethyl}-piperidin-4-yl)-methyl-amide | 0.66 | 486 |
| 75 | 2,5-Dichloro-thiophene-3-sulfonic acid (1-{2-[3-(2,6-dimethyl-pyridin-4-yl)-ureido]-ethyl}-piperidin-4-yl)-methyl-amide | 0.68 | 519.99 |
| 76 | N-(1-{2-[3-(2,6-Dimethyl-pyridin-4-yl)-ureido]-ethyl}-piperidin-4-yl)-N-ethyl-benzenesulfonamide | 0.64 | 460.29 |
| 77 | N-(1-{2-[3-(2,6-Dimethyl-pyridin-4-yl)-ureido]-ethyl}-piperidin-4-yl)-N-ethyl-3-fluoro-benzenesulfonamide | 0.66 | 478.11 |
| 78 | N-(1-{2-[3-(2,6-Dimethyl-pyridin-4-yl)-ureido]-ethyl}-piperidin-4-yl)-N-ethyl-2-fluoro-benzenesulfonamide | 0.65 | 478.12 |
| 79 | N-(1-{2-[3-(2,6-Dimethyl-pyridin-4-yl)-ureido]-ethyl}-piperidin-4-yl)-N-ethyl-2,4-difluoro-benzenesulfonamide | 0.67 | 496.14 |
| 80 | N-(1-{2-[3-(2,6-Dimethyl-pyridin-4-yl)-ureido]-ethyl}-piperidin-4-yl)-N-ethyl-3,4-difluoro-benzenesulfonamide | 0.68 | 496.12 |
| 81 | N-(1-{2-[3-(2,6-Dimethyl-pyridin-4-yl)-ureido]-ethyl}-piperidin-4-yl)-N-ethyl-2,6-difluoro-benzenesulfonamide | 0.65 | 496.13 |
| 82 | N-(1-{2-[3-(2,6-Dimethyl-pyridin-4-yl)-ureido]-ethyl}-piperidin-4-yl)-4,N-diethyl-benzenesulfonamide | 0.7 | 488.15 |
| 83 | N-(1-{2-[3-(2,6-Dimethyl-pyridin-4-yl)-ureido]-ethyl}-piperidin-4-yl)-N-ethyl-4-isopropoxy-benzenesulfonamide | 0.71 | 518.19 |
| 84 | N-(1-{2-[3-(2,6-Dimethyl-pyridin-4-yl)-ureido]-ethyl}-piperidin-4-yl)-N-ethyl-4-methyl-benzenesulfonamide | 0.67 | 474.14 |
| 85 | N-(1-{2-[3-(2,6-Dimethyl-pyridin-4-yl)-ureido]-ethyl}-piperidin-4-yl)-N-ethyl-3-methyl-benzenesulfonamide | 0.67 | 474.13 |
| 86 | N-(1-{2-[3-(2,6-Dimethyl-pyridin-4-yl)-ureido]-ethyl}-piperidin-4-yl)-N-ethyl-2-methyl-benzenesulfonamide | 0.66 | 474.14 |
| 87 | N-(1-{2-[3-(2,6-Dimethyl-pyridin-4-yl)-ureido]-ethyl}-piperidin-4-yl)-N-ethyl-4-methoxy-2,3,6-trimethyl-benzenesulfonamide | 0.72 | 532.19 |
| 88 | 4-Chloro-N-(1-{2-[3-(2,6-dimethyl-pyridin-4-yl)-ureido]-ethyl}-piperidin-4-yl)-N-ethyl-benzenesulfonamide | 0.68 | 494.11 |
| 89 | 3-Chloro-N-(1-{2-[3-(2,6-dimethyl-pyridin-4-yl)-ureido]-ethyl}-piperidin-4-yl)-N-ethyl-benzenesulfonamide | 0.69 | 494.1 |
| 90 | 2-Chloro-N-(1-{2-[3-(2,6-dimethyl-pyridin-4-yl)-ureido]-ethyl}-piperidin-4-yl)-N-ethyl-benzenesulfonamide | 0.66 | 494.09 |
| 91 | 3,4-Dichloro-N-(1-{2-[3-(2,6-dimethyl-pyridin-4-yl)-ureido]-ethyl}-piperidin-4-yl)-N-ethyl-benzenesulfonamide | 0.72 | 528.03 |
| 92 | N-(1-{2-[3-(2,6-Dimethyl-pyridin-4-yl)-ureido]-ethyl}-piperidin-4-yl)-N-ethyl-4-trifluoromethyl-benzenesulfonamide | 0.71 | 528.1 |

-continued

| Example No | Example | $t_R$ | $[M + H]^+$ |
|---|---|---|---|
| 93 | N-(1-{2-[3-(2,6-Dimethyl-pyridin-4-yl)-ureido]-ethyl}-piperidin-4-yl)-N-ethyl-3-trifluoromethyl-benzenesulfonamide | 0.71 | 528.12 |
| 94 | N-(1-{2-[3-(2,6-Dimethyl-pyridin-4-yl)-ureido]-ethyl}-piperidin-4-yl)-N-ethyl-2-trifluoromethyl-benzenesulfonamide | 0.69 | 528.11 |
| 95 | Thiophene-2-sulfonic acid (1-{2-[3-(2,6-dimethyl-pyridin-4-yl)-ureido]-ethyl}-piperidin-4-yl)-ethyl-amide | 0.63 | 466.08 |
| 96 | 5-Chloro-thiophene-2-sulfonic acid (1-{2-[3-(2,6-dimethyl-pyridin-4-yl)-ureido]-ethyl}-piperidin-4-yl)-ethyl-amide | 0.69 | 500.07 |
| 97 | 2,5-Dichloro-thiophene-3-sulfonic acid (1-{2-[3-(2,6-dimethyl-pyridin-4-yl)-ureido]-ethyl}-piperidin-4-yl)-ethyl-amide | 0.71 | 533.98 |
| 98 | N-(1-{2-[3-(2,6-Dimethyl-pyridin-4-yl)-ureido]-ethyl}-piperidin-4-yl)-N-ethyl-2,5-dimethoxy-benzenesulfonamide | 0.65 | 520.28 |
| 99 | 5-Bromo-N-(1-{2-[3-(2,6-dimethyl-pyridin-4-yl)-ureido]-ethyl}-piperidin-4-yl)-N-ethyl-2-methoxy-benzenesulfonamide | 0.69 | 568.2 |
| 100 | N-(1-{2-[3-(2,6-Dimethyl-pyridin-4-yl)-ureido]-ethyl}-piperidin-4-yl)-N-ethyl-2-methoxy-4-methyl-benzenesulfonamide | 0.67 | 504.28 |
| 101 | N-(1-{2-[3-(2,6-Dimethyl-pyridin-4-yl)-ureido]-ethyl}-piperidin-4-yl)-N-ethyl-3,4-dimethoxy-benzenesulfonamide | 0.65 | 520.29 |
| 102 | N-(1-{2-[3-(2,6-Dimethyl-pyridin-4-yl)-ureido]-ethyl}-piperidin-4-yl)-N-ethyl-3-methoxy-benzenesulfonamide | 0.67 | 490.27 |
| 103 | N-Cyclopropyl-N-(1-{2-[3-(2,6-dimethyl-pyridin-4-yl)-ureido]-ethyl}-piperidin-4-yl)-benzenesulfonamide | 0.65 | 472.16 |
| 104 | N-Cyclopropyl-N-(1-{2-[3-(2,6-dimethyl-pyridin-4-yl)-ureido]-ethyl}-piperidin-4-yl)-3-fluoro-benzenesulfonamide | 0.67 | 490.15 |
| 105 | N-Cyclopropyl-N-(1-{2-[3-(2,6-dimethyl-pyridin-4-yl)-ureido]-ethyl}-piperidin-4-yl)-2-fluoro-benzenesulfonamide | 0.65 | 490.11 |
| 106 | N-Cyclopropyl-N-(1-{2-[3-(2,6-dimethyl-pyridin-4-yl)-ureido]-ethyl}-piperidin-4-yl)-2,4-difluoro-benzenesulfonamide | 0.67 | 508.12 |
| 107 | N-Cyclopropyl-N-(1-{2-[3-(2,6-dimethyl-pyridin-4-yl)-ureido]-ethyl}-piperidin-4-yl)-3,4-difluoro-benzenesulfonamide | 0.69 | 508.11 |
| 108 | N-Cyclopropyl-N-(1-{2-[3-(2,6-dimethyl-pyridin-4-yl)-ureido]-ethyl}-piperidin-4-yl)-2,6-difluoro-benzenesulfonamide | 0.66 | 508.13 |
| 109 | N-Cyclopropyl-N-(1-{2-[3-(2,6-dimethyl-pyridin-4-yl)-ureido]-ethyl}-piperidin-4-yl)-4-ethyl-benzenesulfonamide | 0.71 | 500.17 |
| 110 | N-(4-[Cyclopropyl-(1-{2-[3-(2,6-dimethyl-pyridin-4-yl)-ureido]-ethyl}-piperidin-4-yl)-sulfamoyl]-phenyl}-acetamide | 0.63 | 529.05 |
| 111 | N-Cyclopropyl-N-(1-{2-[3-(2,6-dimethyl-pyridin-4-yl)-ureido]-ethyl}-piperidin-4-yl)-4-isopropoxy-benzenesulfonamide | 0.71 | 530.15 |
| 112 | N-Cyclopropyl-N-(1-{2-[3-(2,6-dimethyl-pyridin-4-yl)-ureido]-ethyl}-piperidin-4-yl)-4-methyl-benzenesulfonamide | 0.68 | 486.1 |
| 113 | N-Cyclopropyl-N-(1-{2-[3-(2,6-dimethyl-pyridin-4-yl)-ureido]-ethyl}-piperidin-4-yl)-3-methyl-benzenesulfonamide | 0.68 | 486.13 |
| 114 | N-Cyclopropyl-N-(1-{2-[3-(2,6-dimethyl-pyridin-4-yl)-ureido]-ethyl}-piperidin-4-yl)-2-methyl-benzenesulfonamide | 0.67 | 486.09 |
| 115 | 4-Chloro-N-cyclopropyl-N-(1-{2-[3-(2,6-dimethyl-pyridin-4-yl)-ureido]-ethyl}-piperidin-4-yl)-benzenesulfonamide | 0.69 | 506.11 |
| 116 | 3-Chloro-N-cyclopropyl-N-(1-{2-[3-(2,6-dimethyl-pyridin-4-yl)-ureido]-ethyl}-piperidin-4-yl)-benzenesulfonamide | 0.69 | 506.08 |
| 117 | 2-Chloro-N-cyclopropyl-N-(1-{2-[3-(2,6-dimethyl-pyridin-4-yl)-ureido]-ethyl}-piperidin-4-yl)-benzenesulfonamide | 0.67 | 506.1 |

-continued

| Example No | Example | $t_R$ | $[M + H]^+$ |
|---|---|---|---|
| 118 | 3,4-Dichloro-N-cyclopropyl-N-(1-{2-[3-(2,6-dimethyl-pyridin-4-yl)-ureido]-ethyl}-piperidin-4-yl)-benzenesulfonamide | 0.73 | 540.03 |
| 119 | N-Cyclopropyl-N-(1-{2-[3-(2,6-dimethyl-pyridin-4-yl)-ureido]-ethyl}-piperidin-4-yl)-4-trifluoromethyl-benzenesulfonamide | 0.72 | 540.12 |
| 120 | N-Cyclopropyl-N-(1-{2-[3-(2,6-dimethyl-pyridin-4-yl)-ureido]-ethyl}-piperidin-4-yl)-3-trifluoromethyl-benzenesulfonamide | 0.72 | 540.04 |
| 121 | N-Cyclopropyl-N-(1-{2-[3-(2,6-dimethyl-pyridin-4-yl)-ureido]-ethyl}-piperidin-4-yl)-2-trifluoromethyl-benzenesulfonamide | 0.7 | 540.07 |
| 122 | Thiophene-2-sulfonic acid cyclopropyl-(1-{2-[3-(2,6-dimethyl-pyridin-4-yl)-ureido]-ethyl}-piperidin-4-yl)-amide | 0.64 | 478.06 |
| 123 | 5-Chloro-thiophene-2-sulfonic acid cyclopropyl-(1-{2-[3-(2,6-dimethyl-pyridin-4-yl)-ureido]-ethyl}-piperidin-4-yl)-amide | 0.7 | 512.05 |
| 124 | 2,5-Dichloro-thiophene-3-sulfonic acid cyclopropyl-(1-{2-[3-(2,6-dimethyl-pyridin-4-yl)-ureido]-ethyl}-piperidin-4-yl)-amide | 0.71 | 545.94 |
| 125 | N-Cyclopropyl-N-(1-{2-[3-(2,6-dimethyl-pyridin-4-yl)-ureido]-ethyl}-piperidin-4-yl)-4-methoxy-benzenesulfonamide | 0.66 | 502.29 |
| 126 | N-Cyclopropyl-N-(1-{2-[3-(2,6-dimethyl-pyridin-4-yl)-ureido]-ethyl}-piperidin-4-yl)-3-methoxy-benzenesulfonamide | 0.67 | 502.27 |
| 127 | N-Cyclopropyl-N-(1-{2-[3-(2,6-dimethyl-pyridin-4-yl)-ureido]-ethyl}-piperidin-4-yl)-2,5-dimethoxy-benzenesulfonamide | 0.67 | 532.25 |
| 128 | N-Cyclopropyl-N-(1-{2-[3-(2,6-dimethyl-pyridin-4-yl)-ureido]-ethyl}-piperidin-4-yl)-2-methoxy-4-methyl-benzenesulfonamide | 0.67 | 516.3 |
| 129 | N-Ethyl-N-(1-{2-[3-(2-ethyl-6-methyl-pyridin-4-yl)-ureido]-ethyl}-piperidin-4-yl)-2-methoxy-4-methyl-benzenesulfonamide | 0.68 | 518.27 |
| 130 | N-Ethyl-N-(1-{2-[3-(2-ethyl-6-methyl-pyridin-4-yl)-ureido]-ethyl}-piperidin-4-yl)-3,4-dimethoxy-benzenesulfonamide | 0.66 | 534.25 |
| 131 | N-Ethyl-N-(1-{2-[3-(2-ethyl-6-methyl-pyridin-4-yl)-ureido]-ethyl}-piperidin-4-yl)-3-methoxy-benzenesulfonamide | 0.68 | 504.27 |

Example 132

2-(3,4-Dichloro-phenyl)-N-(1-{2-[3-(2,6-dimethyl-pyridin-4-yl)-ureido]-ethyl}-piperidin-4-yl)-N-methyl-acetamide

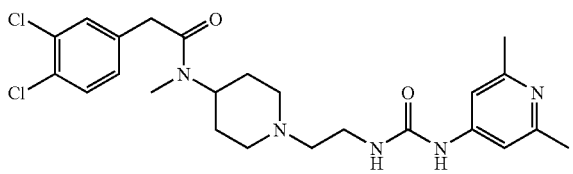

To a cooled (0° C.) mixture of 1-(2,6-dimethyl-pyridin-4-yl)-3-[2-(4-methylamino-piperidin-1-yl)-ethyl]-urea (Example E1., 0.3 mmol) and TEA (0.5 mL, 0.35 mmol) in CH$_2$Cl$_2$ (2 mL) is added a solution of (3,4-dichloro-phenyl)-acetyl chloride (67.0 mg, 0.3 mmol) in CH$_2$Cl$_2$ (1 mL). The mixture is stirred at r.t. for 15 h and evaporated. the residue is purified by HPLC to provide the title compound.

The following compounds are prepared from Examples E1.-E4. using the method described for Example 132.

| Example No | Example | $t_R$ | $[M + H]^+$ |
|---|---|---|---|
| 132 | 2-(3,4-Dichloro-phenyl)-N-(1-{2-[3-(2,6-dimethyl-pyridin-4-yl)-ureido]-ethyl}-piperidin-4-yl)-N-methyl-acetamide | 0.69 | 495.24 |

-continued

| Example No | Example | $t_R$ | $[M + H]^+$ |
|---|---|---|---|
| 133 | N-(1-{2-[3-(2,6-Dimethyl-pyridin-4-yl)-ureido]-ethyl}-piperidin-4-yl)-2-(2-methoxy-phenyl)-N-methyl-acetamide | 0.63 | 454.26 |
| 134 | 1-Phenyl-cyclopropanecarboxylic acid (1-{2-[3-(2,6-dimethyl-pyridin-4-yl)-ureido]-ethyl}-piperidin-4-yl)-methyl-amide | 0.63 | 450.23 |
| 135 | 1-(4-Chloro-phenyl)-cyclopropanecarboxylic acid (1-{2-[3-(2,6-dimethyl-pyridin-4-yl)-ureido]-ethyl}-piperidin-4-yl)-methyl-amide | 0.68 | 484.26 |
| 136 | 1-(4-Methoxy-phenyl)-cyclopropanecarboxylic acid (1-{2-[3-(2,6-dimethyl-pyridin-4-yl)-ureido]-ethyl}-piperidin-4-yl)-methyl-amide | 0.64 | 480.31 |
| 137 | 2-(3,4-Dimethoxy-phenyl)-N-(1-{2-[3-(2,6-dimethyl-pyridin-4-yl)-ureido]-ethyl}-piperidin-4-yl)-N-methyl-acetamide | 0.6 | 484.36 |
| 138 | 2-(4-Chloro-phenyl)-N-(1-{2-[3-(2,6-dimethyl-pyridin-4-yl)-ureido]-ethyl}-piperidin-4-yl)-N-methyl-acetamide | 0.66 | 458.23 |
| 139 | N-(1-{2-[3-(2,6-Dimethyl-pyridin-4-yl)-ureido]-ethyl}-piperidin-4-yl)-2-(4-fluoro-phenyl)-N-methyl-acetamide | 0.63 | 442.22 |
| 140 | N-(1-{2-[3-(2,6-Dimethyl-pyridin-4-yl)-ureido]-ethyl}-piperidin-4-yl)-N-methyl-2-phenyl-acetamide | 0.61 | 424.26 |
| 141 | N-(1-{2-[3-(2,6-Dimethyl-pyridin-4-yl)-ureido]-ethyl}-piperidin-4-yl)-N-methyl-2-pyridin-2-yl-acetamide | 0.47 | 425.23 |
| 142 | 2-(3-Chloro-phenyl)-N-(1-{2-[3-(2,6-dimethyl-pyridin-4-yl)-ureido]-ethyl}-piperidin-4-yl)-N-methyl-acetamide | 0.66 | 458.24 |
| 143 | 2-(2-Chloro-phenyl)-N-(1-{2-[3-(2,6-dimethyl-pyridin-4-yl)-ureido]-ethyl}-piperidin-4-yl)-N-methyl-acetamide | 0.64 | 458.21 |
| 144 | 2-(4-Chloro-phenyl)-N-ethyl-N-(1-{2-[3-(2-ethyl-6-methyl-pyridin-4-yl)-ureido]-ethyl}-piperidin-4-yl)-isobutyramide | 0.69 | 514.36 |
| 145 | 2-(2-Chloro-phenyl)-N-(1-{2-[3-(2,6-dimethyl-pyridin-4-yl)-ureido]-ethyl}-piperidin-4-yl)-N-ethyl-acetamide | 0.67 | 472.31 |
| 146 | 2-(3,4-Dichloro-phenyl)-N-(1-{2-[3-(2,6-dimethyl-pyridin-4-yl)-ureido]-ethyl}-piperidin-4-yl)-N-ethyl-acetamide | 0.71 | 506.2 |
| 147 | N-(1-{2-[3-(2,6-Dimethyl-pyridin-4-yl)-ureido]-ethyl}-piperidin-4-yl)-N-ethyl-2-(2-methoxy-phenyl)-acetamide | 0.65 | 468.31 |
| 148 | 2-(4-Chloro-phenyl)-N-(1-{2-[3-(2,6-dimethyl-pyridin-4-yl)-ureido]-ethyl}-piperidin-4-yl)-N-ethyl-isobutyramide | 0.7 | 500.31 |
| 149 | 1-Phenyl-cyclopropanecarboxylic acid (1-{2-[3-(2,6-dimethyl-pyridin-4-yl)-ureido]-ethyl}-piperidin-4-yl)-ethyl-amide | 0.64 | 464.31 |
| 150 | 1-(4-Chloro-phenyl)-cyclopropanecarboxylic acid (1-{2-[3-(2,6-dimethyl-pyridin-4-yl)-ureido]-ethyl}-piperidin-4-yl)-ethyl-amide | 0.68 | 498.3 |
| 151 | 1-(4-Methoxy-phenyl)-cyclopropanecarboxylic acid (1-{2-[3-(2,6-dimethyl-pyridin-4-yl)-ureido]-ethyl}-piperidin-4-yl)-ethyl-amide | 0.65 | 494.34 |
| 152 | N-(1-{2-[3-(2,6-Dimethyl-pyridin-4-yl)-ureido]-ethyl}-piperidin-4-yl)-N-ethyl-2-phenyl-acetamide | 0.62 | 438.27 |
| 153 | N-(1-{2-[3-(2,6-Dimethyl-pyridin-4-yl)-ureido]-ethyl}-piperidin-4-yl)-N-ethyl-2-(4-methoxy-phenyl)-acetamide | 0.62 | 468.31 |
| 154 | N-(1-{2-[3-(2,6-Dimethyl-pyridin-4-yl)-ureido]-ethyl}-piperidin-4-yl)-N-ethyl-4-methoxy-benzamide | 0.6 | 454.26 |
| 155 | N-(1-{2-[3-(2,6-Dimethyl-pyridin-4-yl)-ureido]-ethyl}-piperidin-4-yl)-N-ethyl-3,4-dimethoxy-benzamide | 0.59 | 454.26 |
| 156 | N-(1-{2-[3-(2,6-Dimethyl-pyridin-4-yl)-ureido]-ethyl}-piperidin-4-yl)-N-ethyl-4-fluoro-benzamide | 0.6 | 442.24 |
| 157 | N-(1-{2-[3-(2,6-Dimethyl-pyridin-4-yl)-ureido]-ethyl}-piperidin-4-yl)-N-ethyl-2-(3-methoxy-phenyl)-acetamide | 0.62 | 468.34 |
| 158 | 2-(3,4-Dimethoxy-phenyl)-N-(1-{2-[3-(2,6-dimethyl-pyridin-4-yl)-ureido]-ethyl}-piperidin-4-yl)-N-ethyl-acetamide | 0.61 | 498.38 |
| 159 | 2-(2,5-Dimethoxy-phenyl)-N-(1-{2-[3-(2,6-dimethyl-pyridin-4-yl)-ureido]-ethyl}-piperidin-4-yl)-N-ethyl-acetamide | 0.64 | 498.32 |
| 160 | N-(1-{2-[3-(2,6-Dimethyl-pyridin-4-yl)-ureido]-ethyl}-piperidin-4-yl)-N-ethyl-2-thiophen-2-yl-acetamide | 0.6 | 444.23 |

-continued

| Example No | Example | $t_R$ | $[M + H]^+$ |
|---|---|---|---|
| 161 | N-(1-{2-[3-(2,6-Dimethyl-pyridin-4-yl)-ureido]-ethyl}-piperidin-4-yl)-N-ethyl-2-(4-fluoro-phenyl)-acetamide | 0.63 | 456.3 |
| 162 | N-(1-{2-[3-(2,6-Dimethyl-pyridin-4-yl)-ureido]-ethyl}-piperidin-4-yl)-N-ethyl-benzamide | 0.58 | 424.23 |
| 163 | 1-Phenyl-cyclopropanecarboxylic acid ethyl-(1-{2-[3-(2-ethyl-6-methyl-pyridin-4-yl)-ureido]-ethyl}-piperidin-4-yl)-amide | 0.66 | 478.36 |
| 164 | 1-(4-Chloro-phenyl)-cyclopropanecarboxylic acid ethyl-(1-{2-[3-(2-ethyl-6-methyl-pyridin-4-yl)-ureido]-ethyl}-piperidin-4-yl)-amide | 0.7 | 512.27 |
| 165 | 1-(4-Methoxy-phenyl)-cyclopropanecarboxylic acid ethyl-(1-{2-[3-(2-ethyl-6-methyl-pyridin-4-yl)-ureido]-ethyl}-piperidin-4-yl)-amide | 0.67 | 508.32 |
| 166 | N-Ethyl-N-(1-{2-[3-(2-ethyl-6-methyl-pyridin-4-yl)-ureido]-ethyl}-piperidin-4-yl)-2-phenyl-acetamide | 0.64 | 452.3 |
| 167 | 2-(4-Chloro-phenyl)-N-ethyl-N-(1-{2-[3-(2-ethyl-6-methyl-pyridin-4-yl)-ureido]-ethyl}-piperidin-4-yl)-acetamide | 0.69 | 486.31 |
| 168 | 2-(4-Chloro-phenyl)-N-cyclopropyl-N-(1-{2-[3-(2,6-dimethyl-pyridin-4-yl)-ureido]-ethyl}-piperidin-4-yl)-isobutyramide | 0.69 | 512.4 |
| 169 | 1-(4-Methoxy-phenyl)-cyclopropanecarboxylic acid cyclopropyl-(1-{2-[3-(2,6-dimethyl-pyridin-4-yl)-ureido]-ethyl}-piperidin-4-yl)-amide | 0.67 | 506.35 |
| 170 | 2-(4-Chloro-phenyl)-N-cyclopropyl-N-(1-{2-[3-(2,6-dimethyl-pyridin-4-yl)-ureido]-ethyl}-piperidin-4-yl)-acetamide | 0.69 | 484.32 |
| 171 | 1-(4-Chloro-phenyl)-cyclopropanecarboxylic acid cyclopropyl-(1-{2-[3-(2,6-dimethyl-pyridin-4-yl)-ureido]-ethyl}-piperidin-4-yl)-amide | 0.7 | 510.31 |
| 172 | 1-Phenyl-cyclopropanecarboxylic acid cyclopropyl-(1-{2-[3-(2,6-dimethyl-pyridin-4-yl)-ureido]-ethyl}-piperidin-4-yl)-amide | 0.66 | 476.41 |

Example 173

N-(1-{2-[3-(2,6-Dimethyl-pyridin-4-yl)-ureido]-ethyl}-piperidin-4-yl)-N-ethyl-2-methoxy-benzenesulfonamide A suspension of 5-bromo-N-(1-{2-[3-(2,6-dimethyl-pyridin-4-yl)-ureido]-ethyl}-piperidin-4-yl)-N-ethyl-2-methoxy-benzenesulfonamide (Example 99, 30 mg, 0.05 mmol) and Pd—C (10%, 20 mg) in MeOH (10 mL) is stirred under hydrogen atmosphere for 15 h. The catalyst is filtered off and the reaction mixture evaporated to provide the title compound.

| Example No | Example | $t_R$ | $[M + H]^+$ |
|---|---|---|---|
| 173 | N-(1-{2-[3-(2,6-Dimethyl-pyridin-4-yl)-ureido]-ethyl}-piperidin-4-yl)-N-ethyl-2-methoxy-benzenesulfonamide | 0.64 | 490.13 |

Example 174

In Vitro Biological Characterization

The inhibitory activity of the compounds of General Formula 1 on the actions of urotensin II can be demonstrated using the test procedures described hereinafter:

1) Inhibition of Human [$^{125}$I]-Urotensin II Binding to a Rhabdomyosarcoma Cell Line Whole cell binding of human [$^{125}$I]-urotensin II is performed using human-derived TE-671 rhabdomyosarcoma cells (Deutsche Sammlung von Mikroorganismen und Zellkulturen, cell line #ACC-263), by methods adapted from a whole cell endothelin binding assay (Breu V et al, In vitro characterization of Ro-46-2005, a novel synthetic non-peptide antagonist of $ET_A$ and $ET_B$ receptors. FEBS Lett. 1993, 334, 210-214).

The assay is performed in 250 µL Dulbecco's Modified Eagle Medium, pH 7.4 (GIBCO BRL, Cat No 31885-023), including 25 mM HEPES (Fluka, Cat No 05473), 1.0% DMSO (Fluka, Cat No 41644) and 0.5% (w/v) BSA Fraction V (Fluka, Cat No 05473) in polypropylene microtiter plates (Nunc, Cat No 442587). 300,000 suspended cells are incubated with gentle shaking for 4 h at 20° C. with 20 pM human [$^{125}$I]Urotensin II (Anawa Trading SA, Wangen, Switzerland, 2130 Ci/mmol) and increasing concentrations of unlabeled antagonist. Minimum and maximum binding are derived from samples with and without 100 nM unlabelled U-II, respectively. After the 4 h incubation period, the cells are filtered onto GF/C filterplates (Packard, Cat No 6005174). The filter plates are dried, and then 50 µL scintillation cocktail (Packard, MicroScint 20, Cat No 6013621) is added to each well. The filterplates are counted in a microplate counter (Packard Bioscience, TopCount NXT).

All test compounds are dissolved and diluted in 100% DMSO. A ten-fold dilution into assay buffer is performed prior to addition to the assay. The final concentration of DMSO in the assay is 1.0%, which is found not to interfere with the binding. IC50 values are defined as the concentration of antagonist inhibiting 50% of the specific binding of [$^{125}$I] human U-II. Specific binding is the difference between maximum binding and minimum binding, as described above. An $IC_{50}$ value of 0.206 nM is found for unlabeled human U-II. The compounds of the invention are found to have $IC_{50}$ values ranging from 0.1 to 1000 nM in this assay.

2) Inhibition of Human [$^{125}$I]-Urotensin II Binding to Membranes from Recombinant Cells Carrying the Urotensin II-Receptor Membranes from CHO cells expressing human Urotensin II receptor were prepared as described before (Breu V. et al, FEBS Lett 1993; 334:210-214; Martine Clozel et. al., "Pharmacology of the Urotensin-II Receptor Antagonist ACT-058362: First Demonstration of a Pathophysiological Role of the Urotensin System", J Pharmacol Exp Ther. 2004; DOI: 10.1124/jpet.104.068320; WO-1999/40192). The binding assay was performed in 200 µl of PBS 1×pH 7.4 including 1 mM EDTA, 2.5% DMSO and 0.5% (w/v) BSA in polypropylene microtiter plates. Membranes containing 2-5 µg protein were incubated for 4 hours at room temperature with 20 pM (12000 cpm) [$^{125}$I]-Urotensin II and increasing concentrations of unlabeled antagonists. Minimum and maximum binding were derived from samples with and without 1 µM of unlabeled Urotensin II, respectively. After 4 hours of incubation, the membranes were filtered onto filterplates and washed 3 times with PBS 1×, 0.1% (w/v) BSA. 25 µl of scintillation cocktail was added to each well after drying the plates and the radioactivity on the filterplates was determined in a microplate counter.

The compounds of General Formula 1 are found to have $IC_{50}$ values ranging from 0.1 to 1000 nM in this assay. Preferred compounds of General Formula 1 have $IC_{50}$ values ranging from 0.1 to 100 nM. Most preferred compounds of General Formula 1 have $IC_{50}$ values ranging from 0.1 to 10 nM.

In the following table $IC_{50}$ values of compounds of General Formula 1 are summarized.

| Example No | Example | $IC_{50}$ [nM] |
|---|---|---|
| 2 | 1-{2-[3-(2,6-Dimethyl-pyridin-4-yl)-ureido]-ethyl}-4-phenyl-piperidine-4-carboxylic acid benzyl-methyl-amide | 0.7 |
| 41 | N-(1-{2-[3-(2-Ethyl-6-methyl-pyridin-4-yl)-ureido]-ethyl}-piperidin-4-yl)-4-fluoro-N-propyl-benzenesulfonamide | 0.4 |
| 74 | 5-Chloro-thiophene-2-sulfonic acid (1-{2-[3-(2,6-dimethyl-pyridin-4-yl)-ureido]-ethyl}-piperidin-4-yl)-methyl-amide | 0.5 |
| 96 | 5-Chloro-thiophene-2-sulfonic acid (1-{2-[3-(2,6-dimethyl-pyridin-4-yl)-ureido]-ethyl}-piperidin-4-yl)-ethyl-amide | 0.2 |
| 150 | 1-(4-Chloro-phenyl)-cyclopropanecarboxylic acid (1-{2-[3-(2,6-dimethyl-pyridin-4-yl)-ureido]-ethyl}-piperidin-4-yl)-ethyl-amide | 0.7 |

3) Inhibition of Human Urotensin II-Induced Contractions on Isolated Rat Thoracic Aorta:

Adult male rats (Wistar or Sprague-Dawley) are euthanized by $CO_2$. An aortic segment (12 mm) is isolated immediately distal to the left sub-clavian arterial branch, and vessel rings (3 mm wide) are prepared. The endothelium is removed by inserting the tip of a watchmaker's forceps inside the lumen and gently rolling the tissue on a moist filter paper. Aortic rings are suspended in tissue baths (10 mL) containing Krebs-Henseleit buffer of the following composition (mM): NaCl 115; KCl 4.7; $MgSO_4$ 1.2; $KH_2PO_4$ 1.5; $CaCl_2$ 2.5; $NaHCO_3$ 25; glucose 10. Bathing solution is maintained at 37° C. and aerated with 95% $O_2$/5% $CO_2$ (pH 7.4). A resting force of 2 g (19.6 mN) is applied to the vessel, and changes in force generation are recorded using an EMKA automated system (EMKA Technologies SA, Paris, France). The viability of each aortic ring is determined by contraction to a depolarising concentration of KCl (60 mM). After washout, the successful removal of endothelium is tested by the failure of acetylcholine (10 µM) to relax vessels constricted with phenylephrine (1 µM). Following further washout, tissues are exposed to either drug vehicle (control) or test compound for 20 minutes. A cumulative concentration-response curve to h-UII (30 pM-0.3 µM) is then obtained. Contraction of vessels to h-UII is expressed as a percentage of the initial contraction to KCl (60 mM). If the test compound displays competitive antagonism (causes parallel right-ward displacement of concentration-effect curve without diminishing the maximum response), then the inhibitory potency is quantified by calculation of the $pA_2$ value for the test compound ($pA_2$ value is the negative logarithm of the theoretical antagonist concentration which induces a two-fold shift in the $EC_{50}$ value for h-U-II).

The invention claimed is:

1. A compound of General Formula 2:

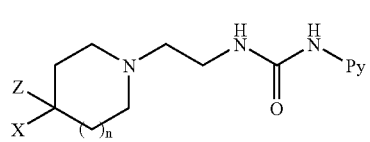

General Formula 2 wherein:
Py represents pyridin-4-yl which is disubstituted in positions 2 and 6, whereby the substituent in position 2 is $C_{1-7}$-alkyl or aryl-$C_{1-7}$-alkyl; and
the substituent in position 6 is methyl or ethyl;
X represents $R^1$—$SO_2NR^2$—; $R^1$—$CONR^2$—; aryl-$R^8$—$CONR^2$—; or $R^1$—$NR^3CONR^2$—;
Z represents hydrogen;
n represents the number 1;
$R^1$ represents aryl or aryl-$C_{1-7}$-alkyl;
$R^2$ represents hydrogen; $C_{1-7}$-alkyl; 2-hydroxyethyl; aryl-$C_{1-7}$-alkyl; or a saturated carbocyclic ring;
$R^3$ represents hydrogen or $C_{1-7}$-alkyl;
$R^8$ represents a saturated carbocyclic ring;
wherein
aryl means a group selected from the group consisting of 2-furyl; 2-thienyl; phenyl; 2-methylphenyl; 3-methylphenyl; 4-methylphenyl; 2-biphenyl; 3-biphenyl; 4-biphenyl; 2-methoxyphenyl; 3-methoxyphenyl; 4-methoxyphenyl; 3,4-dimethoxyphenyl; 2,6-dimethoxyphenyl; 2,5-dimethoxyphenyl; 2-phenoxyphenyl; 3-phenoxyphenyl; 4-phenoxyphenyl; 2-cyanophenyl; 3-cyanophenyl; 4-cyanophenyl; 2-fluorophenyl; 3-fluorophenyl; 4-fluorophenyl; 2,4-difluorophenyl; 2,5-difluorophenyl, 2,6-difluorophenyl; 3,4-difluorophenyl; 2-chlorophenyl; 3-chlorophenyl; 4-chlorophenyl; 3,4-dichlorophenyl; 2-bromophenyl; 3-bromophenyl; 4-bromophenyl; 2-trifluoromethylphenyl; 3-trifluoromethylphenyl; 4-trifluoromethylphenyl; 3,5-bis-trifluoromethylphenyl; 4-trifluoromethoxyphenyl; 4-ethylphenyl; 4-n-propylphenyl; 2-iso-propylphenyl; 4-iso-propylphenyl; 4-tert-butylphenyl; 4-n-pentylphenyl; 4-bromo-2-ethylphenyl; 2-methanesulfonylphenyl; 3-methanesulfonylphenyl; 4-methanesulfonylphenyl; 4-acetamidophenyl; 4-hydroxyphenyl; 4-isopropyloxyphenyl; 4-n-butoxyphenyl; 2-methoxy-4-methylphenyl; 4-methoxy-2,3,6-trimethylphenyl; 5-bromo-2-methoxy-phenyl; 2-pyridyl; 3-pyridyl; 4-pyridyl; 1-naphthyl; 2-naphthyl; 4-(pyrrol-1-yl)phenyl; 4-benzoylphenyl; 5-dimethylaminonaphth-1-yl; 5-chloro-3-methylthiophen-2-yl; 5-chloro-3-methyl-benzo[b]thiophen-2-yl; 3-(phenylsulfonyl)-thiophen-2-yl; 2-chloro-thien-5-yl; 2,5-dichloro-thien-3-yl; 4,5-dichlorothien-2-yl; 2-(2,2,2-trifluoroacetyl)-1-2,3,4-tetrahydroisoquinolin-7-yl; 4-(3-chloro-2-cyanophenyloxy)phenyl; 2-(5-benzamidomethyl)thiophenyl; 5-quinolyl; 6-quinolyl; 7-quinolyl; 8-quinolyl; (2-acetylamino-4-methyl)thiazol-5-yl; and 1-methylimidazol-4-yl; and aryl-$C_{1-7}$-alkyl means 3-phenylpropyl, phenethyl, benzyl, or benzyl substituted in the phenyl ring with $C_{1-7}$-alkyl, $C_{1-7}$-alkyl-O—, trifluoromethyl or halogen;

or pharmaceutically acceptable salts thereof.

2. The compound of General Formula 14 according to claim 1:

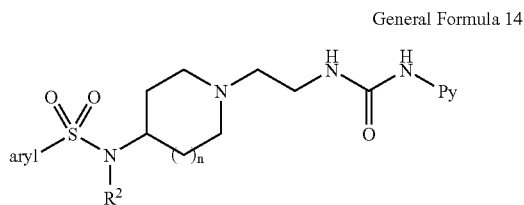

General Formula 14 wherein aryl, $R^2$, n and Py have the meaning given in General Formula 2;

or pharmaceutically acceptable salts thereof.

3. The compound of General Formula 17 according to claim 1:

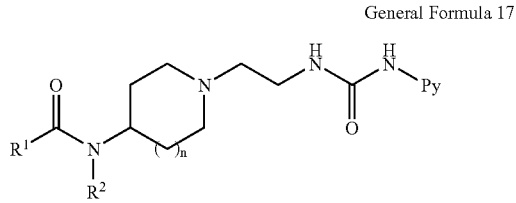

General Formula 17 wherein $R^1$, $R^2$, n and Py have the meaning given in General Formula 2;

or pharmaceutically acceptable salts thereof.

4. The compound of General Formula 19 according to claim 1:

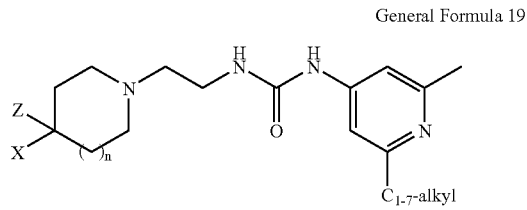

General Formula 19 wherein X, Z and n have the meaning given in General Formula 2;

or pharmaceutically acceptable salts thereof.

5. The compound of General Formula 20 according to claim 1:

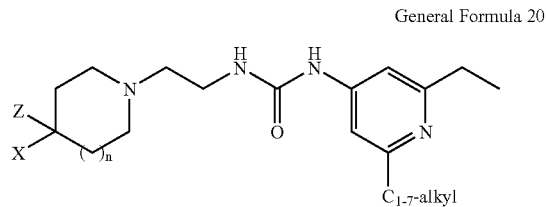

General Formula 20 wherein X, Z and n have the meaning given in General Formula 2;

or pharmaceutically acceptable salts thereof.

6. The compound of General Formula 21 according to claim 1:

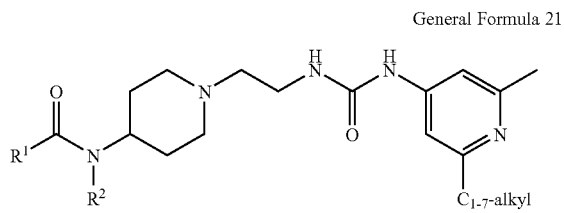

General Formula 21 wherein $R^1$ and $R^2$ have the meaning given in General Formula 2;

or pharmaceutically acceptable salts thereof.

7. The compound of General Formula 22 according to claim 1:

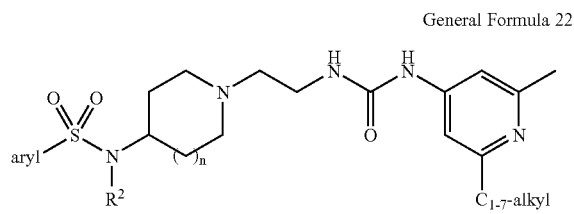

General Formula 22 wherein aryl, $R^2$ and n have the meaning given in General Formula 2;

or pharmaceutically acceptable salts thereof.

8. A compound selected from the group consisting of:
N-(1-{2-[3-(2,6-Dimethyl-pyridin-4-yl)-ureido]-ethyl}-piperidin-4-yl)-4-methoxy-N-propyl-benzenesulfonamide;
N-(1-{2-[3-(2,6-Dimethyl-pyridin-4-yl)-ureido]-ethyl}-piperidin-4-yl)-4-fluoro-N-propyl-benzenesulfonamide;
N-(1-{2-[3-(2,6-Dimethyl-pyridin-4-yl)-ureido]-ethyl}-piperidin-4-yl)-N-ethyl-4-methoxy-benzenesulfonamide;
N-(1-{2-[3-(2,6-Dimethyl-pyridin-4-yl)-ureido]-ethyl}-piperidin-4-yl)-N-ethyl-4-fluoro-benzenesulfonamide;
N-Ethyl-4-methoxy-N-(1-{2-[3-(2-methyl-6-phenethyl-pyridin-4-yl)-ureido]-ethyl}-piperidin-4-yl)-benzenesulfonamide;
N-Ethyl-4-methoxy-N-(1-{2-[3-(2-methyl-6-propyl-pyridin-4-yl)-ureido]-ethyl}-piperidin-4-yl)-benzenesulfonamide;

N-Ethyl-N-(1-{2-[3-(2-ethyl-6-methyl-pyridin-4-yl)-ureido]-ethyl}-piperidin-4-yl)-4-methoxy-benzenesulfonamide;

2-(4-Chloro-phenyl)-N-(1-{2-[3-(2,6-dimethyl-pyridin-4-yl)-ureido]-ethyl}-piperidin-4-yl)-N-ethyl-acetamide;

N-Cyclopropyl-N-(1-{2-[3-(2,6-dimethyl-pyridin-4-yl)-ureido]-ethyl}-piperidin-4-yl)-4-fluoro-benzenesulfonamide;

N-Ethyl-N-(1-{2-[3-(2-ethyl-6-methyl-pyridin-4-yl)-ureido]-ethyl}-piperidin-4-yl)-4-fluoro-benzenesulfonamide;

N-(1-{2-[3-(2,6-Diethyl-pyridin-4-yl)-ureido]-ethyl}-piperidin-4-yl)-N-ethyl-4-methoxy-benzenesulfonamide;

N-(1-{2-[3-(2,6-Diethyl-pyridin-4-yl)-ureido]-ethyl}-piperidin-4-yl)-N-ethyl-4-fluoro-benzenesulfonamide;

N-(1-{2-[3-(2-Ethyl-6-methyl-pyridin-4-yl)-ureido]-ethyl}-piperidin-4-yl)-4-fluoro-N-propyl-benzenesulfonamide;

4-Bromo-N-ethyl-N-(1-{2-[3-(2-ethyl-6-methyl-pyridin-4-yl)-ureido]-ethyl}-piperidin-4-yl)-benzenesulfonamide;

N-(1-{2-[3-(2-Ethyl-6-methyl-pyridin-4-yl)-ureido]-ethyl}-piperidin-4-yl)-4-methoxy-N-propyl-benzenesulfonamide;

N-(1-{2-[3-(2,6-Dimethyl-pyridin-4-yl)-ureido]-ethyl}-piperidin-4-yl)-4-methoxy-N-methyl-benzenesulfonamide;

N-(1-{2-[3-(2,6-Dimethyl-pyridin-4-yl)-ureido]-ethyl}-piperidin-4-yl)-4-ethyl-N-methyl-benzenesulfonamide;

N-{4-[(1-{2-[3-(2,6-Dimethyl-pyridin-4-yl)-ureido]-ethyl}-piperidin-4-yl)-methyl-sulfamoyl]-phenyl}-acetamide;

N-(1-{2-[3-(2,6-Dimethyl-pyridin-4-yl)-ureido]-ethyl}-piperidin-4-yl)-4-isopropoxy-N-methyl-benzenesulfonamide;

N-(1-{2-[3-(2,6-Dimethyl-pyridin-4-yl)-ureido]-ethyl}-piperidin-4-yl)-4,N-dimethyl-benzenesulfonamide;

4-Chloro-N-(1-{2-[3-(2,6-dimethyl-pyridin-4-yl)-ureido]-ethyl}-piperidin-4-yl)-N-methyl-benzenesulfonamide;

3,4-Dichloro-N-(1-{2-[3-(2,6-dimethyl-pyridin-4-yl)-ureido]-ethyl}-piperidin-4-yl)-N-methyl-benzenesulfonamide;

N-(1-{2-[3-(2,6-Dimethyl-pyridin-4-yl)-ureido]-ethyl}-piperidin-4-yl)-N-methyl-4-trifluoromethyl-benzenesulfonamide;

5-Chloro-thiophene-2-sulfonic acid (1-{2-[3-(2,6-dimethyl-pyridin-4-yl)-ureido]-ethyl}-piperidin-4-yl)-methyl-amide;

2,5-Dichloro-thiophene-3-sulfonic acid (1-{2-[3-(2,6-dimethyl-pyridin-4-yl)-ureido]-ethyl}-piperidin-4-yl)-methyl-amide;

N-(1-{2-[3-(2,6-Dimethyl-pyridin-4-yl)-ureido]-ethyl}-piperidin-4-yl)-N-ethyl-benzenesulfonamide;

N-(1-{2-[3-(2,6-Dimethyl-pyridin-4-yl)-ureido]-ethyl}-piperidin-4-yl)-N-ethyl-3-fluoro-benzenesulfonamide;

N-(1-{2-[3-(2,6-Dimethyl-pyridin-4-yl)-ureido]-ethyl}-piperidin-4-yl)-N-ethyl-2-fluoro-benzenesulfonamide;

N-(1-{2-[3-(2,6-Dimethyl-pyridin-4-yl)-ureido]-ethyl}-piperidin-4-yl)-N-ethyl-2,4-difluoro-benzenesulfonamide;

N-(1-{2-[3-(2,6-Dimethyl-pyridin-4-yl)-ureido]-ethyl}-piperidin-4-yl)-N-ethyl-3,4-difluoro-benzenesulfonamide;

N-(1-{2-[3-(2,6-Dimethyl-pyridin-4-yl)-ureido]-ethyl}-piperidin-4-yl)-N-ethyl-2,6-difluoro-benzenesulfonamide;

N-(1-{2-[3-(2,6-Dimethyl-pyridin-4-yl)-ureido]-ethyl}-piperidin-4-yl)-4,N-diethyl-benzenesulfonamide;

N-(1-{2-[3-(2,6-Dimethyl-pyridin-4-yl)-ureido]-ethyl}-piperidin-4-yl)-N-ethyl-4-isopropoxy-benzenesulfonamide;

N-(1-{2-[3-(2,6-Dimethyl-pyridin-4-yl)-ureido]-ethyl}-piperidin-4-yl)-N-ethyl-4-methyl-benzenesulfonamide;

N-(1-{2-[3-(2,6-Dimethyl-pyridin-4-yl)-ureido]-ethyl}-piperidin-4-yl)-N-ethyl-3-methyl-benzenesulfonamide;

N-(1-{2-[3-(2,6-Dimethyl-pyridin-4-yl)-ureido]-ethyl}-piperidin-4-yl)-N-ethyl-2-methyl-benzenesulfonamide;

N-(1-{2-[3-(2,6-Dimethyl-pyridin-4-yl)-ureido]-ethyl}-piperidin-4-yl)-N-ethyl-4-methoxy-2,3,6-trimethyl-benzenesulfonamide;

4-Chloro-N-(1-{2-[3-(2,6-dimethyl-pyridin-4-yl)-ureido]-ethyl}-piperidin-4-yl)-N-ethyl-benzenesulfonamide;

3-Chloro-N-(1-{2-[3-(2,6-dimethyl-pyridin-4-yl)-ureido]-ethyl}-piperidin-4-yl)-N-ethyl-benzenesulfonamide;

2-Chloro-N-(1-{2-[3-(2,6-dimethyl-pyridin-4-yl)-ureido]-ethyl}-piperidin-4-yl)-N-ethyl-benzenesulfonamide;

3,4-Dichloro-N-(1-{2-[3-(2,6-dimethyl-pyridin-4-yl)-ureido]-ethyl}-piperidin-4-yl)-N-ethyl-benzenesulfonamide;

N-(1-{2-[3-(2,6-Dimethyl-pyridin-4-yl)-ureido]-ethyl}-piperidin-4-yl)-N-ethyl-4-trifluoromethyl-benzenesulfonamide;

N-(1-{2-[3-(2,6-Dimethyl-pyridin-4-yl)-ureido]-ethyl}-piperidin-4-yl)-N-ethyl-3-trifluoromethyl-benzenesulfonamide;

N-(1-{2-[3-(2,6-Dimethyl-pyridin-4-yl)-ureido]-ethyl}-piperidin-4-yl)-N-ethyl-2-trifluoromethyl-benzenesulfonamide;

Thiophene-2-sulfonic acid (1-{2-[3-(2,6-dimethyl-pyridin-4-yl)-ureido]-ethyl}-piperidin-4-yl)-ethyl-amide;

5-Chloro-thiophene-2-sulfonic acid (1-{2-[3-(2,6-dimethyl-pyridin-4-yl)-ureido]-ethyl}-piperidin-4-yl)-ethyl-amide;

2,5-Dichloro-thiophene-3-sulfonic acid (1-{2-[3-(2,6-dimethyl-pyridin-4-yl)-ureido]-ethyl}-piperidin-4-yl)-ethyl-amide;

N-(1-{2-[3-(2,6-Dimethyl-pyridin-4-yl)-ureido]-ethyl}-piperidin-4-yl)-N-ethyl-2,5-dimethoxy-benzenesulfonamide;

5-Bromo-N-(1-{2-[3-(2,6-dimethyl-pyridin-4-yl)-ureido]-ethyl}-piperidin-4-yl)-N-ethyl-2-methoxy-benzenesulfonamide;

N-(1-{2-[3-(2,6-Dimethyl-pyridin-4-yl)-ureido]-ethyl}-piperidin-4-yl)-N-ethyl-2-methoxy-4-methyl-benzenesulfonamide;

N-(1-{2-[3-(2,6-Dimethyl-pyridin-4-yl)-ureido]-ethyl}-piperidin-4-yl)-N-ethyl-3,4-dimethoxy-benzenesulfonamide;

N-(1-{2-[3-(2,6-Dimethyl-pyridin-4-yl)-ureido]-ethyl}-piperidin-4-yl)-N-ethyl-3,4-dimethoxy-benzenesulfonamide;

N-(1-{2-[3-(2,6-Dimethyl-pyridin-4-yl)-ureido]-ethyl}-piperidin-4-yl)-N-ethyl-3-methoxy-benzenesulfonamide;

N-Cyclopropyl-N-(1-{2-[3-(2,6-dimethyl-pyridin-4-yl)-ureido]-ethyl}-piperidin-4-yl)-benzenesulfonamide;
N-Cyclopropyl-N-(1-{2-[3-(2,6-dimethyl-pyridin-4-yl)-ureido]-ethyl}-piperidin-4-yl)-3-fluoro-benzenesulfonamide;
N-Cyclopropyl-N-(1-{2-[3-(2,6-dimethyl-pyridin-4-yl)-ureido]-ethyl}-piperidin-4-yl)-2,4-difluoro-benzenesulfonamide;
N-Cyclopropyl-N-(1-{2-[3-(2,6-dimethyl-pyridin-4-yl)-ureido]-ethyl}-piperidin-4-yl)-2,6-difluoro-benzenesulfonamide;
N-Cyclopropyl-N-(1-{2-[3-(2,6-dimethyl-pyridin-4-yl)-ureido]-ethyl}-piperidin-4-yl)-4-ethyl-benzenesulfonamide;
N-Cyclopropyl-N-(1-{2-[3-(2,6-dimethyl-pyridin-4-yl)-ureido]-ethyl}-piperidin-4-yl)-4-isopropoxy-benzenesulfonamide;
N-Cyclopropyl-N-(1-{2-[3-(2,6-dimethyl-pyridin-4-yl)-ureido]-ethyl}-piperidin-4-yl)-4-methyl-benzenesulfonamide;
N-Cyclopropyl-N-(1-{2-[3-(2,6-dimethyl-pyridin-4-yl)-ureido]-ethyl}-piperidin-4-yl)-3-methyl-benzenesulfonamide;
4-Chloro-N-cyclopropyl-N-(1-{2-[3-(2,6-dimethyl-pyridin-4-yl)-ureido]-ethyl}-piperidin-4-yl)-benzenesulfonamide;
3-Chloro-N-cyclopropyl-N-(1-{2-[3-(2,6-dimethyl-pyridin-4-yl)-ureido]-ethyl}-piperidin-4-yl)-benzenesulfonamide;
2-Chloro-N-cyclopropyl-N-(1-{2-[3-(2,6-dimethyl-pyridin-4-yl)-ureido]-ethyl}-piperidin-4-yl)-benzenesulfonamide;
3,4-Dichloro-N-cyclopropyl-N-(1-{2-[3-(2,6-dimethyl-pyridin-4-yl)-ureido]-ethyl}-piperidin-4-yl)-benzenesulfonamide;
N-Cyclopropyl-N-(1-{2-[3-(2,6-dimethyl-pyridin-4-yl)-ureido]-ethyl}-piperidin-4-yl)-4-trifluoromethyl-benzenesulfonamide;
N-Cyclopropyl-N-(1-{2-[3-(2,6-dimethyl-pyridin-4-yl)-ureido]-ethyl}-piperidin-4-yl)-3-trifluoromethyl-benzenesulfonamide;
5-Chloro-thiophene-2-sulfonic acid cyclopropyl-(1-{2-[3-(2,6-dimethyl-pyridin-4-yl)-ureido]-ethyl}-piperidin-4-yl)-amide;
2,5-Dichloro-thiophene-3-sulfonic acid cyclopropyl-(1-{2-[3-(2,6-dimethyl-pyridin-4-yl)-ureido]-ethyl}-piperidin-4-yl)-amide;
N-Cyclopropyl-N-(1-{2-[3-(2,6-dimethyl-pyridin-4-yl)-ureido]-ethyl}-piperidin-4-yl)-4-methoxy-benzenesulfonamide;
N-Cyclopropyl-N-(1-{2-[3-(2,6-dimethyl-pyridin-4-yl)-ureido]-ethyl}-piperidin-4-yl)-3-methoxy-benzenesulfonamide;
N-Cyclopropyl-N-(1-{2-[3-(2,6-dimethyl-pyridin-4-yl)-ureido]-ethyl}-piperidin-4-yl)-2,5-dimethoxy-benzenesulfonamide;
N-Cyclopropyl-N-(1-{2-[3-(2,6-dimethyl-pyridin-4-yl)-ureido]-ethyl}-piperidin-4-yl)-2-methoxy-4-methyl-benzenesulfonamide;
N-Ethyl-N-(1-{2-[3-(2-ethyl-6-methyl-pyridin-4-yl)-ureido]-ethyl}-piperidin-4-yl)-2-methoxy-4-methyl-benzenesulfonamide;
N-Ethyl-N-(1-{2-[3-(2-ethyl-6-methyl-pyridin-4-yl)-ureido]-ethyl}-piperidin-4-yl)-3,4-dimethoxy-benzenesulfonamide;
N-Ethyl-N-(1-{2-[3-(2-ethyl-6-methyl-pyridin-4-yl)-ureido]-ethyl}-piperidin-4-yl)-3-methoxy-benzenesulfonamide;
1-(4-Chloro-phenyl)-cyclopropanecarboxylic acid (1-{2-[3-(2,6-dimethyl-pyridin-4-yl)-ureido]-ethyl}-piperidin-4-yl)-methyl-amide;
2-(4-Chloro-phenyl)-N-ethyl-N-(1-{2-[3-(2-ethyl-6-methyl-pyridin-4-yl)-ureido]-ethyl}-piperidin-4-yl)-isobutyramide;
2-(3,4-Dichloro-phenyl)-N-(1-{2-[3-(2,6-dimethyl-pyridin-4-yl)-ureido]-ethyl}-piperidin-4-yl)-N-ethyl-acetamide;
2-(4-Chloro-phenyl)-N-(1-{2-[3-(2,6-dimethyl-pyridin-4-yl)-ureido]-ethyl}-piperidin-4-yl)-N-ethyl-isobutyramide;
1-(4-Chloro-phenyl)-cyclopropanecarboxylic acid (1-{2-[3-(2,6-dimethyl-pyridin-4-yl)-ureido]-ethyl}-piperidin-4-yl)-ethyl-amide;
1-Phenyl-cyclopropanecarboxylic acid ethyl-(1-{2-[3-(2-ethyl-6-methyl-pyridin-4-yl)-ureido]-ethyl}-piperidin-4-yl)-amide;
1-(4-Chloro-phenyl)-cyclopropanecarboxylic acid ethyl-(1-{2-[3-(2-ethyl-6-methyl-pyridin-4-yl)-ureido]-ethyl}-piperidin-4-yl)-amide;
2-(4-Chloro-phenyl)-N-ethyl-N-(1-{2-[3-(2-ethyl-6-methyl-pyridin-4-yl)-ureido]-ethyl}-piperidin-4-yl)-acetamide;
2-(4-Chloro-phenyl)-N-cyclopropyl-N-(1-{2-[3-(2,6-dimethyl-pyridin-4-yl)-ureido]-ethyl}-piperidin-4-yl)-isobutyramide;
2-(4-Chloro-phenyl)-N-cyclopropyl-N-(1-{2-[3-(2,6-dimethyl-pyridin-4-yl)-ureido]-ethyl}-piperidin-4-yl)-acetamide;
1-(4-Chloro-phenyl)-cyclopropanecarboxylic acid cyclopropyl-(1-{2-[3-(2,6-dimethyl-pyridin-4-yl)-ureido]-ethyl}-piperidin-4-yl)-amide;
1-Phenyl-cyclopropanecarboxylic acid cyclopropyl-(1-{2-[3-(2,6-dimethyl-pyridin-4-yl)-ureido]-ethyl}-piperidin-4-yl)-amide;
N-(1-{2-[3-(2,6-Dimethyl-pyridin-4-yl)-ureido]-ethyl}-piperidin-4-yl)-N-ethyl-2-methoxy-benzenesulfonamide.

9. A compound selected from the group consisting of:
N-Cyclopropyl-N-(1-{2-[3-(2,6-dimethyl-pyridin-4-yl)-ureido]-ethyl}-piperidin-4-yl)-2-(4-methoxy-phenyl)-acetamide;
N-(1-{2-[3-(2,6-Dimethyl-pyridin-4-yl)-ureido]-ethyl}-piperidin-4-yl)-N-methyl-benzenesulfonamide;
N-(1-{2-[3-(2,6-Dimethyl-pyridin-4-yl)-ureido]-ethyl}-piperidin-4-yl)-3-methoxy-N-methyl-benzenesulfonamide;
N-(1-{2-[3-(2,6-Dimethyl-pyridin-4-yl)-ureido]-ethyl}-piperidin-4-yl)-3,4-dimethoxy-N-methyl-benzenesulfonamide;
N-(1-{2-[3-(2,6-Dimethyl-pyridin-4-yl)-ureido]-ethyl}-piperidin-4-yl)-2-methoxy-4,N-dimethyl-benzenesulfonamide;
N-(1-{2-[3-(2,6-Dimethyl-pyridin-4-yl)-ureido]-ethyl}-piperidin-4-yl)-4-fluoro-N-methyl-benzenesulfonamide;
N-(1-{2-[3-(2,6-Dimethyl-pyridin-4-yl)-ureido]-ethyl}-piperidin-4-yl)-3-fluoro-N-methyl-benzenesulfonamide;
N-(1-{2-[3-(2,6-Dimethyl-pyridin-4-yl)-ureido]-ethyl}-piperidin-4-yl)-2-fluoro-N-methyl-benzenesulfonamide;

N-(1-{2-[3-(2,6-Dimethyl-pyridin-4-yl)-ureido]-ethyl}-piperidin-4-yl)-2,4-difluoro-N-methyl-benzenesulfonamide;

N-(1-{2-[3-(2,6-Dimethyl-pyridin-4-yl)-ureido]-ethyl}-piperidin-4-yl)-3,4-difluoro-N-methyl-benzenesulfonamide;

N-(1-{2-[3-(2,6-Dimethyl-pyridin-4-yl)-ureido]-ethyl}-piperidin-4-yl)-2,6-difluoro-N-methyl-benzenesulfonamide;

N-(1-{2-[3-(2,6-Dimethyl-pyridin-4-yl)-ureido]-ethyl}-piperidin-4-yl)-3,N-dimethyl-benzenesulfonamide;

N-(1-{2-[3-(2,6-Dimethyl-pyridin-4-yl)-ureido]-ethyl}-piperidin-4-yl)-2,N-dimethyl-benzenesulfonamide;

N-(1-{2-[3-(2,6-Dimethyl-pyridin-4-yl)-ureido]-ethyl}-piperidin-4-yl)-4-methoxy-2,3,6,N-tetramethyl-benzenesulfonamide;

3-Chloro-N-(1-{2-[3-(2,6-dimethyl-pyridin-4-yl)-ureido]-ethyl}-piperidin-4-yl)-N-methyl-benzenesulfonamide;

2-Chloro-N-(1-{2-[3-(2,6-dimethyl-pyridin-4-yl)-ureido]-ethyl}-piperidin-4-yl)-N-methyl-benzenesulfonamide;

N-(1-{2-[3-(2,6-Dimethyl-pyridin-4-yl)-ureido]-ethyl}-piperidin-4-yl)-N-methyl-3-trifluoromethyl-benzenesulfonamide;

Thiophene-2-sulfonic acid (1-{2-[3-(2,6-dimethyl-pyridin-4-yl)-ureido]-ethyl}-piperidin-4-yl)-methyl-amide;

N-Cyclopropyl-N-(1-{2-[3-(2,6-dimethyl-pyridin-4-yl)-ureido]-ethyl}-piperidin-4-yl)-2-fluoro-benzenesulfonamide;

N-Cyclopropyl-N-(1-{2-[3-(2,6-dimethyl-pyridin-4-yl)-ureido]-ethyl}-piperidin-4-yl)-3,4-difluoro-benzenesulfonamide;

N-Cyclopropyl-N-(1-{2-[3-(2,6-dimethyl-pyridin-4-yl)-ureido]-ethyl}-piperidin-4-yl)-2-methyl-benzenesulfonamide;

N-Cyclopropyl-N-(1-{2-[3-(2,6-dimethyl-pyridin-4-yl)-ureido]-ethyl}-piperidin-4-yl)-2-trifluoromethyl-benzenesulfonamide;

Thiophene-2-sulfonic acid cyclopropyl-(1-{2-[3-(2,6-dimethyl-pyridin-4-yl)-ureido]-ethyl}-piperidin-4-yl)-amide;

2-(3,4-Dichloro-phenyl)-N-(1-{2-[3-(2,6-dimethyl-pyridin-4-yl)-ureido]-ethyl}-piperidin-4-yl)-N-methyl-acetamide;

1-Phenyl-cyclopropanecarboxylic acid (1-{2-[3-(2,6-dimethyl-pyridin-4-yl)-ureido]-ethyl}-piperidin-4-yl)-methyl-amide;

1-(4-Methoxy-phenyl)-cyclopropanecarboxylic acid (1-{2-[3-(2,6-dimethyl-pyridin-4-yl)-ureido]-ethyl}-piperidin-4-yl)-methyl-amide;

2-(4-Chloro-phenyl)-N-(1-{2-[3-(2,6-dimethyl-pyridin-4-yl)-ureido]-ethyl}-piperidin-4-yl)-N-methyl-acetamide;

N-(1-{2-[3-(2,6-Dimethyl-pyridin-4-yl)-ureido]-ethyl}-piperidin-4-yl)-2-(4-fluoro-phenyl)-N-methyl-acetamide;

N-(1-{2-[3-(2,6-Dimethyl-pyridin-4-yl)-ureido]-ethyl}-piperidin-4-yl)-N-methyl-2-phenyl-acetamide;

2-(3-Chloro-phenyl)-N-(1-{2-[3-(2,6-dimethyl-pyridin-4-yl)-ureido]-ethyl}-piperidin-4-yl)-N-methyl-acetamide;

2-(2-Chloro-phenyl)-N-(1-{2-[3-(2,6-dimethyl-pyridin-4-yl)-ureido]-ethyl}-piperidin-4-yl)-N-ethyl-acetamide;

N-(1-{2-[3-(2,6-Dimethyl-pyridin-4-yl)-ureido]-ethyl}-piperidin-4-yl)-N-ethyl-2-(2-methoxy-phenyl)-acetamide;

1-Phenyl-cyclopropanecarboxylic acid (1-{2-[3-(2,6-dimethyl-pyridin-4-yl)-ureido]-ethyl}-piperidin-4-yl)-ethyl-amide;

1-(4-Methoxy-phenyl)-cyclopropanecarboxylic acid (1-{2-[3-(2,6-dimethyl-pyridin-4-yl)-ureido]-ethyl}-piperidin-4-yl)-ethyl-amide;

N-(1-{2-[3-(2,6-Dimethyl-pyridin-4-yl)-ureido]-ethyl}-piperidin-4-yl)-N-ethyl-2-phenyl-acetamide;

N-(1-{2-[3-(2,6-Dimethyl-pyridin-4-yl)-ureido]-ethyl}-piperidin-4-yl)-N-ethyl-2-(4-methoxy-phenyl)-acetamide;

N-(1-{2-[3-(2,6-Dimethyl-pyridin-4-yl)-ureido]-ethyl}-piperidin-4-yl)-N-ethyl-4-methoxy-benzamide;

N-(1-{2-[3-(2,6-Dimethyl-pyridin-4-yl)-ureido]-ethyl}-piperidin-4-yl)-N-ethyl-3,4-dimethoxy-benzamide;

N-(1-{2-[3-(2,6-Dimethyl-pyridin-4-yl)-ureido]-ethyl}-piperidin-4-yl)-N-ethyl-4-fluoro-benzamide;

N-(1-{2-[3-(2,6-Dimethyl-pyridin-4-yl)-ureido]-ethyl}-piperidin-4-yl)-N-ethyl-2-(3-methoxy-phenyl)-acetamide;

2-(3,4-Dimethoxy-phenyl)-N-(1-{2-[3-(2,6-dimethyl-pyridin-4-yl)-ureido]-ethyl}-piperidin-4-yl)-N-ethyl-acetamide;

N-(1-{2-[3-(2,6-Dimethyl-pyridin-4-yl)-ureido]-ethyl}-piperidin-4-yl)-N-ethyl-2-thiophen-2-yl-acetamide;

N-(1-{2-[3-(2,6-Dimethyl-pyridin-4-yl)-ureido]-ethyl}-piperidin-4-yl)-N-ethyl-2-(4-fluoro-phenyl)-acetamide;

N-(1-{2-[3-(2,6-Dimethyl-pyridin-4-yl)-ureido]-ethyl}-piperidin-4-yl)-N-ethyl-benzamide;

1-(4-Methoxy-phenyl)-cyclopropanecarboxylic acid ethyl-(1-{2-[3-(2-ethyl-6-methyl-pyridin-4-yl)-ureido]-ethyl}-piperidin-4-yl)-amide;

N-Ethyl-N-(1-{2-[3-(2-ethyl-6-methyl-pyridin-4-yl)-ureido]-ethyl}-piperidin-4-yl)-2-phenyl-acetamide;

1-(4-Methoxy-phenyl)-cyclopropanecarboxylic acid cyclopropyl-(1-{2-[3-(2,6-dimethyl-pyridin-4-yl)-ureido]-ethyl}-piperidin-4-yl)-amide.

10. A pharmaceutical composition containing a compound of any one of claim 1, 2, 3, 4-7 or 8-9 and pharmaceutically acceptable carrier materials and adjuvants.

11. A compound according to claim 8 or pharmaceutically acceptable salts thereof.

12. A compound according to claim 9 or pharmaceutically acceptable salts thereof.

* * * * *